United States Patent
York et al.

(10) Patent No.: US 7,783,380 B2
(45) Date of Patent: Aug. 24, 2010

(54) SYSTEM AND METHOD FOR MEASURING, MONITORING AND CONTROLLING WASHROOM DISPENSERS AND PRODUCTS

(75) Inventors: Cheryl Lynn York, Canton, GA (US); Joseph Mitchell, Alpharetta, GA (US); Richard Paul Lewis, Marietta, GA (US); Paul Francis Tramontina, Alpharetta, GA (US); Ronald Raymond Padak, Suwanee, GA (US); James Joseph Detamore, Atlanta, GA (US); John Robert Oyler, Horsham (GB); James Alexander Winder, Chatham (GB)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1201 days.

(21) Appl. No.: 11/015,346

(22) Filed: Dec. 17, 2004

(65) Prior Publication Data

US 2005/0171634 A1    Aug. 4, 2005

Related U.S. Application Data

(63) Continuation-in-part of application No. 10/750,238, filed on Dec. 31, 2003.

(51) Int. Cl.
*G06F 17/00* (2006.01)
(52) U.S. Cl. .................. 700/240; 700/231; 700/232; 700/236; 700/244; 700/233; 700/241
(58) Field of Classification Search .......... 700/231–244
See application file for complete search history.

(56) References Cited

U.S. PATENT DOCUMENTS

| 3,058,223 A | 10/1962 | Schmidt et al. |
| 3,167,865 A | 2/1965 | Steinberg |
| 3,938,120 A | 2/1976 | O'Connell |
| 4,097,726 A | 6/1978 | Satoh et al. |
| 4,100,581 A | 7/1978 | Slack et al. |

(Continued)

FOREIGN PATENT DOCUMENTS

CA    2 265 483 A1    10/2000

(Continued)

OTHER PUBLICATIONS

U.S. Appl. No. 10/950,965.

(Continued)

*Primary Examiner*—Gene Crawford
*Assistant Examiner*—Michael K Collins
(74) *Attorney, Agent, or Firm*—Dority & Manning, P.A.

(57) ABSTRACT

An apparatus for the dispensing of product is provided. The apparatus may include a dispenser sensor unit in communication with a dispenser that is configured for the dispensing of product. The dispenser sensor unit may be configured for detecting information about the product and for varying a dispensing parameter of the dispenser. A data communications unit in communication with the dispenser sensor unit may also be provided and may be configured for receiving information from the dispenser sensor unit. A washroom monitoring station in communication with the data communications unit may also be present and may be configured for receiving information from the data communications unit. The dispenser sensor unit may be configured for receiving a communication so as to vary a dispensing parameter of the dispenser.

29 Claims, 28 Drawing Sheets

U.S. PATENT DOCUMENTS

| | | | |
|---|---|---|---|
| 4,131,044 A | 12/1978 | Cassia | |
| 4,151,403 A | 4/1979 | Woolston | |
| 4,228,470 A | 10/1980 | Rahamin et al. | |
| 4,302,752 A | 11/1981 | Weitzler | |
| 4,335,439 A | 6/1982 | St. Denis | |
| 4,456,193 A | 6/1984 | Westover | |
| 4,475,163 A | 10/1984 | Chandler et al. | |
| 4,535,949 A | 8/1985 | Olsson | |
| 4,570,348 A | 2/1986 | Amsler et al. | |
| 4,611,768 A | 9/1986 | Voss et al. | |
| 4,666,099 A | 5/1987 | Hoffman et al. | |
| 4,676,131 A | 6/1987 | Cassia | |
| 4,704,798 A | 11/1987 | Hird | |
| 4,721,265 A | 1/1988 | Hawkins | |
| 4,738,176 A | 4/1988 | Cassia | |
| 4,756,030 A * | 7/1988 | Juliver | 4/668 |
| 4,757,337 A | 7/1988 | Shikaumi | |
| 4,765,555 A | 8/1988 | Gambino | |
| 4,767,922 A | 8/1988 | Stauffer | |
| 4,786,005 A | 11/1988 | Hoffman et al. | |
| 4,790,490 A | 12/1988 | Chakravorty | |
| 4,796,825 A | 1/1989 | Hawkins | |
| 4,817,483 A | 4/1989 | Armbruster | |
| 4,826,262 A | 5/1989 | Hartman et al. | |
| 4,835,520 A | 5/1989 | Aiello | |
| 4,835,698 A | 5/1989 | Beery et al. | |
| 4,872,592 A | 10/1989 | Anazawa | |
| 4,882,568 A | 11/1989 | Kyser et al. | |
| 4,896,144 A | 1/1990 | Bogstad | |
| 4,960,248 A | 10/1990 | Bauer et al. | |
| 4,994,722 A | 2/1991 | Dolan et al. | |
| 4,999,611 A | 3/1991 | Zehnder, Jr. | |
| 5,031,258 A * | 7/1991 | Shaw | 4/623 |
| 5,050,093 A | 9/1991 | Reddy et al. | |
| 5,107,734 A | 4/1992 | Armbruster | |
| 5,131,302 A | 7/1992 | Watanabe | |
| 5,153,560 A | 10/1992 | Ichikawa | |
| 5,155,474 A | 10/1992 | Park et al. | |
| 5,177,446 A | 1/1993 | Boriani et al. | |
| 5,202,666 A | 4/1993 | Knippscheer | |
| 5,205,454 A | 4/1993 | Schultz et al. | |
| 5,207,784 A * | 5/1993 | Schwartzendruber | 221/6 |
| 5,250,941 A | 10/1993 | McGregor et al. | |
| 5,257,462 A | 11/1993 | Buttermann | |
| 5,280,274 A | 1/1994 | Uemura et al. | |
| 5,299,713 A * | 4/1994 | Saitoh | 222/51 |
| 5,452,832 A | 9/1995 | Niada | |
| 5,463,369 A | 10/1995 | Lamping | |
| 5,500,517 A | 3/1996 | Cagliostro | |
| 5,540,332 A | 7/1996 | Kopacz et al. | |
| 5,570,938 A | 11/1996 | Butler | |
| 5,604,992 A | 2/1997 | Robinson | |
| 5,608,643 A * | 3/1997 | Wichter et al. | 700/244 |
| 5,610,589 A | 3/1997 | Evans et al. | |
| 5,620,148 A | 4/1997 | Mitchell | |
| 5,625,908 A | 5/1997 | Shaw | |
| 5,627,522 A | 5/1997 | Walker et al. | |
| 5,691,919 A | 11/1997 | Gemmell et al. | |
| 5,701,252 A | 12/1997 | Facchin et al. | |
| 5,711,480 A | 1/1998 | Zepke et al. | |
| 5,721,421 A | 2/1998 | VanDonkelaar | |
| 5,721,532 A | 2/1998 | Lehmann et al. | |
| 5,772,291 A | 6/1998 | Byrd et al. | |
| 5,793,653 A | 8/1998 | Segal | |
| 5,805,442 A | 9/1998 | Crater et al. | |
| 5,810,201 A | 9/1998 | Besse et al. | |
| 5,812,059 A | 9/1998 | Shaw et al. | |
| 5,861,808 A | 1/1999 | Lehmann et al. | |
| 5,870,015 A | 2/1999 | Hinkel | |
| 5,878,381 A | 3/1999 | Gemmell et al. | |
| 5,903,395 A | 5/1999 | Rallison et al. | |
| 5,918,197 A | 6/1999 | Toussant et al. | |
| 5,945,910 A * | 8/1999 | Gorra | 340/573.1 |
| 5,952,924 A | 9/1999 | Evans et al. | |
| 5,966,753 A | 10/1999 | Gauthier et al. | |
| 5,975,737 A | 11/1999 | Crater et al. | |
| 5,997,167 A | 12/1999 | Crater et al. | |
| 6,028,520 A | 2/2000 | Maehre | |
| 6,029,600 A | 2/2000 | Davis | |
| 6,031,461 A | 2/2000 | Lynn | |
| 6,032,303 A | 3/2000 | Schmidt | |
| 6,069,354 A | 5/2000 | Alfano et al. | |
| 6,079,035 A | 6/2000 | Suzuki et al. | |
| 6,079,305 A | 6/2000 | Bloch et al. | |
| 6,105,898 A | 8/2000 | Byrd et al. | |
| 6,125,482 A | 10/2000 | Foster | |
| 6,147,607 A | 11/2000 | Lynn | |
| 6,152,397 A | 11/2000 | Purcell | |
| 6,178,569 B1 | 1/2001 | Quintana | |
| 6,209,752 B1 | 4/2001 | Mitchell et al. | |
| 6,211,788 B1 | 4/2001 | Lynn et al. | |
| 6,213,424 B1 | 4/2001 | Helfer-Grand | |
| 6,224,010 B1 | 5/2001 | Morand | |
| 6,236,317 B1 * | 5/2001 | Cohen et al. | 340/573.1 |
| 6,250,530 B1 | 6/2001 | LaCount et al. | |
| 6,259,367 B1 | 7/2001 | Klein | |
| 6,278,372 B1 | 8/2001 | Velasco, Jr. et al. | |
| 6,293,486 B1 | 9/2001 | Byrd et al. | |
| 6,317,717 B1 * | 11/2001 | Lindsey et al. | 704/275 |
| 6,321,963 B1 | 11/2001 | Gracyalny et al. | |
| 6,354,493 B1 | 3/2002 | Mon | |
| 6,354,533 B1 | 3/2002 | Jespersen | |
| 6,360,181 B1 * | 3/2002 | Gemmell et al. | 702/128 |
| 6,362,738 B1 | 3/2002 | Vega | |
| 6,363,057 B1 | 3/2002 | Ardalan et al. | |
| 6,375,038 B1 | 4/2002 | Daansen et al. | |
| 6,411,920 B1 * | 6/2002 | McConnell et al. | 702/177 |
| 6,412,655 B1 | 7/2002 | Stuetzel et al. | |
| 6,412,679 B2 | 7/2002 | Formon et al. | |
| 6,417,773 B1 | 7/2002 | Vlahos et al. | |
| 6,419,136 B2 * | 7/2002 | Formon et al. | 225/14 |
| 6,426,701 B1 | 7/2002 | Levy et al. | |
| 6,451,154 B1 | 9/2002 | Grabau et al. | |
| 6,550,672 B1 | 4/2003 | Tracy et al. | |
| 6,577,240 B2 | 6/2003 | Armstrong | |
| 6,607,160 B2 | 8/2003 | Lewis et al. | |
| 6,650,962 B2 * | 11/2003 | Sudolcan et al. | 700/231 |
| 6,671,894 B1 | 1/2004 | Sigrist | |
| 6,710,606 B2 * | 3/2004 | Morris | 324/658 |
| 6,727,818 B1 | 4/2004 | Wildman et al. | |
| 6,895,296 B2 * | 5/2005 | Holt et al. | 700/139 |
| 7,015,816 B2 * | 3/2006 | Wildman et al. | 340/573.1 |
| 7,044,421 B1 * | 5/2006 | Omdoll et al. | 242/564.4 |
| 7,072,738 B2 * | 7/2006 | Bonney et al. | 700/237 |
| 7,370,824 B1 * | 5/2008 | Osborne | 242/563 |
| 2001/0017309 A1 | 8/2001 | Formon et al. | |
| 2002/0061500 A1 | 5/2002 | Collopy | |
| 2002/0117578 A1 * | 8/2002 | Denen et al. | 242/563 |
| 2002/0145523 A1 | 10/2002 | Robaey | |
| 2002/0175182 A1 | 11/2002 | Matthews | |
| 2002/0184105 A1 | 12/2002 | Czuchry, Jr. et al. | |
| 2002/0196150 A1 * | 12/2002 | Wildman | 340/573.1 |
| 2003/0019536 A1 | 1/2003 | Smith | |
| 2003/0078691 A1 | 4/2003 | Holt et al. | |
| 2004/0001009 A1 | 1/2004 | Winings et al. | |
| 2005/0011987 A1 | 1/2005 | Lemaire et al. | |

FOREIGN PATENT DOCUMENTS

| | | |
|---|---|---|
| DE | 200 16 735 U1 | 11/2000 |
| EP | 0209223 B1 | 1/1987 |
| EP | 0326528 B1 | 8/1989 |
| EP | 0574372 B1 | 12/1993 |
| EP | 0700024 B1 | 3/1996 |

| | | |
|---|---|---|
| EP | 0792971 B1 | 9/1997 |
| JP | 2003098265 | 4/2003 |
| NL | 8600003 | 8/1987 |
| WO | WO 94/27489 | 8/1994 |
| WO | WO 9504333 A1 | 2/1995 |
| WO | WO 9729465 A1 | 8/1997 |
| WO | WO 0248955 A1 | 6/2002 |

OTHER PUBLICATIONS

U.S. Appl. No. 10/032,829.
U.S. Appl. No. 10/750,238.
ASTM Designation: D 3776-96, "Standard Test Method for Mass Per Unit Area (Weight) of Fabric", Published Jun. 1996, pp. 86-89.
TAPPI Official Test Method T 220 sp-96, "Physical Testing of Pulp Handsheets," published 1996, pp. 1-6.

* cited by examiner

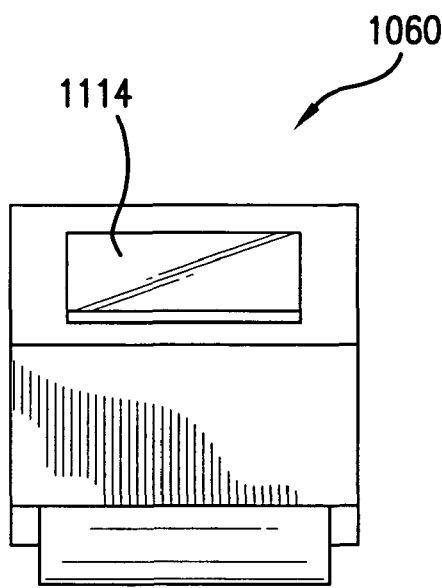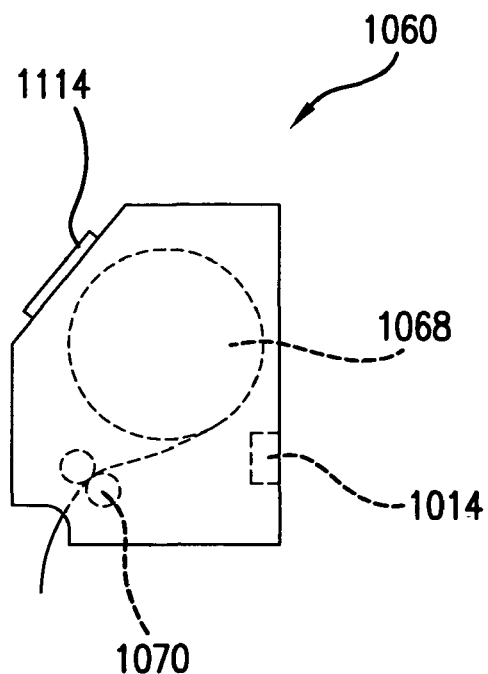
FIG.27A  FIG.27B
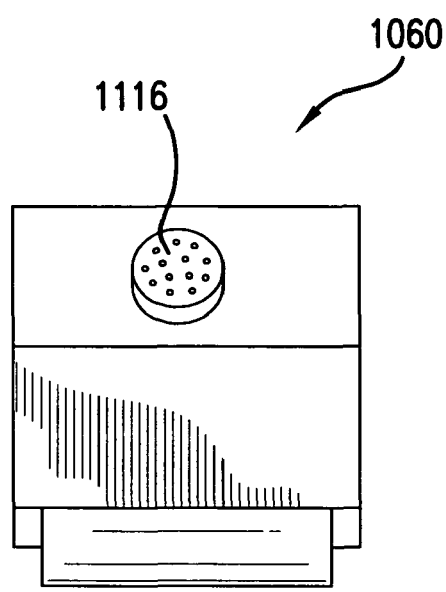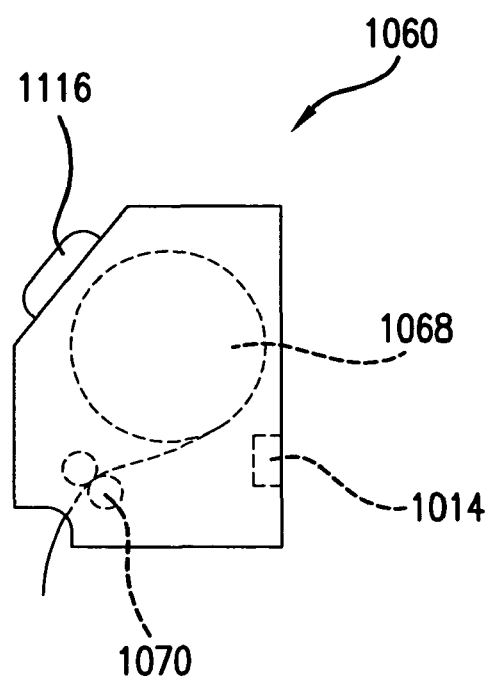
FIG.28A  FIG.28B

SYSTEM AND METHOD FOR MEASURING, MONITORING AND CONTROLLING WASHROOM DISPENSERS AND PRODUCTS

CROSS-REFERENCE TO RELATED APPLICATIONS

The present application is a Continuation-In-Part (CIP) of U.S. patent application Ser. No. 10/750,238 filed on Dec. 31, 2003, entitled "Dispenser with Electronic Sensing Device to Control Delivered Sheet Length" whose inventors are Paul Francis Tramontina, David W. Kapiloff, Stephen L. Phelps, Darrell R. Johnson, and Gerald L. Clark. application Ser. No. 10/750,238 is incorporated by reference herein in its entirety for all purposes.

BACKGROUND

Washrooms in commercial and residential buildings typically include products such as toilet tissue, paper towels, diapers, feminine products, liquid products such as soap, and aerosol products such as air fresheners. These products are typically housed by a dispenser and are dispensed as needed by the user. Currently, janitors or maintenance personnel roam the buildings in which they are working to service the washrooms, or the janitors or maintenance personnel are sent to service a particular washroom or dispenser after a problem has occurred. Fixing of a problem with the washroom after the fact results in numerous tenant complaints and overall dissatisfaction. Additionally, janitorial or maintenance personnel resources are focused on servicing emergencies and are pulled away from other tasks. Additionally, waste of product is high since janitors or maintenance personnel tend to change out products before the dispensers are empty in order to avoid running out of the products before the janitors or maintenance personnel return to once again service the dispensers.

The remote collection and use of real-time information has been found to be desirable in order to allow for efficient operation of other systems in commercial and residential properties. For instance, real-time measuring, monitoring, and controlling of security systems, fire systems, and heating ventilation and air conditioning systems (HVAC) have been developed in order to provide for safe, productive environments and to maintain occupant satisfaction levels in commercial and residential properties. However, a need in the art exists for a system and methodology to measure, monitor and control product dispensers and other components of washrooms in order to better manage washrooms so as to prevent product outages, reduce unnecessary waste, increase safety, improve the productivity of janitors and maintenance personnel, track washroom usage, monitor washroom inventory, control product dispensers, and facilitate product reorders.

Dispensers that automatically dispense product, such as paper towels, upon detecting the presence of an individual are desirable because they eliminate the need for the user to physically contact the dispenser hence preventing the spread of germs. These types of dispensers, however, may be disadvantageous in that they dispense at a predetermined setting that provides the same amount of sheet material to a user regardless of whether the sheet material is a soft, highly absorbent sheet material, or a sheet material that has a much lower absorbency. In these instances, either too much or too little of the sheet material will be dispensed to the user in order to dry his or her hands to the user's satisfaction. Dispensing of too much sheet material will result in unnecessary wasted product, and dispensing of too little of the sheet material will require the user to once again dispense sheet material from the product possibly resulting in additional waste. Wasted sheet material results in higher costs to maintain the sheet material in the dispenser and causes a greater environmental impact.

Prior dispensers have been designed in order to allow for a change in the length of the sheet material dispensed by a manual manipulation of the dispenser prior to introduction of a new roll of sheet material. However, this type of adjustment requires the janitor or maintenance personnel to manually adjust the sheet material length during replacement of a roll. Apart from requiring time, effort and expertise from the janitor or maintenance personnel, there is the risk of human error in the resetting operation.

SUMMARY

Various features and advantages of the invention will be set forth in part in the following description, or may be obvious from the description, or may be learned from practice of the invention.

In one embodiment, an apparatus may be provided for the dispensing of product in washrooms or other locations that allow for a dispensing parameter of a dispenser to be varied without requiring a manual adjustment of the dispenser by a janitor or maintenance personnel.

In accordance with one embodiment, a dispenser configured for the dispensing of product may be provided. A dispenser sensor unit may be placed in communication with the dispenser and may be configured for detecting information about the product. The dispenser sensor unit may be configured for varying a dispensing parameter of the dispenser. A data communications unit may be placed in communication with the dispenser sensor unit and may be configured for receiving information therefrom. A washroom monitoring station may be placed in communication with the data communications unit and may be likewise configured for receiving information therefrom. The dispenser sensor unit may be configured for receiving a communication so as to vary the dispensing parameter of the dispenser. The dispensing parameter may be selected from a multitude of various parameters such as, but not limited to, shot size, sheet length, time delay, light sensitivity and/or volume.

In accordance with another exemplary embodiment, the dispenser sensor unit may be configured for receiving the communication from the washroom monitoring station by way of the data communications unit in order to cause the dispenser to vary the dispensing parameter. Alternatively or additionally, the apparatus may be configured so that the dispenser sensor unit is configured for receiving the communication from a cell phone or PDA in order to cause a varying of the dispensing parameter.

Also included is an exemplary embodiment of the apparatus as discussed above where the dispenser sensor unit may be configured for identifying the product and for reporting the identification of the product to the washroom monitoring station through the data communications unit. Additionally, a reader may be included for identifying the product that may be an RFID reader, a barcode reader, a printed label reader, a magnetic strip reader, a smart tag reader a hologram reader, a luminescence reader and/or a fluorescence reader.

In accordance with another exemplary embodiment, the dispenser may have a visual display in communication with the washroom monitoring station through the data communications unit. The visual display may be configured for displaying information that may be changed through the washroom monitoring station. Additionally or alternatively, the apparatus may include in another exemplary embodiment an audio module configured for announcing an audio message. The audio module may be in communication with the washroom monitoring station through the data communications unit so that the washroom monitoring station may be configured for changing audio messages of the audio module.

In accordance with another exemplary embodiment, the dispenser sensor unit may be configured for identifying the product and reporting the identification of the product and the level of product remaining in the dispenser to a database. A product reordering mechanism may be included and may be configured for using the database in order to reorder product when low and to bill the customer for the reordered product.

Also included may be an apparatus for conveying information in a washroom. The apparatus may include a display that is configured for conveying information and a data communications unit in communication with the display. A washroom monitoring station may also be included and may be in communication with the data communications unit. The washroom monitoring station may be configured for communicating with the display through the data communications unit in order to modify information conveyed by the display. The display may be of any type. For example, the display may be a visual display and/or an audio module.

Another exemplary embodiment provides for an apparatus for monitoring the presence of water in a washroom. The apparatus may include an overflow sensor for detecting the presence of water. A data communications unit may be in wireless communication with the overflow sensor. Further, a washroom monitoring station may be included and may be in wireless communication with the data communications unit and with the overflow sensor through the data communications unit. The washroom monitoring station may be configured for indicating the presence of water when detected by the overflow sensor. The overflow sensor may be selected from a variety of sensors including, but not limited to, a moisture detector, a pressure sensor, and/or a float switch.

An apparatus may also be provided as described above that is capable of monitoring the flow of water to determine if excess water is being used by a faucet, toilet and/or urinal that is left running. A data communications unit may be in communication with the flow sensor. Further, a washroom monitoring station may be included and may be in communication with the data communications unit and with the flow sensor through the data communications unit. The washroom monitoring station may be configured for indicating the flow of water when detected by the flow sensor. The flow sensor may be selected from a variety of sensors including, but not limited to, a rotating vane and/or differential pressure unit.

Also provided for in accordance with yet another exemplary embodiment is an apparatus as described above that may be capable of monitoring washroom hand washing compliance. The apparatus may include a sensor for indicating the presence and identity of a user of the washroom. A dispenser sensor unit may be capable of detecting the removal of product from the dispenser. A data communications unit may also be included and may be in communication with the sensor. A washroom monitoring station may be placed in communication with the data communications unit. The data communications unit may be configured for receiving information from the dispenser sensor unit and the data communications unit so as to monitor product removal by the individual.

Also provided in accordance with another exemplary embodiment is an apparatus as immediately discussed in which the washroom monitoring station may be configured for reporting lack of product removal to the individual by way of a cell phone, PDA, a pager and/or a telephone.

Also provided for in accordance with yet another exemplary embodiment is an apparatus as previously discussed where the dispenser may be a paper towel dispenser, a soap dispenser, a toilet tissue dispenser and/or a sink, toilet or urinal.

Another exemplary embodiment exists in a dispenser for the dispensing of product. The dispenser may include a dispenser housing that is configured for holding the product. A lever may be provided and may be pivotally mounted to the dispenser housing and configured for engaging the product. The lever may be configured for pivoting to a low product position upon a reduction of the amount of product brought about by dispensing of product. A switch may be provided and may be configured for engagement with the lever when the lever is pivoted to the low product position. The switch may be configured for generating a low product signal when the lever is pivoted to the low product position.

Also provided in accordance with another exemplary embodiment is an apparatus for the dispensing of soap. The apparatus may include a dispenser sensor unit in communication with a soap dispenser. The dispenser sensor unit may be capable of detecting the amount of soap in the dispenser and also capable of varying the shot size of the dispenser. A data communications unit may also be provided and may be in wireless communication with the dispenser sensor unit. The data communications unit may be configured for receiving information from the dispenser sensor unit that includes at least the amount of soap remaining in the dispenser. A washroom monitoring station may be provided and may be in wireless communication with the data communications unit. The washroom monitoring station may be configured for receiving information from the data communications unit that includes at least the amount of soap remaining in the dispenser. The washroom monitoring station may be configured for communicating with the dispenser sensor unit through the data communications unit in order to vary the shot size of the dispenser.

A dispenser for the dispensing of product may also be provided in accordance with another exemplary embodiment. The dispenser may include a dispenser housing that is configured for holding product. A dispenser sensor unit may be included and may be configured for detecting the amount of product in the dispenser. A washroom monitoring station may also be provided and may be in wireless communication with the dispenser sensor unit. The washroom monitoring station may be configured for receiving information concerning the amount of product in the dispenser.

An apparatus in accordance with another exemplary embodiment for the dispensing of product may be provided. The apparatus may include a dispenser housing that is configured for holding product. A dispenser sensor unit may be included and may have an emitter configured for emitting infrared light. A detector may be provided and may be configured for receiving infrared light from the dispenser sensor unit so as to indicate whether product is present in the path of the infrared light.

A further exemplary embodiment exists in the apparatus as previously discussed where the dispenser sensor unit and the detector may be positioned at a low product point in the dispenser. Additionally, the product may be a paper stack in accordance with another exemplary embodiment.

Also provided is an apparatus for the dispensing of product in accordance with another exemplary embodiment. The apparatus may include a dispenser configured for the dispensing of product and a dispenser sensor unit configured for detecting a product low condition. A data communications unit may be in communication with the dispenser sensor unit and may be configured for receiving information from the dispenser sensor unit. A washroom monitoring station may be in communication with the data communications unit and may be configured for receiving information from the data communications unit. The washroom monitoring station may check an inventory of the product when the product low condition is detected and may reorder the product if sufficient product is not present in the inventory.

Another exemplary embodiment exists in the apparatus as immediately discussed where the washroom monitoring station may keep a record of the number of times the product low condition is detected. Additionally, or alternatively, the washroom monitoring station may bill a customer for the amount of product dispensed from the dispenser.

A further exemplary embodiment resides in an apparatus for monitoring a washroom that includes a camera configured for viewing the floor of the washroom. A data communications unit may be in communication with the camera and a washroom monitoring station may be in communication with the data communications unit. The washroom monitoring station may be configured for indicating the present of an object, such as water and/or debris, on the floor of the washroom.

These and other features, aspects and advantages of the present invention will become better understood with reference to the following description and appended claims. The accompanying drawings which are incorporated in and constitute part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 27A is a front view of a roll towel dispenser incorporating a visual display in accordance with an exemplary embodiment.

FIG. 27B is a side view of the roll towel dispenser in FIG. 27A.

FIG. 28A is a front view of a roll towel dispenser incorporating an audio module in accordance with an exemplary embodiment.

FIG. 28B is a side view of the roll towel dispenser in FIG. 28A.

Figure 1:
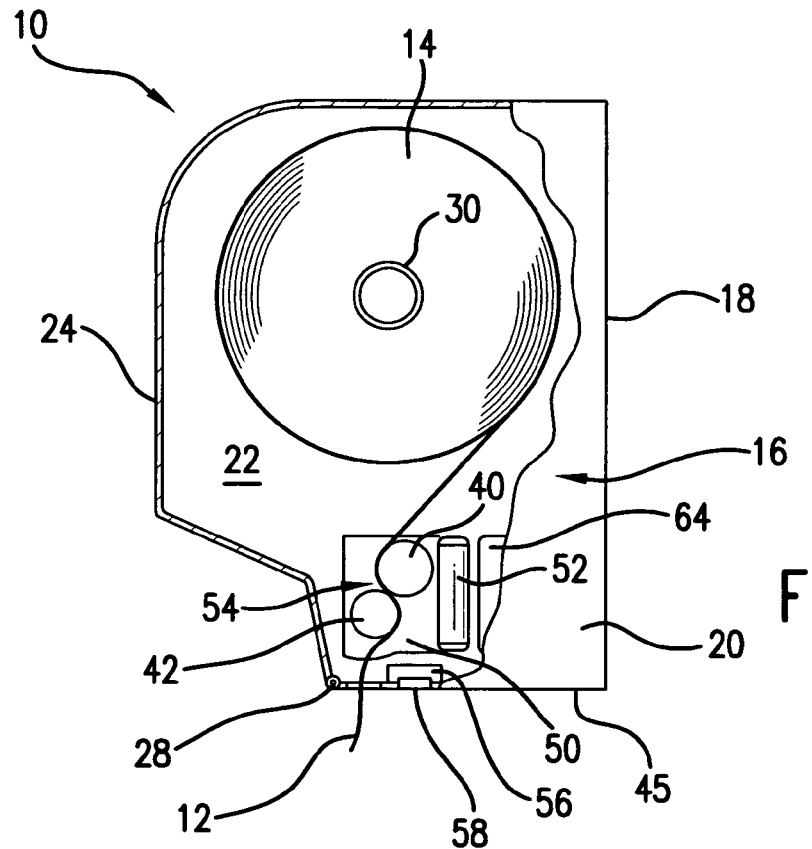
FIG. 1 is a side view, partially in cross-section, of a sheet material dispenser according to an exemplary embodiment.

Repeat use of reference characters in the present specification and drawings is intended to present same or analogous features or elements of the invention.

DEFINITIONS

As used herein, the term "identification" when used as a noun means anything on an object which serves to identify the object.

As used herein, the term "identifier" means a mechanism or a device for identifying an object from identification on the object.

As used herein, the term "comprising" is intended to be inclusive or open-ended, and is not intended to exclude additional elements or method steps which do not prevent operation of the invention.

As used herein, the term "fasteners" means devices that fasten, join, connect, secure, hold, or clamp components together. Fasteners include, but are not limited to, screws, nuts and bolts, rivets, snap-fits, tacks, nails, loop fasteners, and interlocking male/female connectors, such as fishhook connectors, a fish hook connector includes a male portion with a protrusion on its circumference. Inserting the male portion into the female portion substantially permanently locks the two portions together.

As used herein, the term "basis weight" (hereinafter may be referred to as "BW") is the weight per unit area of a sample and may be reported as grams per meter squared (gsm). The basis weight may be measured using test procedure ASTM D 3776-96 or TAPPI Test Method T-220.

As used herein, the term "hinge" refers to a jointed or flexible device that connects and permits pivoting or turning of a part to a stationary component. Hinges include, but are not limited to, metal pivotable connectors, such as those used to fasten a door to frame, and living hinges. Living hinges may be constructed from plastic and formed integrally between two members. A living hinge permits pivotable movement of one member in relation to another connected member.

As used herein, the term "couple" includes, but is not limited to, joining, connecting, fastening, linking, or associating two things integrally or interstitially together.

As used herein, the terms "sheet material" and "paper" means a material that is thin in comparison to its length and breadth. Generally speaking, sheet materials should exhibit a relatively flat planar configuration and be flexible to permit folding, rolling, stacking, and the like. Exemplary sheet materials and papers include, but are not limited to, paper tissue, bath/toilet tissue, paper towels, wipes, label rolls, or other fibrous, film, polymers, or filamentary products. The terms "sheet material" and "paper" may be used interchangeably.

As used herein, the term "product" or "products" includes, but is not limited to, a single sheet or roll, multiple sheets or rolls, or a single stack or multiple stacks. As such, the terms product or products are broad enough to cover any item such as but not limited to (water, soap, paper) held by or dispensed from a dispenser whether in multiple or singular form. The term may cover both individual sheets or sheets as well as the entire roll, stack or cartridge.

These terms may be defined with additional language in the remaining portions of the specification.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges and limits mentioned herein include all ranges located within, and also all values located under or above the prescribed limits. For instance, a range from 100-200 also includes ranges from 110-150, 170-190, and 153-162. Further, a limit of up to about 7 also includes a limit of up to about 5, up to about 3, and up to about 4.5.

FIG. 1 of the drawings illustrates a dispenser 10 for dispensing a web of sheet material 12 from a continuous roll 14 according to one embodiment of the present invention. The web of sheet material in this embodiment comprises an absorbent material, such as paper towelling, and so forth, which may be periodically perforated for separation.

Figure 2:
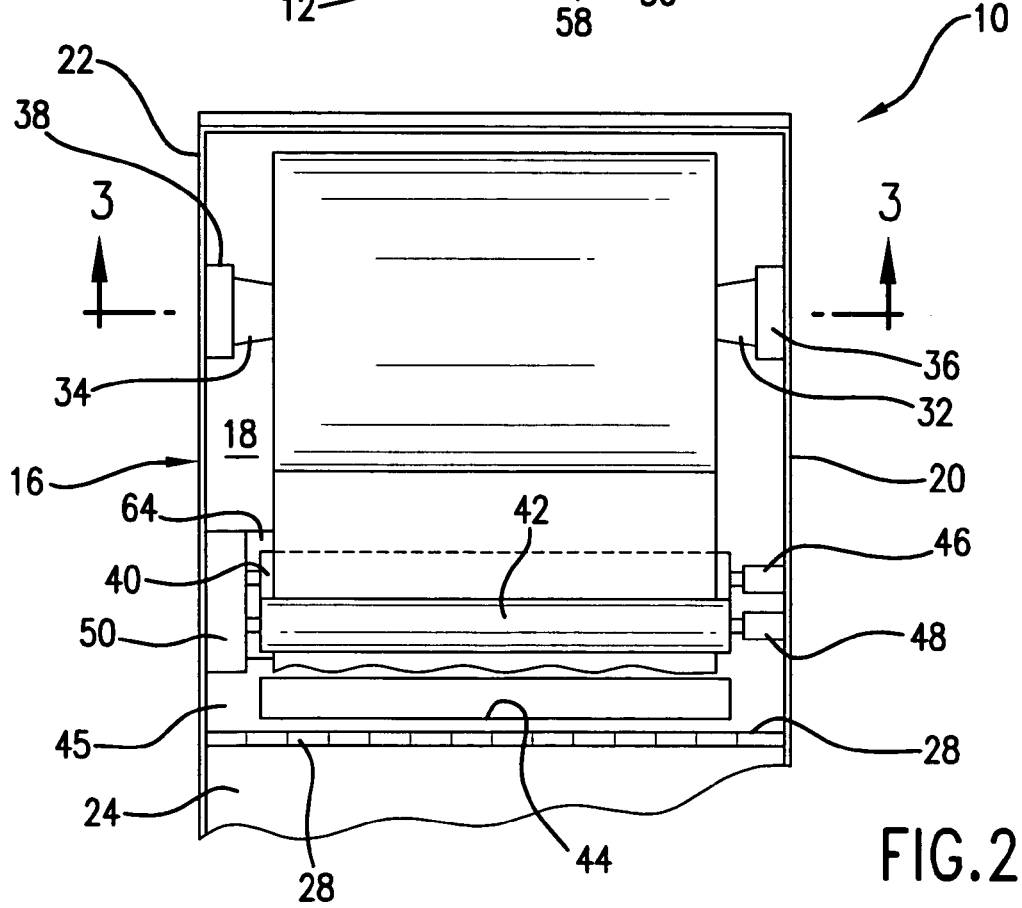
FIG. 2 is a front view of a portion of the dispenser of FIG. 1 in an open condition.

With reference also to FIG. 2 of the drawings, the dispenser 10 is seen to include a dispenser housing 16 having a back panel 18 mountable to a wall or similar vertical surface, a pair of opposed side panels 20 and 22, and a front cover 24. The front cover 24 is desirably, but not by way of limitation, pivotally connected to a lower portion of the housing 16 with hinges 28 so as to be movable between a closed condition, as illustrated in FIG. 1, and an open condition, as illustrated in FIG. 2. It will be appreciated that the front cover 24 may be connected by fasteners, screws, and any other mechanism known in the art. The front cover 24 of the dispenser housing 16 typically is opened for servicing or for loading a replacement sheet material roll into the dispenser 10. A latch (not shown) allows the front cover 24 to be locked in the closed condition so as to avoid unauthorised tampering with the dispenser components within the housing 16.

Figure 7:
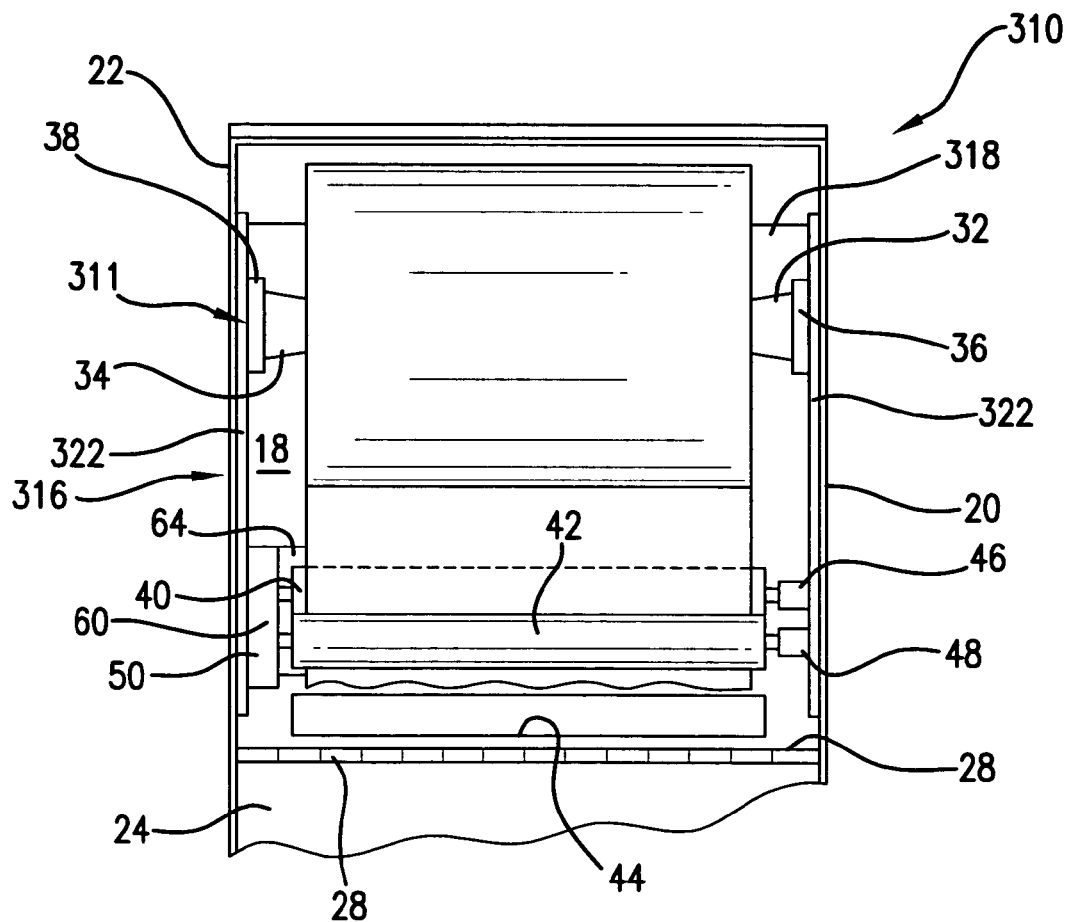
FIG. 7 is a front view of a portion of the dispenser of FIG. 1 in an open condition, showing a module which is inserted into the dispenser housing.

The sheet material roll 14 may include a core or sleeve 30. The sheet material roll 14 may, alternatively, be a coreless roll, such as that disclosed in U.S. Pat. No. 5,620,148 to J. Mitchell, which is hereby incorporated by reference in its entirety herein for all purposes. The sheet material roll 14 may be rotatably supported within the housing 16 by a pair of mounting hubs 32 and 34 which, in the present embodiment, are illustrated as connected to the side panels 20 and 22 of the housing 16 by means of roll holders 36 and 38. The outer circumference of the sheet material roll 14 may be supported by a portion of the housing without other support for unwinding of the roll 14. One such example is disclosed in U.S. Pat. No. 6,224,010, which is incorporated by reference in its entirety herein for all purposes. It will be appreciated, however, that the housing 16 may be provided as a separate unit with few or no mechanisms connected thereto. In this instance, some or all of the dispensing mechanisms shown and/or described herein may be provided as one or more modules which are inserted into the housing, as illustrated in FIG. 7. Examples of such dispenser housings and modules are disclosed in U.S. Pat. Nos. 4,131,044 and 6,079,035, both of which are incorporated by reference in their entirety herein for all purposes.

As can be seen, the sheet material 12 runs off the roll 14, between a pair of rollers 40 and 42, and through a dispensing opening 44, for example, in a lower end 45 of the housing 16. Alternatively, the dispensing opening may be formed in the front cover, or in both a portion of the front cover and a portion of the lower end (not shown). The opening 44 may have a serrated edge (not illustrated), or it may carry teeth (also not illustrated) for severing the web of sheet material (if is it not perforated). One end of the roller 40 may be rotatably mounted to the side panel 20 of the housing 16 or of a module housing (FIG. 7) by means of a roll holder 46, and one end of the roller 42 may be rotatably mounted to the side panel 20 of the housing 16 or of a module housing (FIG. 7) by means of a roll holder 48. The other ends of the rollers 40 and 42 may be rotatably mounted to the side panel 22 by means of roll holders concealed within a transmission housing 50. The transmission housing 50 contains a transmission (not visible) for transmitting drive from an electric motor 52 to the roller 40 so as to rotate this roller. Alternatively, at least one of the rollers may be mounted in the front cover, as disclosed generally in U.S. Pat. No. 6,607,160 which is incorporated by reference in its entirety herein for all purposes.

The rollers 40 and 42 together define a nip 54 having a gap which is desirably slightly smaller than the thickness of the sheet material on the roll 14. The sheet material 12 passes through the nip 54, as shown most clearly in FIG. 1, so that rotation of the drive roller 40 and the driven roller 42 pulls the sheet material off of the roll 14 and dispenses it through the dispensing opening 44.

An activation sensor 56 may be mounted to the lower end 45 of the housing 16 (or, alternatively, to a module in the housing (not shown)) adjacent a lens 58, as illustrated in FIG. 1. It will be understood, however, that the activation sensor 56 and/or lens 58, or any activations system shown and/or described herein or known in the art, may be mounted in any area of the housing, so long as it operates as described herein. In this embodiment of the invention, the sensor 56 is desirably, but not by way of limitation, a conventional passive sensor for detecting infrared radiation. Passive infrared detectors are known in the art, and are described, for example, in U.S. Pat. No. 4,757,337 to Shikaumi and U.S. Pat. No. 4,960,248 to Bauer et al., both of which are incorporated herein by reference. A passive infrared detector which may be used with the dispenser 10 is a Model 40623 sold by Eltec Instruments Inc. However, those of skill in the art will appreciate that various different infrared detectors are available, and that many of the available detectors are suitable for use with the dispenser 10. In practice, the sensor 56 is arranged to detect infrared radiation from a user's hand placed below the lens 58, and upon detecting the radiation, to transmit a signal for activating the electric motor 52 so as to dispense a length of sheet material through the dispensing opening 44.

It will by understood, however, that other activation mechanisms, such as capacitive and ultrasonic, may be used in the present invention. Capacitive proximity sensors produce an electrostatic field that will sense both metal objects and non-metallic materials such as paper, glass, liquids and cloth. Ultrasonic proximity sensors use a transducer to send and receive high frequency sound signals. When a target enters the beam the sound is reflected back to the sensor, causing it to energize or de-energize the output circuit. Another sensor type is inductive. In this case an electromagnetic field is used, however, detection is limited to only metallic objects.

Figure 3:
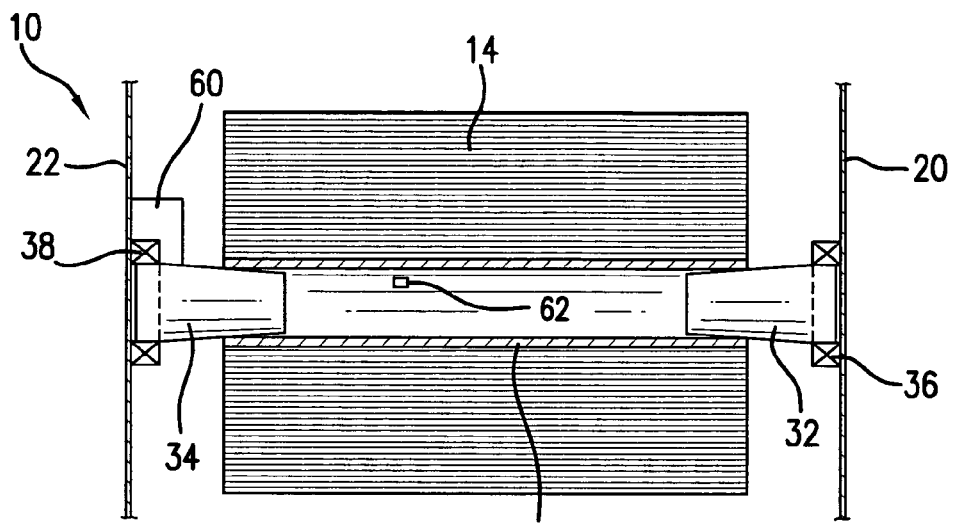
FIG. 3 is a cross-sectional view along the line 3-3 in FIG. 2.
Figure 3A:
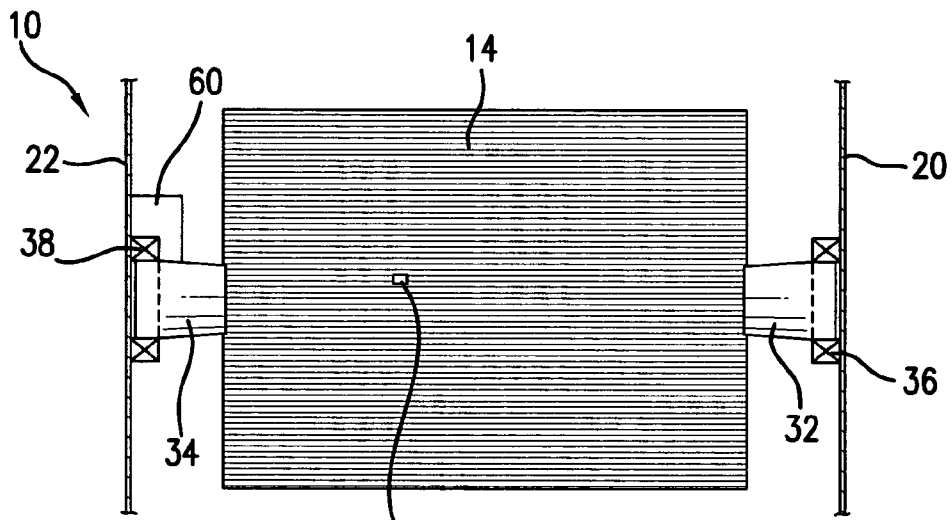
FIG. 3A is cross-sectional view of a dispenser that employs a coreless roll with an RFID tag in accordance with one exemplary embodiment.

With particular reference now to FIG. 3 of the drawings, the dispenser 10 includes a reader or scanner 60 positioned in a non-limiting example on the housing 16 or module (FIG. 7), and by way of another non-limiting example, the core 30 of the roll 14 carries identification in the form of a Radio Frequency Identification Device (RFID), which in this embodiment comprises a passive "smart" chip or tag 62. It will be understood that the reader or scanner 60 may be positioned on any portion of the dispenser, or near the dispenser, which permits it to operate in the manner shown and described herein. Similarly, it will be appreciated that the smart tag 62 may be positioned on any location, or a number of locations, on the sheet material, as shown in FIG. 3A, which illustrates the smart tag 62 embedded in a coreless roll. In addition, more than one smart tag 62 may be used in each sheet material roll 14.

The smart tag 62 contains information relating to the type of sheet material on the roll 14, for example information relating to the absorbency, the basis weight, manufacturer, etc. of the sheet material 12. In use, the scanner 60 interrogates the smart tag 62 with an electronic signal, and the smart tag 62, which includes an internal antenna (not visible), in turn generates and transmits an electromagnetic pulse that is readable by the scanner to identify the type of sheet material on the roll 14. The scanner 60 typically is configured to retrieve information from the smart tag 62 and to decode the information.

RFID smart tag technology is known and understood by those skilled in the art, and a detailed explanation thereof is not necessary for purposes of describing the dispenser and method of the present invention. Generally, conductive or passive smart tags consist of silicon or other semiconductors, a coiled, etched, or stamped antenna, a capacitor, and a substrate on which the components are mounted or embedded. A protective covering typically is used to encapsulate and seal the substrate. Inductive or passive smart tags have been introduced by Motorola under the name BISTATIX®. A detailed description of the BISTATIX® device may be found in U.S. Pat. No. 6,259,367 to Klein, the entire contents of which is incorporated herein by reference. Further information on smart tags and related technology is disclosed in U.S. Pat. No. 6,451,154 to Grabau et al; U.S. Pat. No. 6,354,493 to Mon; U.S. Pat. No. 6,362,738 to Vega; and PCT publication WO 02/48955. Various different RFID tags and scanners are available. RFID tags and scanners suitable for use with the dispenser 10 are available from, for example, Philips Semiconductors of Eindhoven, The Netherlands; Sokymat of Lausanne, Switzerland; Checkpoint Systems Inc. of Miami, Fla.; and Omron Company of Tokyo, Japan.

Alternatively, the smart tags 62 may be an active device. In this configuration, the smart tag 62 includes active transceiving circuitry that has the capability to selectively respond to coded request signals transmitted by a scanner. An active smart tag 62 may include the capability to receive and store additional information beyond the information contained in its fixed code. An active smart tag 62 requires an internal power supply, such as a micro-battery, thin film battery, and so forth (not shown).

The dispenser housing 16 desirably contains at least one battery 64 (see FIGS. 1 and 2) for powering the various electric and electronic components within the dispenser 10. It will be appreciated, however, that more than one, that is, a plurality of batteries may be used. Alternatively, however, the dispenser may be powered by AC or an AC powered transformer adapter (not shown).

Figure 4:
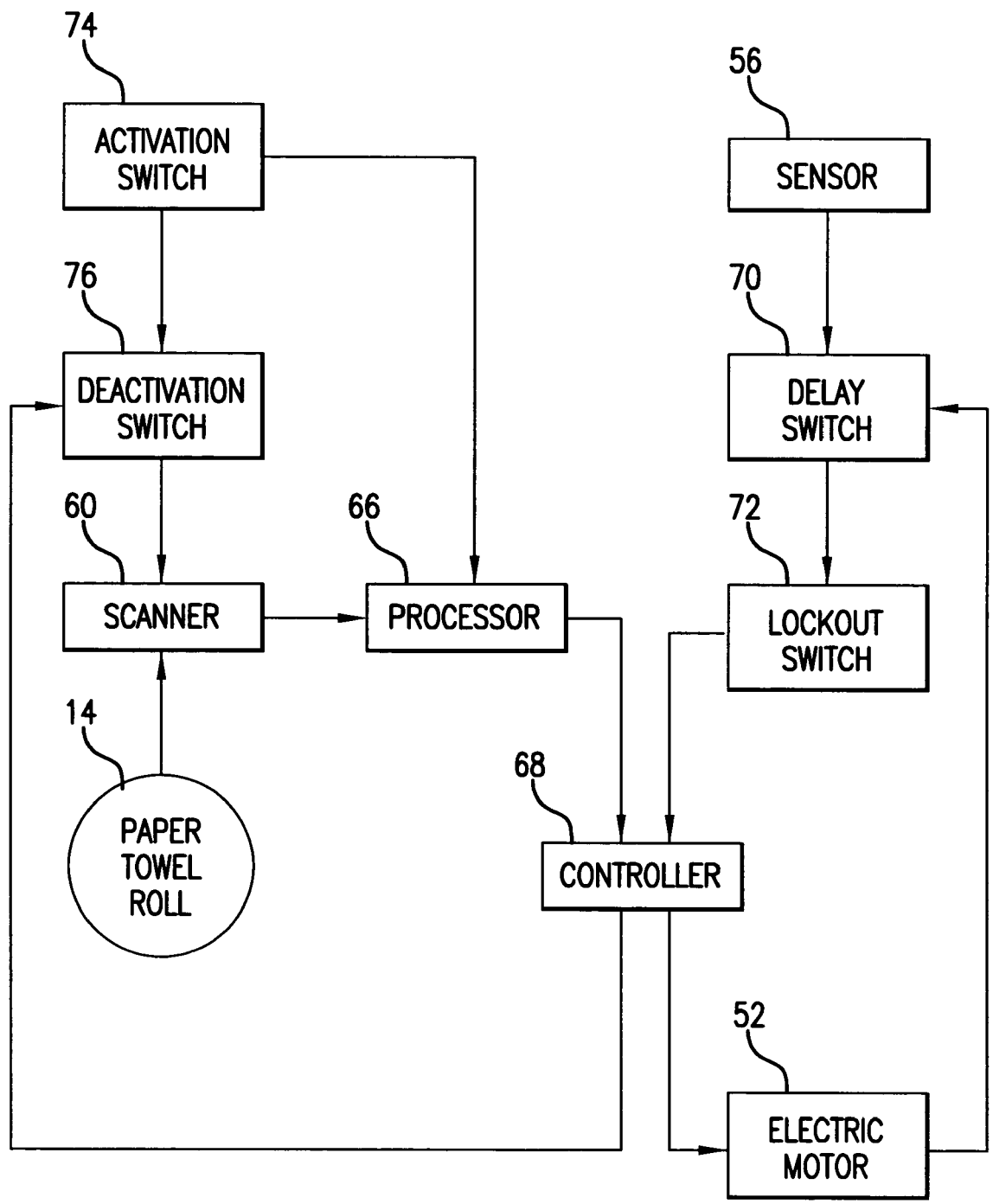
FIG. 4 is a block diagram of the dispenser illustrated in FIG. 1.

Referring now to FIG. 4 of the drawings, the dispenser 10 includes a processor 66 which receives data from the scanner 60 relating to the type of sheet material on the roll 14. The processor 66 contains an algorithm, which in this embodiment is stored in a chip set embedded on a printed circuit board within the dispenser housing 16, and which is used to process the data from the scanner 60 and to generate an output command for a controller 68. The controller in turn controls the operation of the electric motor 52, and hence the dispensing of the sheet material 12, in a manner which is described in more detail below.

A delay switch 70 is desirably provided for ensuring a minimum delay of, for example, but not by way of limitation, three seconds between successive activations of the electric motor 52. This delay is designed to avoid accidental reactivation of the electric motor, and hence unnecessary dispensing of sheet material by a user. The dispenser 10 also desirably includes a lockout switch 72 which opens when the front cover 24 is pivoted away from the closed condition, so as to prevent communication between the sensor 56 and the controller 68. This prevents operation of the electric motor 52 while the dispenser 10 is open. When the front cover 24 is returned to the closed condition, the lockout switch 72 automatically closes to allow operation of the controller 68 and the electric motor 52. In this way, the switch 72 protects an operator from moving components within the housing 16 during servicing or replacement of the roll of sheet material.

An activation switch 74 closes when the front cover 24 is opened, thereby desirably activating the scanner 60. This allows the scanner to read information from the smart tag 62 when the roll 14 is inserted into the dispenser 10. A deactivation switch 76 is also provided for deactivating the scanner 60, to conserve energy, after a predetermined number of revolutions of the drive roller 40, for example 9, or a predetermined number of activations of the electric motor 52, for example 3. It will be understood that any number of revolutions or activations may be set for the deactivation switch.

Alternatively, the dispenser 10 may be equipped with a reset system, e.g., a front cover 24 mounted switch that would trip when the front cover 24 was opened for reloading (not shown). In another alternative, a switch could be provided in connection with a fuel gauge which would trip when the fuel gauge goes to a full zero positions, such as when a product roll is replaced (not shown). Once the system is reset, its reading or sensing circuit would be enabled for a discrete or limited increment, for example, three rotations of the drive roller. After this interval and sensing of the product, the reading or sensing system would shut down until the next reset to conserve power. In still another alternative, a momentary contact switch may be provided in conjunction with, for example, one arm of the roll holder, such that movement of the arm, to load a new roll of sheet material, energizes the reading or sensing circuit.

The operation of the dispenser 10 will now be described with reference to FIG. 4. First, upon opening the front cover 24 of the dispenser housing 16 for the replacement of the sheet material 12, the activation switch 74 desirably closes to activate the scanner 60. The scanner then reads and decodes information relating to the type of sheet material 12 on the replacement roll 14 from the smart tag 62, and transmits data relating to the type of sheet material to the processor 66. The processor receives the data, processes the data, and generates an output command for adjusting the setting of the controller 68, which in turn controls the electric motor 52 so as to dispense a suitable length of sheet material. In this way, the lengths of sheet material 12 metered or dispensed vary according to the type of sheet material 12 detected on the roll 14. For example, the dispenser 10 may be set to dispense three different types of sheet material A, B and C having different degrees of softness and absorbency. If the towel A is the most absorbent and the towel C is the least absorbent, the processor 66 typically is set to generate output commands for adjusting the controller 68 so as to dispense shorter lengths of towel A than towel C. For example, the controller 68 may be adjustable to dispense 12 inches of sheet material A, 14 inches of sheet material B, and 18 inches of sheet material C. In this way, higher quality, more absorbent sheet material is efficiently dispensed without significant waste, while lower quality, less absorbent sheet material is dispensed in sufficiently long lengths to effect proper drying of a user's hands. A desired result is to provide one sheet of material to dry a user's hands; the length provided is meant to provide adequate dryness, based on characteristics of the sheet material, such as absorbency, basis weight, and so forth, so that a user only uses one sheet per hand drying episode.

Once the controller 68 has been set and the front cover 24 has been closed (and desirably locked), sheet material 12 is dispensed to a user upon triggering of the sensor 56. In this regard, when the sensor 56 detects a user's hand, it transmits a signal to the controller 68, through the switches 70 and 72, and the controller then activates the electric motor 52 to dispense the predetermined length of sheet material to the user. In this embodiment of the invention, the controller 68 desirably includes a counter which limits the number of revolutions of the electric motor 52 to effect dispensing of the desired length of sheet material to the user. The delay switch 70 is opened upon deactivation of the electric motor 52 by the controller 68, and this switch remains open for a predetermined time interval, for example, but not by way of limitation, 3 seconds, to block communication between the sensor 56 and the controller 68. In this manner, the delay switch 70 desirably prevents accidental reactivation of the motor 52 by a user removing sheet material 12 from the dispenser 10, and hence unnecessary dispensing of the sheet material. The delay switch 70 also serves to discourage vandals by frustrating bulk dispensing.

When an operator opens the front cover 24 to replace the roll 14, the activation switch 74, by way of non-limiting example, once again activates the scanner 60 so as to allow for the reading of a smart tag on a replacement roll of sheet material inserted into the dispenser 10. In the event that the replacement roll comprises a different sheet material to the previous roll, the processor 66 generates a new output command for adjusting the setting of the controller 68, and hence the length of sheet material to be dispensed by the electric motor 52. Also, as soon as the front cover 24 of the dispenser housing 16 is opened, the lockout switch 72 opens to prevent operation of the electric motor 52, thereby to protect the operator from moving components within the housing 16.

In the event that an unrecognized roll of sheet material ("unrecognized roll", "unrecognized sheet material" and/or "unrecognized paper" as used herein refers to a roll of sheet material which is scanned and either (1) does not send back the expected signal, or (2) does not send back any signal) is loaded into the dispenser 10, and the scanner 60 is unable to read and/or receive information relating to the type of sheet material on the roll, the processor 66 sets the controller 68 to a default setting, which typically is the last stored setting or the maximum setting, which for sheet material A, B and C is, for example, 18 inches. In this way, when the dispenser 10 is used to dispense an unrecognized product, such as a product which the dispenser is not designed to dispense, it either dispenses the product at an arbitrary setting or is adjusted to dispense at the maximum setting for a less absorbent sheet material. Alternatively, the processor 66 may be designed to generate an output command in these instances which blocks operation of the controller 68 entirely so as to prevent operation of the electric motor 52, and hence dispensing of sheet material. Such a function is advantageous because the use of an unrecognized product can result in the jamming of the dispenser, damage to the dispenser, and/or in unsatisfactory dispensing of the product.

Figure 5:
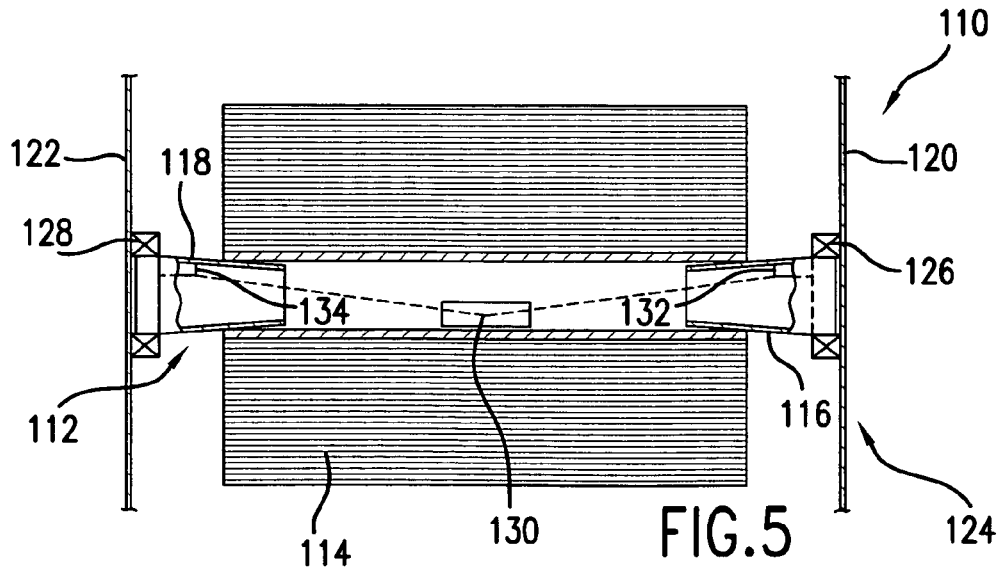
FIG. 5 is a cross-sectional view of a portion of a dispenser according to another exemplary embodiment.

FIG. 5 illustrates a portion of a dispenser 110 according to a second embodiment of the invention. In this embodiment, a support 112 for a sheet material roll 114 includes a pair of mounting hubs 116 and 118 connected to side panels 120 and 122 (or a mounting module, such as that shown in FIG. 7) of a dispenser housing 124 by means of roll holders 126 and 128. As can be seen, the roll 114 carries a reflective label 130, and the support 112 includes an infrared emitter 132 in the mounting hub 116 and an infrared detector 134 in the mounting hub 118. The emitter 132 is arranged to emit angled infrared light into the core of the roll 114, as shown, which upon reflection off the reflective label 130 is detected by the infrared detector 134 to complete an infrared emitter/detector circuit. If an unrecognized product is inserted into the dispenser 110, the infrared emitter/detector circuit will not be completed, and typically the dispenser will default to a setting for a less absorbent sheet material in which a relatively long length of sheet material is dispensed. Recognition of different rolls of sheet materials in this embodiment may be accomplished by adjusting the relative reflectivity of the label and therefore total reflected light for various sheet materials. Apart from the infrared emitter/detector circuit, the dispenser 110 is similar in all other respects to the dispenser 10 described above.

Figure 6:
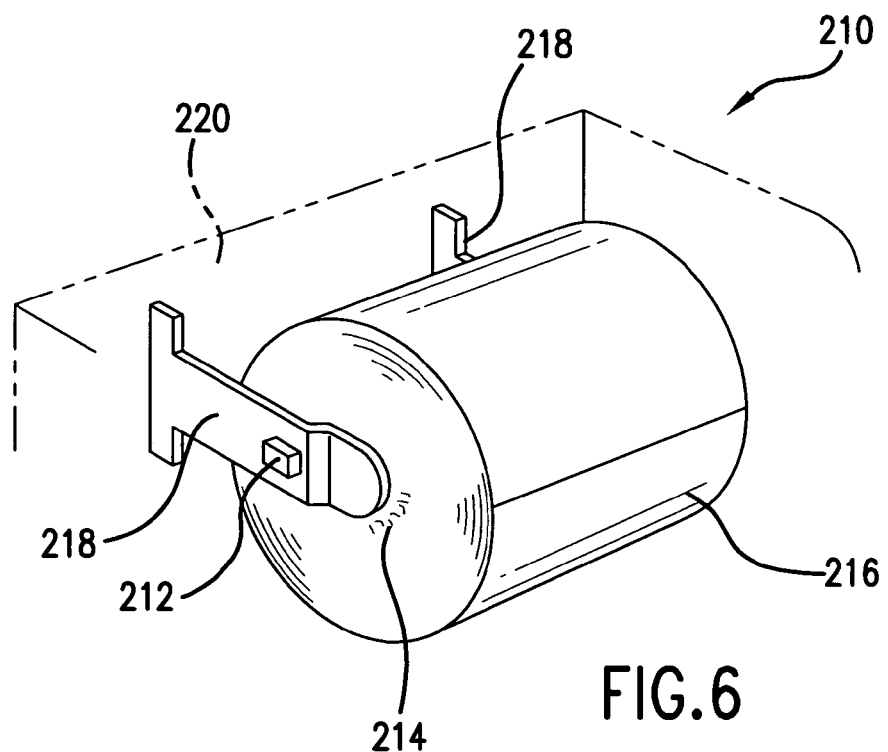
FIG. 6 is a perspective view of a portion of a dispenser according to another exemplary embodiment.

In FIG. 6 of the drawings, a portion of a dispenser 210 according to a third embodiment of the invention is seen to include a reader 212 for reading a logo 214, a bar code or the like which may be typically stamped or ink-jetted onto a side of a sheet material roll 216. It will be appreciated, however, that the bar code may be located anywhere on the roll 216 and/or on any sheet material in the roll 216. The reader 212 in this embodiment is desirably located on a support arm 218 for rotatably supporting the roll 216 within a dispenser housing 220, and is positioned so as to be aligned with the path of travel of the logo 214, although it will be appreciated that, like the bar code, the reader 212 may be positioned anywhere within the dispenser housing 216, so long as it operates to read the bar code as described herein. Accordingly, as the roll 216 rotates on the support arm 218, the logo 214 passes the reader 212 to identify the roll. Once the type of sheet material has been identified, the dispenser 210 is automatically set to dispense a suitable length of the sheet material. If an unrecognized product without the required marking 214 is inserted into the dispenser 210, a default setting for less absorbent sheet material typically will be assumed in which a relatively long length of sheet material is dispensed. Apart from the support arms 218 and the reader 212, the dispenser 210 is similar in all respects to the dispenser 10 described above.

It will be appreciated that the reader 212 may be configured to read and/or recognize a specific label, a specific logo, a magnetic strip, a hologram, and so forth, positioned in any position on any sheet material(s) of the roll 216. Accordingly, the present embodiment is intended as a non-limiting example.

A portion of a dispenser 310 according to a fourth embodiment of the invention is illustrated in FIG. 7 of the drawings. The dispenser 310 is similar in many respects to the dispenser 10, and differs only in that the dispensing mechanisms are mounted in a module 311, having, by way of non-limiting example, side walls 322 and at least a portion of a back wall 318, which is inserted into the dispensing housing 316. Otherwise, the dispenser 310 has the characteristics and operation of dispenser 10, as previously described herein.

Figure 8:
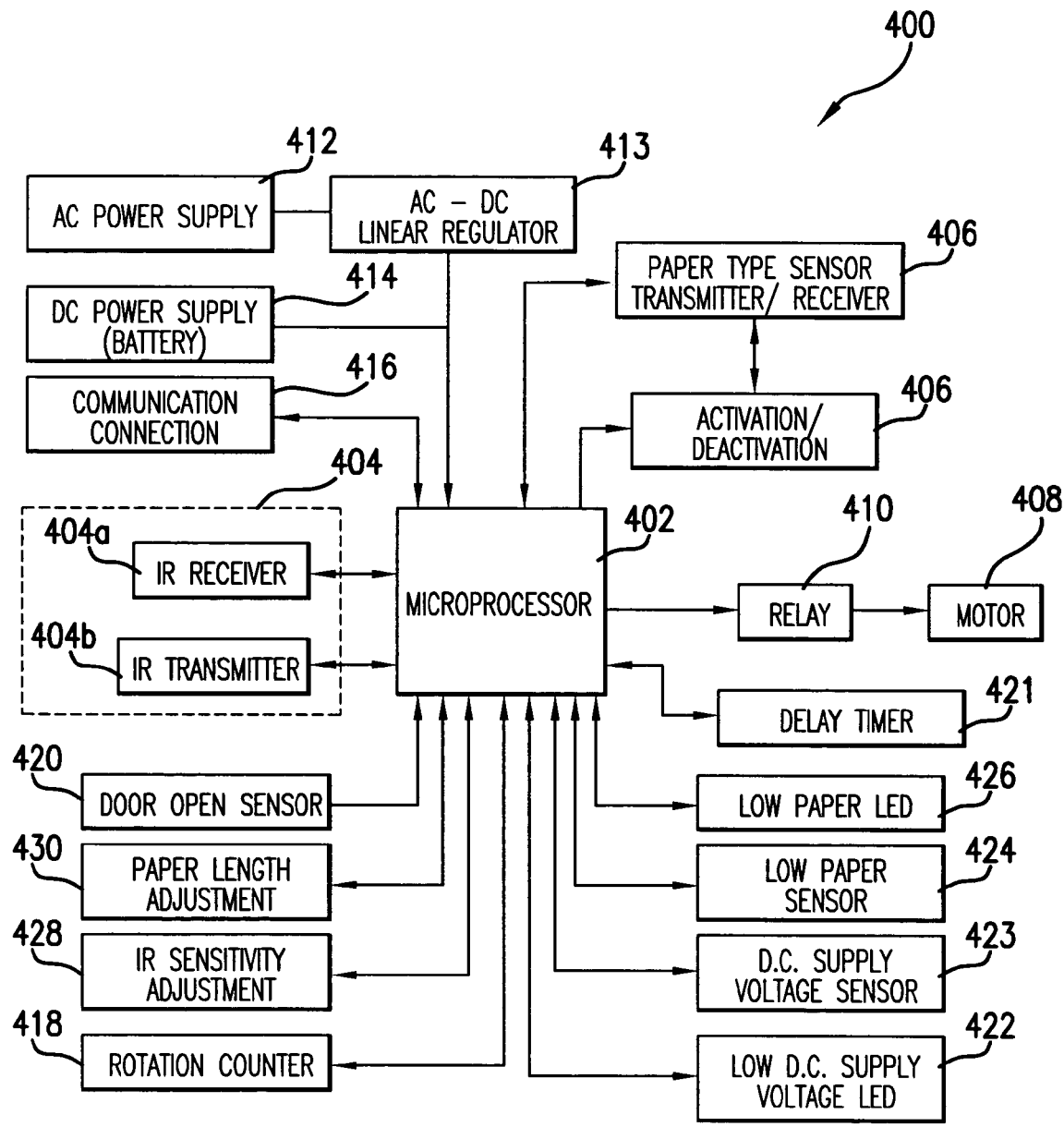
FIG. 8 is a block diagram of yet another exemplary embodiment.

Referring now to FIG. 8, an alternative embodiment of a dispenser 10 controller 400 is presented. Controller 400 includes microprocessor or microcontroller 402 ("microprocessor" and "microcontroller" used interchangeably herein) activation sensor 404 (comprising IR receiver 404a and IR transmitter 404b), paper type sensor 406, motor 408, relay 410 and various sensors, timers, adjustors, and LED indicators (described in more detail later). Controller 400 is powered by either A.C. power source 412 or D.C. power source 414. A communication connection 416 is provided to facilitate programming/reprogramming of microcontroller 402 and/or communication between dispenser 10 and a remote computer.

Microcontroller 402 controls the functioning of dispenser 10 by executing code stored in a program memory. Ideally, microcontroller 402 has onboard program memory and data memory. Such memory is desirably a non-volatile memory; however, volatile memory may be used. One example of a suitable microcontroller is the PIC16F72 microcontroller (PICmicro® family) manufactured by Microchip Technology.

Microcontroller 402, motor 408 as well as individual components of controller 400 are powered by either A.C. power supply 412 or D.C. power supply 414. Desirably, a 120 Volt A.C. line input voltage is reduced to 12 volts using a transformer. The reduced voltage is rectified and feed into linear regulator 413 which maintains the desired D.C. voltage level required by controller 10. One possible embodiment of a D.C. power supply is a battery.

As previously noted for sensor 56, activation sensor 404 is a conventional passive sensor for detecting infrared (IR) radiation comprising a transmitter 404a and receiver 404b. Such passive infrared detectors are known in the art. IR transmitter 404b transmits a periodic (at random intervals or fixed intervals as desired) pulsed IR signal. IR receiver 404a is configured to detect reflected IR signals in the same pattern as the transmitted signal. When such a signal is detected, activation sensor 404 generates an output signal informing microcontroller 402 that sheet material or paper should be dispensed.

Desirably, paper length adjustments and IR sensitivity adjustments are performed automatically over communication connection 416 using a remote computer. It should be noted, however, that dispenser 10 allows for manual paper length adjustments and manual IR sensitivity adjustments using paper length adjustment 430 and IR sensitivity adjustments 428 respectively.

When microcontroller 402 determines that activation sensor 404 has been triggered and that dispenser 10 is ready to dispense paper, microcontroller 402 causes paper to be dispensed from dispenser 10 by engaging relay 410 thereby applying power to electric motor 408. As electric motor 408 turns, paper roll 14 turns and paper is forced out of the front of dispenser 10. As paper is being dispensed, microcontroller 402 monitors rotation counter 418 which outputs a signal for each motor rotation (or paper roll 14 rotation, or fraction thereof). When rotation counter 418 generates a predefined number of rotation signals, microcontroller 402 disengages relay 410 thereby removing power to motor 408. Thus, one of ordinary skill in the art will recognize that the length of paper that is dispensed can be controlled by manipulating the predefined number of rotation signals microcontroller 402 looks for (i.e. the value at which microcontroller 402 turns off motor 408).

Before engaging relay 410, microcontroller 402 checks the status of Delay timer 421. The purpose of delay timer 421 is to prevent consecutive paper dispensing events until a predefined amount of time elapses. Upon disengaging relay 410 after a paper dispensing event, delay timer 421 is activated. While delay timer 421 is active, microcontroller 402 disables relay 410. Delay timer 421 is designed to "time out" after a predefined amount of time. Such functionality can be achieved using a count down timer, a count up timer or any other suitable timing technology. For example, delay timer 421 could be set to "time out" ten seconds after activation. For such a configuration, consecutive paper dispensing events could not occur faster than once every ten seconds.

Before engaging relay 410, microcontroller 402 checks the status of door open sensor 420. When a user opens front cover 24 to replace paper roll 14 or otherwise service dispenser 10, open door sensor 420 asserts a door open signal that is sensed by microcontroller 402. Upon sensing a door open signal, microcontroller 402 disables relay 410 thereby disabling electric motor 408.

Microcontroller 402 monitors the output of sensor 423. D.C. voltage sensor 423 monitors the output voltage level of D.C. power supply 414. If such voltage level drops below a predefined amount, microcontroller 402 asserts a voltage signal to low D.C. supply voltage LED 422. When such a low signal is asserted, LED 422 will emit light informing a user that the D.C. power source (perhaps a battery) is not providing the proper power to controller 400.

Microcontroller 402 also monitors low paper sensor 424. One method of sensing a low paper condition may be accomplished using a mechanical arm that rides on paper roll 14. As paper from paper roll 14 is dispensed from dispenser 10, paper roll 14 shrinks in size. Eventually such mechanical arm will activate low paper sensor 424 and a low paper signal will be asserted. When microcontroller 402 detects a low paper signal, microcontroller 402 asserts a signal to low paper LED 426 and LED 426 will emit light informing a user that the paper source is almost depleted.

Attention is now directed to paper type sensor transmitter/receiver 406. When a user opens front cover 24 to replace paper roll 14 or otherwise service dispenser 10, open door sensor 420 asserts a door open signal that is sensed by microcontroller 402. Microcontroller 402, in turn, activates the transmitter/receiver associated with the paper type sensor transmitter/receiver 406. One possible embodiment of a paper type sensor transmitter/receiver is an RFID based sensor. Ideally, paper roll 14 is associated with an RFID smart tag. For such a configuration, paper type sensor transmitter/receiver 406 transmits an RFID smart tag trigger signal and listens for transmissions from RFID smart tags associated with paper roll 14. At least part of the received smart tag data is stored in a memory associated with microcontroller 402. Such smart tag data ideally comprises paper type identification information. Such information may be used by microcontroller 402 to automatically configured dispenser 10 operation based on the type of paper inserted into dispenser 10.

Figure 12:
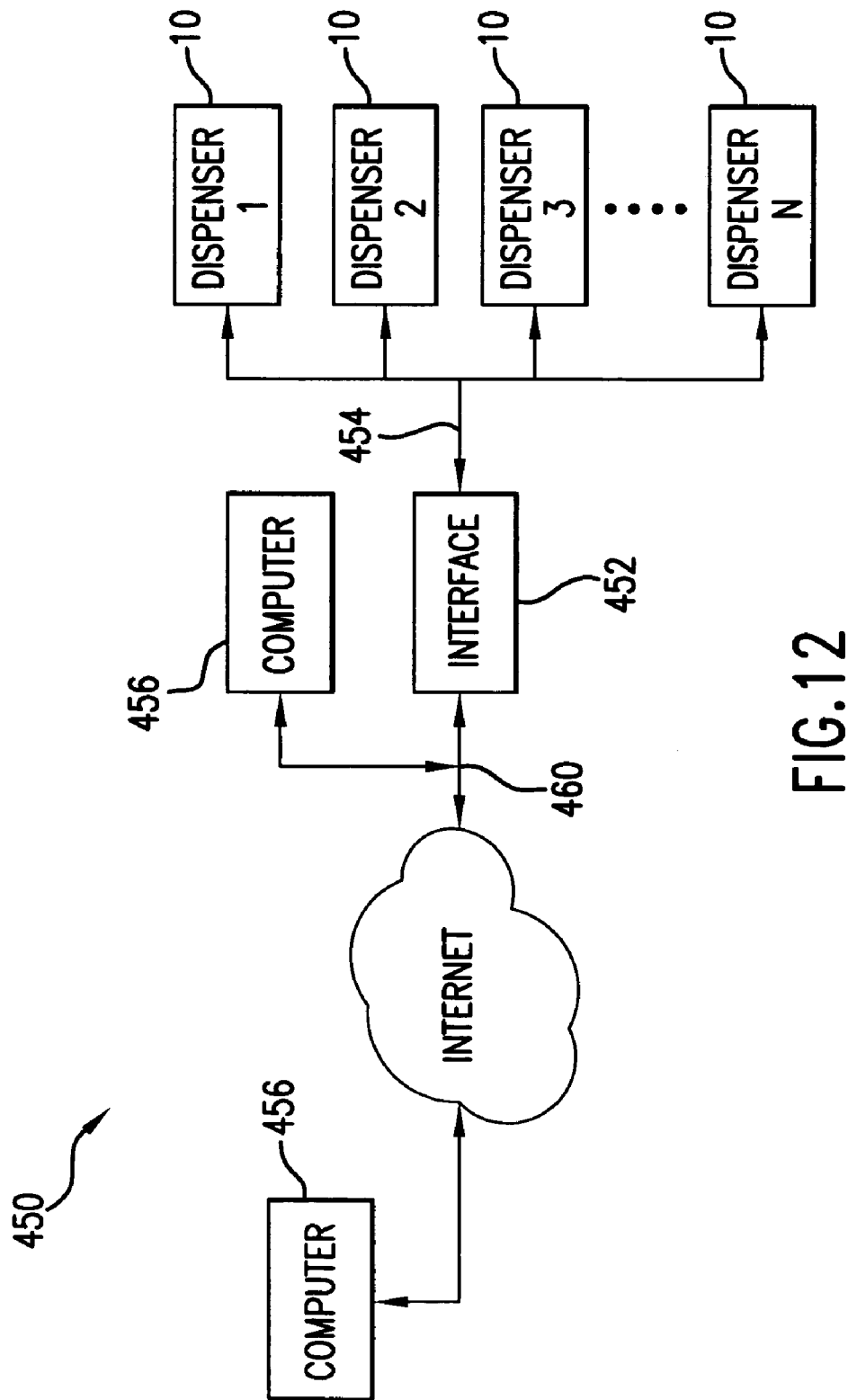
FIG. 12 is a block diagram of still yet another exemplary embodiment.

Now referring to FIG. 12, a network enabled dispenser system 450 is depicted. Multiple dispenser 10 devices are shown all interconnected to remote computer 456 via interface 452 and through wired or wireless communication link 454. Such communication technology is well known in the art and includes Wi-Fi (wireless fidelity) and Bluetooth.

Interface 452 may comprise a gateway for connecting two otherwise incompatible systems or for simply providing a connection between two compatible systems. As used herein, a gateway is an electronic device that connects two otherwise incompatible systems or that simply provides a connection between two compatible systems. Interface 452 may also be incorporated into remote computer 456.

For such a configuration, a TCP/IP protocol suite may be incorporated into Interface 452 providing a gateway between remote computers connected to communications link 454 and dispenser 10 devices which ideally enables continuous remote access to such devices. The gateway may incorporate an HTTP server for accessing data from multiple dispenser 10 devices and for transmission of data to individual dispenser 10 devices.

In the above described system 10 configuration, communications link 460 provides access to a first network (such as the Internet) operating in accordance with a predetermined protocol (TCP/IP is one example). A plurality of dispenser 10 devices may comprise a second network, such as a LAN. A gateway (Interface 452) operatively couples the first network to the second network. Finally, an HTTP server is embedded in either the gateway or the plurality of dispenser devices facilitating the transfer of data between the two networks. With such a configuration, one of ordinary skill in the art will appreciate that individual dispenser 10 devices or groups of dispenser 10 devices may be accessed as if such devices were a web site and their information could be displayed on a web browser. Such technology is fully disclosed by Ardalan et al in U.S. Pat. No. 6,363,057 for use in a system for communicating with electricity meters, which is hereby incorporated by reference for all purposes.

Exemplary algorithms for controlling dispenser 10 are now considered. Such algorithms include a Dispense Paper routine, a Check Dispenser Status routine, and a Paper routine. Ideally, such algorithms, in the form of programming code, would be stored in a nonvolatile memory associated with processor 66 or microcontroller 402. Hereafter, however, processor 66 will be described as executing the disclosed algorithms. Typically, when dispenser 10 is powered up or reset, after performing the necessary startup routines, processor 66 would access and execute such programming code as required. It should be appreciated, however, that such programming code may be executed by any processor associated with dispenser 10.

Figure 9:
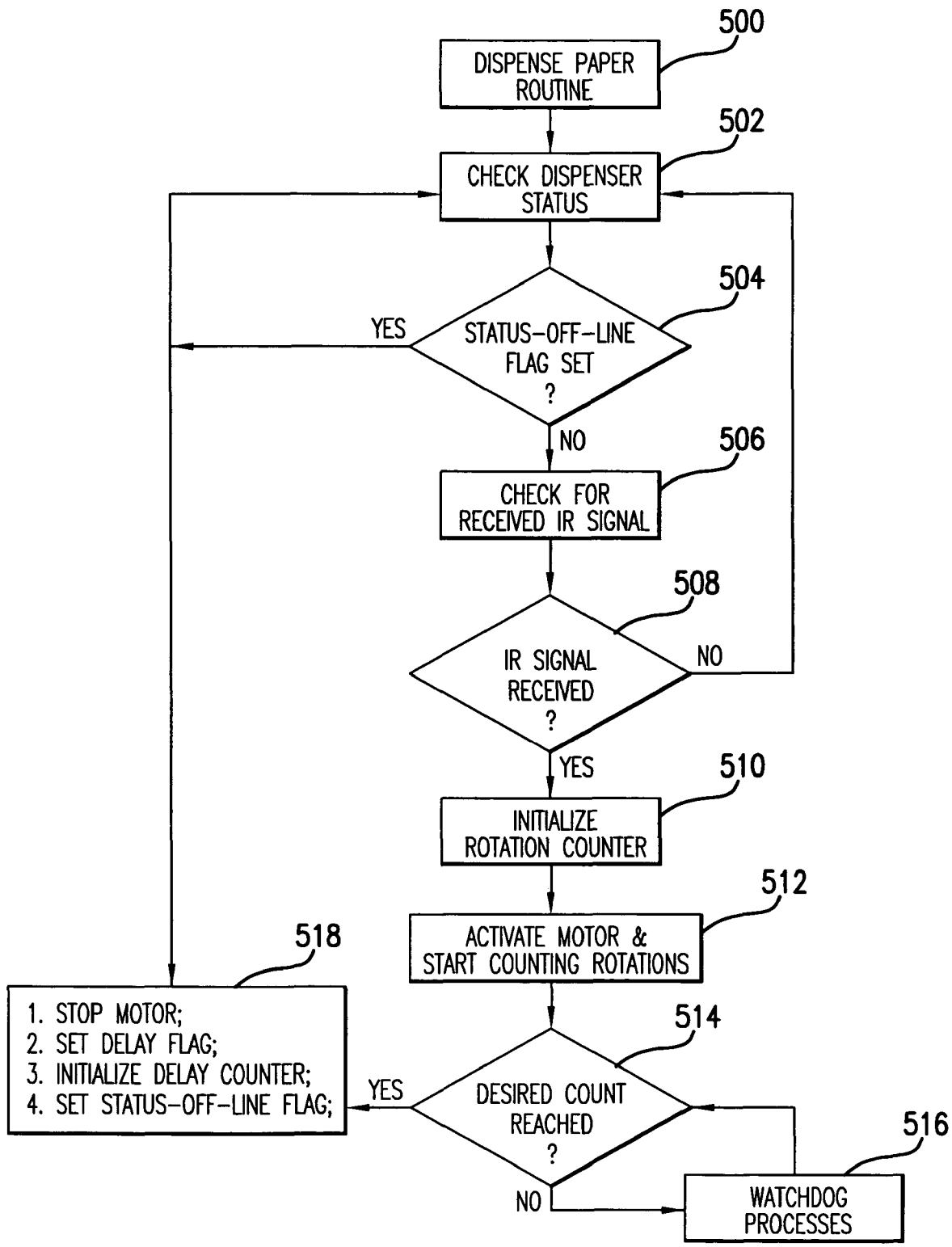
FIG. 9 is a logic chart of a dispense paper routine.

Referring now to FIG. 9, a high level block diagram of an exemplary Dispense Paper routine is presented. Step 500 marks entry into the Dispense Paper routine. At step 502, the status of dispenser 10 is checked by executing exemplary Check Dispenser Status routine which is described in more detail later. Generally speaking, the Check Dispenser Status routine evaluates the state of the various sensors associated with dispenser 10 and "sets" a Status-Off-Line flag if dispenser 10 is not ready to dispense paper or "resets" such Status-Off-Line flag if dispenser 10 is ready to dispense paper. At step 504, the value of the Status-Off-Line flag is examined. If the Status-Off-Line flag is set, dispenser 10 is not ready to dispense paper and program control returns to step 502 and the Check Dispenser Status routine is again executed. Such a loop will continue until the Check Dispenser Status routine determines that dispenser 10 is ready to dispense paper and resets the Status-Off-Line flag.

If at step 504, processor 66 determines that the Status-Off-Line flag is not set (i.e. the Status-Off-Line flag has been reset), program control passes to step 506 where processor 66 checks for a signal indicating that paper should be dispensed. For the disclosed exemplary embodiment, processor 66 checks for a received IR signal having a predefined pattern. If at step 508, the appropriate IR signal has been received, a rotation counter is initialized (step 510) and program control passes to step 512 where electric motor 52 is activated. As electric motor 52 turns, paper towel roll 14 turns and the rotation counter is incremented. At step 514, processor 66 evaluates the rotation counter value to determine if the desired number of rotations has been recorded. If the desired rotation counter value has not been recorded, an optional "watchdog" process may be performed (step 516).

A "watchdog" process is simply a process designed to prevent endless loops. For example, if electric motor 52 has malfunctioned, the desired rotation counter value will not be reached as electric motor 52 will not turn. For such a situation, and without a watchdog process, the processor 66 will be caught in an endless loop where it continuously checks the rotation counter value. If electric motor 52 is consuming power during such a situation, there will be unnecessary power consumption (particularly undesirable for battery power embodiments) and the electrical components that control electric motor 52 will be unnecessarily stressed reducing product life. Exemplary watchdog processes may include checking for paper movement and monitoring elapsed time. Ideally, when an error condition is detected, the watchdog process would disable the motor drive circuits and report the error condition.

After step 516, program control passes back to step 514 and processor 66 again evaluates the status of the rotation counter value. If the desired rotation counter value has been recorded, then program control passes to step 518 where power to electric motor 52 in interrupted, a Delay Flag is set, Delay Counter is initialized, and the Status-Off-Line flag is set. Program control then passes back to step 502 and the Check Dispenser Status routine is executed.

Figure 10:
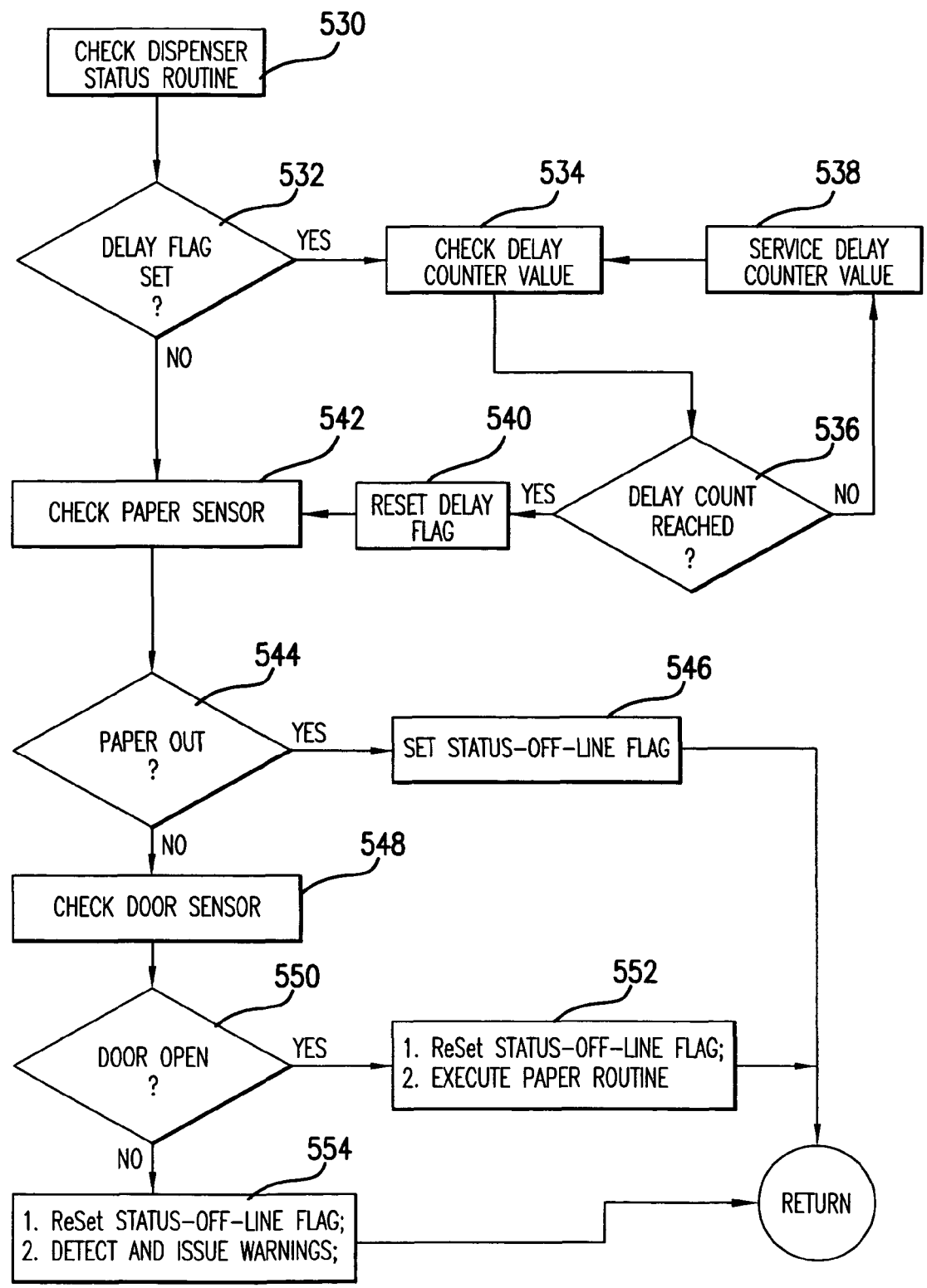
FIG. 10 is a logic chart of a check dispenser status routine.

Referring now to FIG. 10, step 530 marks the entry into an exemplary Check Dispenser Status routine. Upon entry into such routine, the status of the Delay Flag is checked (step 532). If the Delay Flag is set, then program control passes to step 534 and a delay counter value is examined (step 536). If a predefined delay counter value has been reached, then the Delay Flag is reset (step 540) and program control passes to step 542. If, however, such predefined delay counter value has not been reached, the delay counter value is serviced (step 538) and program control returns to step 534. Such delay counter value may be a count down timer, a count up timer, an elapsed time monitor, or any other suitable process for monitoring the passage of time. Exemplary methods of servicing a delay counter value include incrementing a counter value, decrementing a counter value, and updating a time value.

Returning to step 532, if the delay flag is not set, then program control passes to step 542 and the status of the paper sensor is examined. Such a paper sensor ideally determines when dispenser 10 is out of paper. If the paper sensor indicates that the paper supply in dispenser 10 has been depleted, then the Status-Off-Line flag at step 546, is set and program control returns to the calling routine (i.e. the Dispense Paper routine). If at step 544 the paper sensor indicates that the paper supply in dispenser 10 has not been depleted, then program control passes to step 548.

At step 548, a door sensor is evaluated. Such a door sensor ideally determines when a dispenser 10 access means (such as front cover 24) has been opened (perhaps to service dispenser 10). If the door sensor indicates that a monitored access point has been opened, then at step 552, the Status-Off-Line flag is set and a Paper routine (described herein) is executed. When program control returns from the Paper routine, program control returns to the calling routine (i.e. the Dispense Paper routine).

Returning to step 550, if the door senor indicates that no monitored access points have been opened, program controls passes to step 554. At step 554, the Status-Off-Line flag is reset (i.e. dispenser 10 is ready to dispense paper). Optionally, a Detect and Issue Warnings routine (not disclosed) may be executed at this point. Such a routine would check the status of warning sensors, such as low battery, low paper, etc. and issue warnings (such as turning on an LED or transmitting a signal/message to a remote device) when necessary. After resetting the Status-Off-Line flag, program control returns to Dispense Paper routine.

Figure 11:
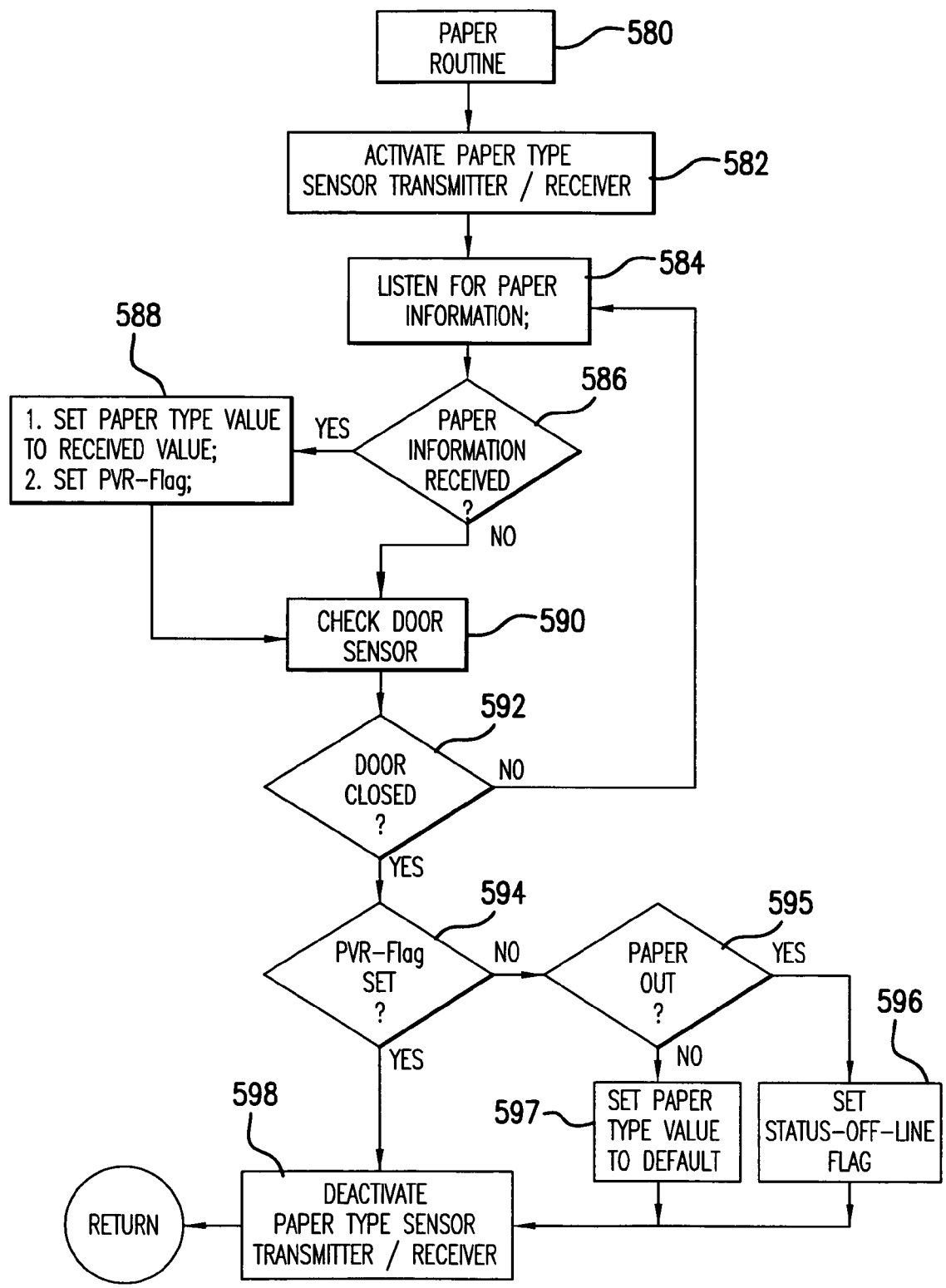
FIG. 11 is a logic chart of a paper routine.

Referring now to FIG. 11, step 580 marks the entry into an exemplary Paper routine. The general purpose of the Paper routine is to automatically detect the type of paper inserted into dispenser 10 and automatically configure dispenser 10 according to predefined paper dispensing parameters associated with the detected paper type. Such dispensing parameters may include the length of the paper to be dispensed and/or the delay between consecutive paper dispensing events. At step 582, processor 66 activates the paper type sensor's transmitter and receiver and listens for paper information (584). For example, if the paper type sensor is an RFID based sensor, an RFID trigger signal is transmitted to trigger RFID smart tag transmissions and a receiver circuit listens for such smart tag transmissions.

Such transmissions ideally comprise paper information associated with the type of paper inserted into dispenser 10. As noted above, such paper information may be used, for example, to determine the length of paper to be dispensed and the delay between dispensing events. Thus, paper information may include two counters values; the rotation counter value (step 512) and the delay counter value (step 534). Alternatively, such paper information may be a simple code that is used to retrieve/access the appropriate paper type information from a memory associated with processor 66. At step 586, if processor 66 determines that valid paper information has been received, then a Paper-Type-Value is set at step 588 consistent with the received paper type information. Additionally at step 588, a PVR-Flag is set (PVR—Paper Value Received). The PVR-Flag is used to document the receiving of valid paper information.

Returning to step 586, if processor 66 determines that no valid paper information has been received, the status of the door sensor is checked (step 590) in the same or similar manner as is done in step 548 (FIG. 10). If at step 592 the door sensor indicates an access point has not closed, program control jumps back to step 584. If, however, the door sensor at step 592 indicates that the access points have been closed, program control passes to step 594 and the status of the PVR-Flag is checked.

If the PVR-Flag has been set, program control passes to step 598. At step 598, the paper type sensor transmitter/receiver may be deactivated and program control returns to the calling routine, in this case, the Check Dispenser Status routine.

If, however, at step 594 the PVR-Flag has not been set, program control passes to step 595. At step 595, the paper sensor is checked in the same or similar manner as in step 542 (FIG. 10). If the paper sensor indicates that there is paper in dispenser 10, then an unknown paper type is deemed to have been inserted into dispenser 10. Under such conditions, the paper type value is set to a default value (step 597). Such a default value may simply be the previous paper type value (i.e. no change in value) or it may be a predefined value specifically used for unknown paper types. Next, at step 598, the paper type sensor transmitter/receiver may be deactivated and program control returns to the calling routine. If, however, at step 595 the paper sensor indicates that there is no paper in dispenser 10, the Status-Off-Line Flag is set at step 596 and program control passes to step 598.

Although the invention has been described above with reference to dispensers which automatically dispense sheet materials with the aid of an electric motor, it will be appreciated that the dispenser could include a manually operated lever or the like for drawing sheet materials off a sheet material roll. In manually operated dispensers with levers, the controller would be arranged to limit the operation of the lever, for example the number of strokes that can be effected or the extent of each stroke (not shown).

An advantage of the dispenser according to the present invention is that it automatically controls the lengths of sheet materials dispensed. Accordingly, there is no need for an operator to adjust the dispenser in order to effect a change in the lengths of sheet materials dispensed. Furthermore, the dispenser is efficient in that it allows for the automatic dispensing of relatively short lengths of more absorbent products, and relatively longer lengths of less absorbent products. Also, the dispenser detects the loading of an unrecognized product, which is usually a less expensive and less absorbent sheet material product, and defaults to a greater length of sheet dispensed. In this way, the dispenser dispenses a single sheet in order to provide user satisfaction in using the single sheet for a hand drying episode, no matter whether a highly absorbent or less absorbent sheet material product is dispensed.

It should be understood that the dispenser of the invention is not limited to the dispensing of one type of sheet material, such as paper towels. On the contrary, the dispenser could also be used to dispense various other types of sheet material, such as, but not by way of limitation, facial sheets, bath tissue sheets, wipers, and so forth.

Figures 13A, 13B:
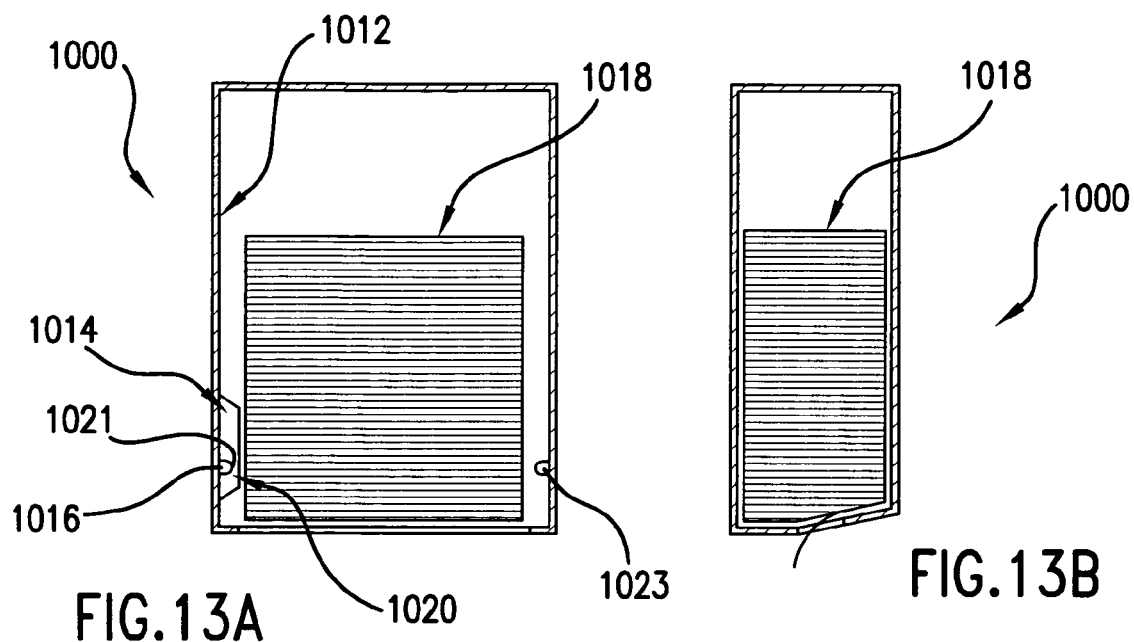
FIG. 13A is a cross-sectional front view of a folded towel dispenser that shows the position of a stack of paper towels and a dispenser sensor unit in accordance with an exemplary embodiment.
FIG. 13B is a cross-sectional side view of the dispenser of FIG. 13A.

FIGS. 13A and 13B of the drawings illustrate a dispenser 1000 for dispensing folded sheet material, such as folded paper towels, folded bath tissue, folded facial tissue, and so forth. FIG. 13A is a front elevation view and FIG. 13B is a side elevation view of the dispenser 1000. A dispenser sensor unit (DSU) 1014 is carried by the inner sidewall 1012 of the dispenser 1000. The DSU 1014 may be used for detecting when refill of the dispenser 1000 is needed. The DSU 1014 uses an infrared sensor 1016 to detect when a paper stack 1018 falls below a low paper point 1020. A narrow beam of infrared light is sent from an emitter 1021 and is picked up by an adjacent detector 1023. When the top of the paper stack 1018 lies above the infrared sensor 1016, the detector 1023 does not pick up infrared light. When the top of the paper stack 1018 lies below the infrared sensor 1016, light from the emitter 1021 is visible to the detector 1023.

The DSU 1014 may be fitted at different positions within the dispenser 1000 so as to accommodate various low product positions. It is to be understood, however, that other position detection mechanisms, such as capacitive, ultrasonic and/or a mechanical lever may be used within the invention. Capacitive proximity sensors produce an electrostatic field that can sense paper and other non-metallic objects as well as metallic objects. Ultrasonic proximity sensors use a transducer to send and receive high frequency sound signals. The reflected sound has a shorter path when the paper is in proximity to the sensor. A mechanical lever can be attached directly or indirectly to an electrical switch. A lever in contact with the paper stack 1018 indicates that there is an acceptable amount of paper remaining, and when the lever is not in contact with the paper stack 1018 the DSU 1014 indicates the paper level is low. Additionally, the DSU 1014 may employ an infrared sensor that is configured differently than the infrared sensor 1016 previously described.

Figure 14:
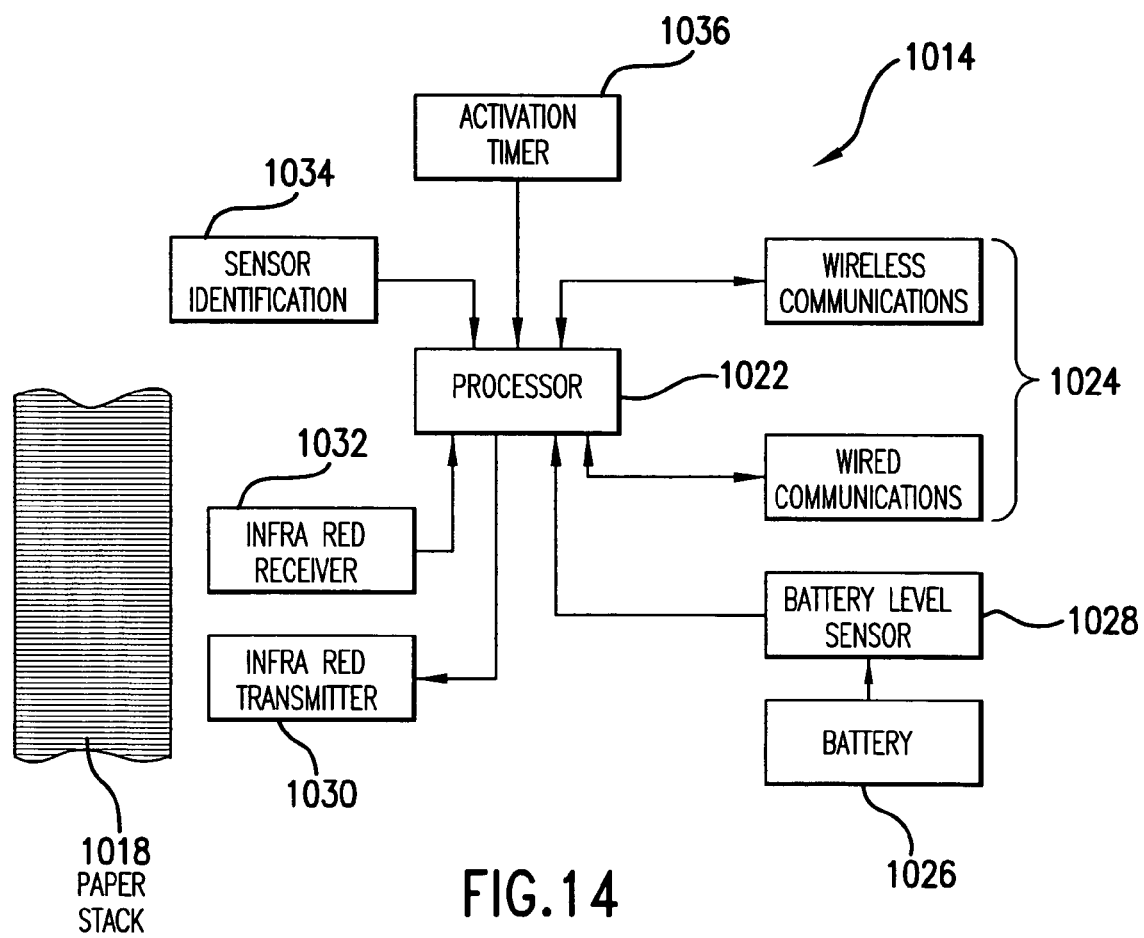
FIG. 14 is a schematic view of the internal arrangement of a dispenser sensor unit as employed in the dispenser of FIG. 13A and FIG. 13B.

FIG. 14 shows the internal arrangement of the DSU 1014 in accordance with one exemplary embodiment. The DSU 1014 includes a processor 1022. The processor 1022 is connected to communications electronics 1024 that allows the DSU 1014 to communicate externally either by wires or wireless. The communication electronics 1024 may include either a transmitter or a transceiver. Additionally, in accordance with certain exemplary embodiments bi-directional communications may be employed. Wireless communications may be based upon one or more license exempt standards including but not limited to IEEE 802.15.4 at 2.4 GHz or 915 MHz in compliance with the requirements of FCC Part 15. A wired arrangement may be based upon an electrical bus standard including but not limited to EIA RS485.

The DSU 1014 may contain a battery 1026 in order to provide power, and the DSU 1014 may include a battery level sensor 1028 to monitor the battery 1026 in order to determine when a battery change out is required. The battery level sensor 1028 may take the form of a simple voltage reference. Alternatively the DSU 1014 may be powered by an appropriate external power supply, or in the case of wired configuration, the DSU 1014 may be powered from a communications bus. The DSU 1014 may contain an infrared transmitter 1030 and an infrared receiver 1032 in communication with the processor 1022. The infrared transmitter 1030 and the infrared receiver 1032 make up, in effect, an infrared transceiver. The DSU 1014 may include a unique identifier 1034. The unique identifier 1034 is used within the overall system to locate each particular DSU 1014. The processor 1022 may be activated intermittently through an activation timer 1036 as is commonly known to one having ordinary skill in the art.

Figure 15:
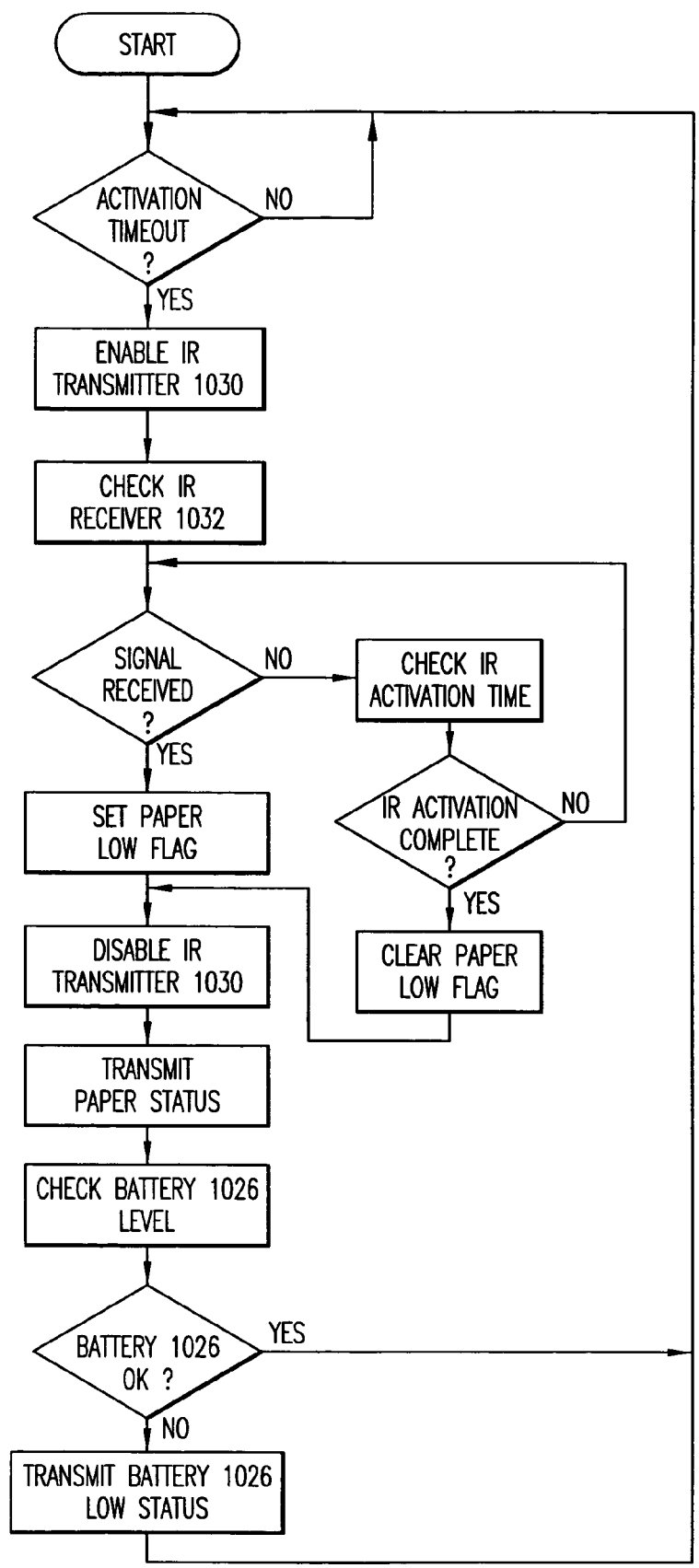
FIG. 15 is a flow chart of the operation of the dispenser sensor unit as employed in the dispenser of FIG. 13A and FIG. 13B.

The operation of an exemplary embodiment of the DSU 1014 is shown in FIG. 15 of the drawings. The processor 1022 contains an algorithm that may be stored in a chip set embedded on a printed circuit board within the DSU 1014 that is used to control and process data for the various elements of the DSU 1014. The DSU 1014 is normally in a low power state to conserve battery power. The infrared transmitter 1030 is enabled for a specified time and the signal received from the infrared receiver 1032 is checked.

A low paper flag is generated if the infrared receiver 1032 detects infrared light from the infrared transmitter 1030. At the end of the infrared enable period the infrared transmitter 1030 is disabled. A paper low flag is reset if the infrared receiver 1032 does not detect infrared light from the infrared transmitter 1030. The status of the paper low flag is then transmitted using the communications facility. The battery 1026 level is also checked after each DSU 1014 activation. If the battery 1026 level is low this status is transmitted using the communications facility. After the activation cycle is complete the DSU 1014 is placed into a low power state and once again waits for the activation timer to activate the processor 1022.

Figure 16:
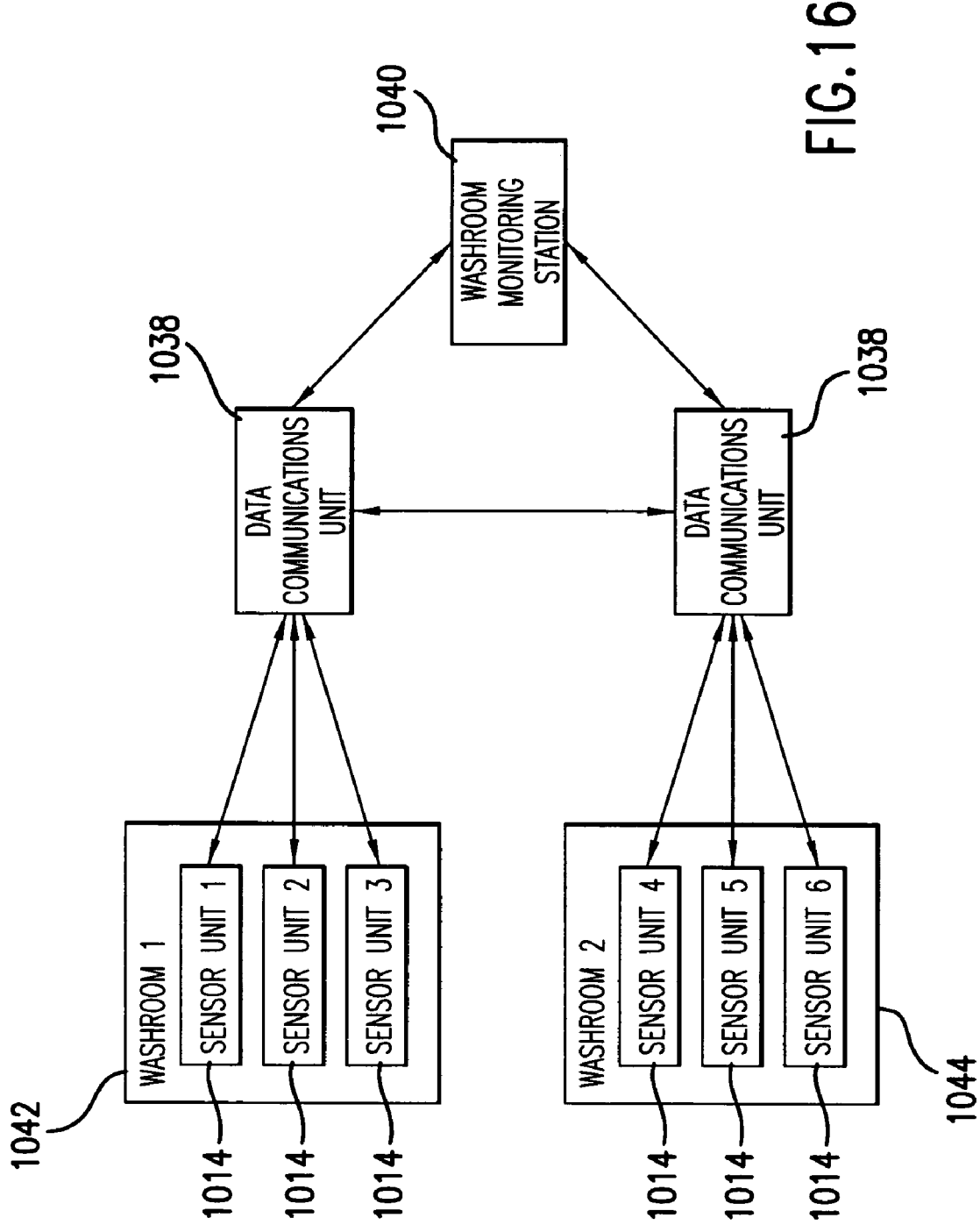
FIG. 16 is a schematic view of the logical relationship between dispenser sensor units, data communication units, and a washroom monitoring station in accordance with an exemplary embodiment.

FIG. 16 is a schematic view of a system including a plurality of DSUs 1014, data communication units (DCUs) 1038, and a washroom monitoring station (WMS) 1040. Uniquely identified DSUs 1038 may be located within various types of washroom dispensers. The dispensers are placed within a first washroom 1042 and a second washroom 1014. Each of the six DSUs 1014 as shown in FIG. 16 communicate with either one of a pair of DCUs 1038. Typically the DSUs 1014 within one washroom 1042, 1044 will communicate with the same DCU. It is to be understood, however, that this arrangement may depend upon the proximity of the DCU 1038 to the DSU 1014, particularly for wireless communications. Other arrangements are possible such that a washroom may span across one or more DCUs 1038. Alternatively, a number of washrooms may be in communication with a single DCU 1038 in accordance with various exemplary embodiments.

The DCUs 1038 may intercommunicate using a standard communications mechanism as is commonly known to one having ordinary skill in the art. The system can be monitored from the washroom monitoring station (WMS) 1040. The WMS 1040 is in communication with the DCUs 1038. The WMS 1040 displays information regarding the status of each DSU 1014 and DCU 1038, including but not limited to product low status, battery 1026 status and communications integrity. The WMS 1040 may be a dedicated application running on a personal computer (PC) with functions including, but not limited to, printing reports and exporting data in various formats. The WMS 1040 may also be based around a PC running a web browser where each DCU 1038 in the system serves web pages containing information on DSUs 1014 and DCUs 1038 in the system. In addition, all or part of the functions of the WMS 1040 may be included within a dedicated display unit.

Figure 17:
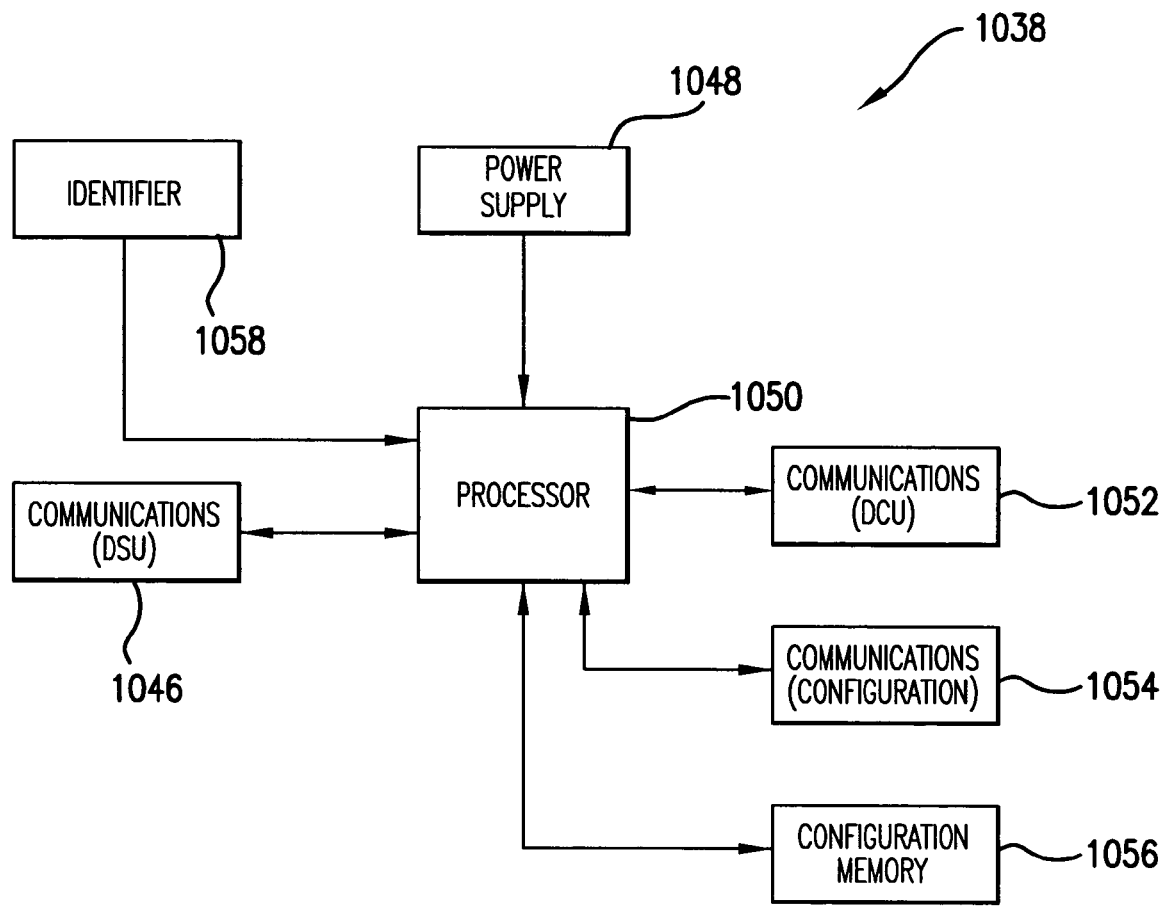
FIG. 17 is a schematic view of the internal arrangement of a data communications unit in accordance with an exemplary embodiment.

FIG. 17 of the drawings shows one exemplary embodiment of the internal arrangement of the DCU 1038. The electronics of the DCU 1038 may be powered from a suitable power supply 1048. The DCU 1038 includes a processor 1050 that is connected to three communications elements. The processor 1050 contains an algorithm, which in this embodiment is stored in a chip set embedded on a printed circuit board within the DSU 1014, and which is used to control and process data for the various elements of the DSU 1014. The first communication element 1046 is dedicated to communications with DSUs 1014. The communication element 1046 is a transceiver with wired and wireless capability. The standards adopted for the communications element 1046 is matched to the DSU 1014 communications.

The second communication element 1052 may be dedicated to communications with other DCUs 1038 and WMS 1040. The second communication element 1052 is based upon one or more standards including but not limited to IEEE 802.3i (Ethernet 10BaseT) and IEEE 802.11b (11 Mhz WiFi). In this manner, the DCUs 1038 can be connected using standard networking technologies. The DCU 1038 communications run over a suitable network protocol such as TCP/IP. This allows an HTTP web server to be incorporated within each DCU 1038 so that web pages can be served to a web browser located on the network. The DCU 1038 may be connected to a local area network (LAN) through a standard RJ45 socket. Use of the web browser will allow a user to navigate through information contained in the DCU 1038. To ensure that only authorized users can access information in the DCU 1038, password protection may be implemented in the web server. A PDA may be used so as to allow for flexibility regarding locations in which a user may access information in the DCU.

The third communications element 1054 is dedicated to communications allowing the DCU 1038 to be configured. The third communications element 1054 is based upon one or more standards including but not limited to EIA RS232. Through this communications element 1054 the DCU 1038 can be configured for operation. A non-volatile memory 1056 is used to store configuration information so that the DCU 1038 retains configuration and other useful information during power down. The DCU 1038 has a unique identifier 1058 so as to allow for the DCU 1038 to be located and identified.

Figure 18A:
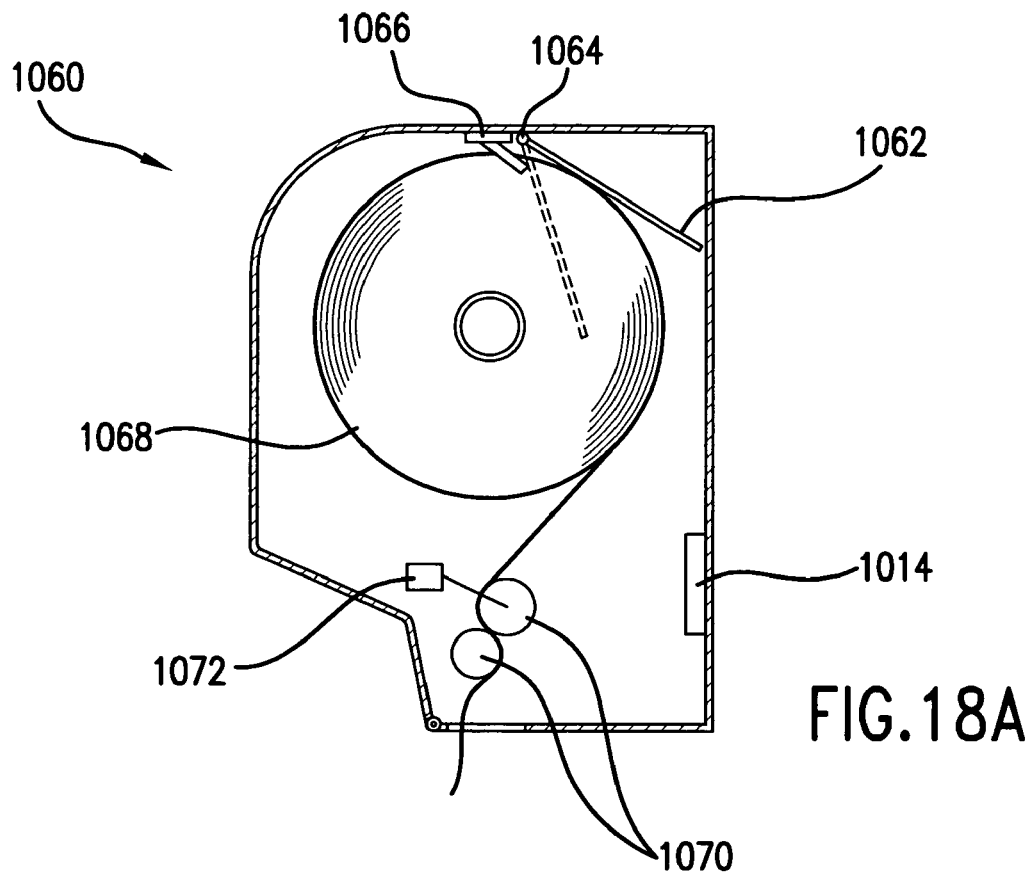
FIG. 18A is a cross-sectional side view of an automatic roll towel dispenser that incorporates a dispenser sensor unit in accordance with one exemplary embodiment.

FIG. 18A of the drawings shows an automatic roll towel dispenser 1060. It is to be understood, however, that various other types of dispensers such as folded products or individually stacked products such as diapers and feminine products may be used in accordance with other exemplary embodiments of the present invention. For instance, dispensers described in co-pending and commonly owned U.S. patent application Ser. No. 10/750,238 entitled "Dispenser with Electronic Sensing Device to Control Delivered Sheet Length" filed Dec. 31, 2003 may be used. U.S. patent application Ser. No. 10/750,238 is incorporated by reference herein in its entirety for all purposes.

Referring back to FIG. 18A a mechanical lever 1062 arranged on a pivot 1064 may be used to determine when a product low condition has been reached. When a full paper roll 1068 is placed into the dispenser 1060 the lever 1062 reaches its furthest extent. A micro-switch 1066 or other suitable device located near the pivot 1064 may be used to send a signal to a dispenser sensor unit (DSU) 1014 through either a hard-wired connection or wirelessly. Other devices commonly known in the art such as, but not limited to an analog device can be used to sense the full range of the paper roll 1068 size to serve as a "fuel gauge." In this instance, the amount of product remaining may be reported as 10%, 20%, 30%, etc. Any sensor commonly known in the art may be used such as a rotation sensor or infrared sensors. Another example of a device that may be used to sense the fullness of the paper roll 1068 size is a variable resistor. When the lever 1062 reaches the point at which the micro-switch 1066 is thrown, the DSU 1014 may signal a low product condition. It is to be understood, however, that other mechanisms of sensing product low may be used such as the infrared method described previously. Additionally, the DSU 1014 may include only electrical components in certain embodiments but may alternatively include both electrical and mechanical components such as the micro-switch 1066, pivot 1064 and lever 1062 in other embodiments.

Figure 18B:
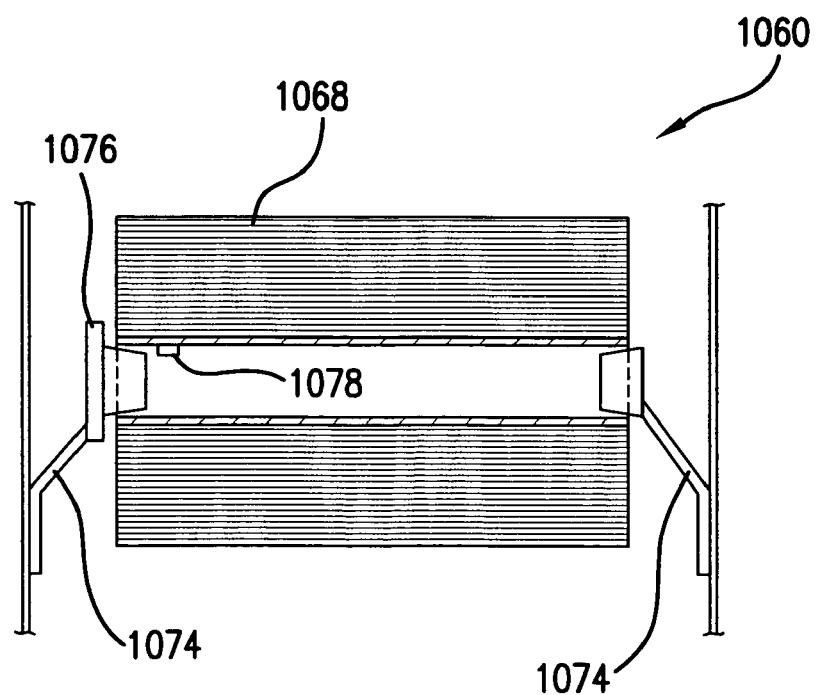
FIG. 18B is a front view of a portion of the automatic roll towel dispenser shown in FIG. 18A.
Figure 33:
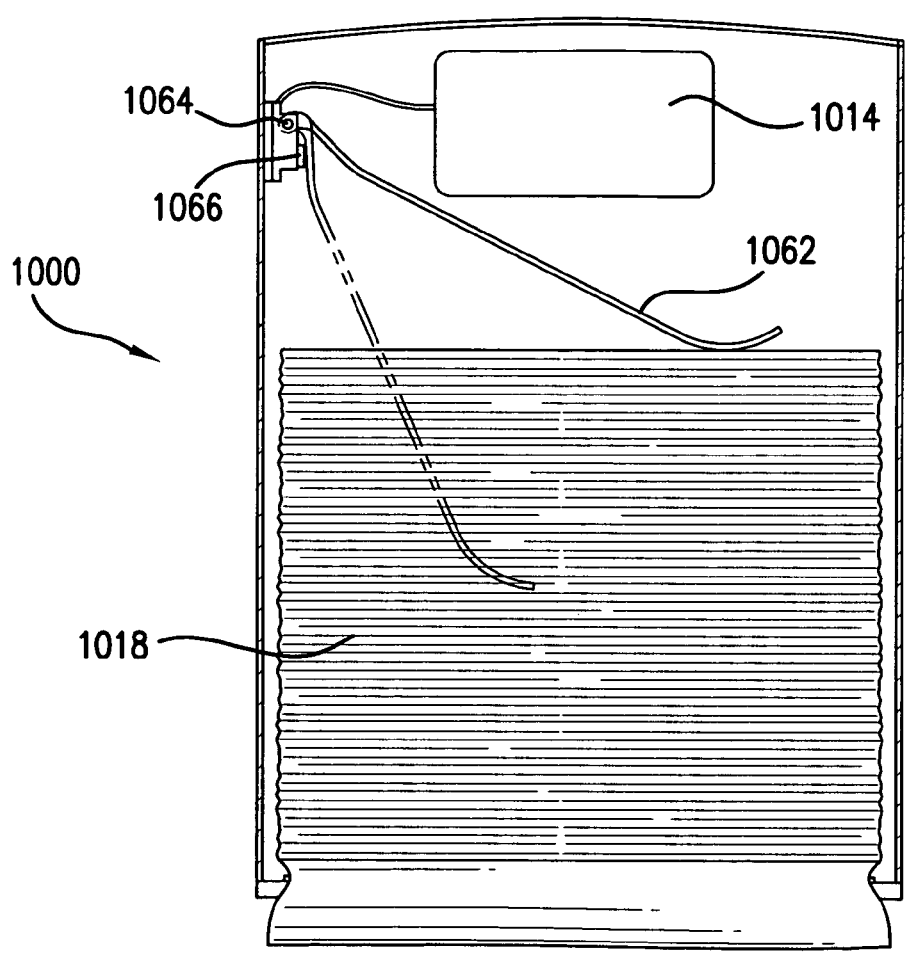
FIG. 33 is a front view of a portion of a dispenser capable of detecting a product low condition of a paper stack in accordance with one exemplary embodiment.

FIG. 33 shows a dispenser 1000 in which a paper stack 1018' is used instead of the paper roll 1068 of FIGS. 18A and 18B. The mechanical lever 1062 may be arranged on pivot 1064 and may be used to determine when a product low condition has been reached in a manner similar to that of FIGS. 18A and 18B. Here, however, mechanical lever 1062 contacts the upper portion of paper stack 1018.

Referring generally back to FIG. 18A, in accordance with another exemplary embodiment, the system can also signal product usage for a broad range of product dispensers. This is described in detail in U.S. Pat. Nos. 6,360,181 and 6,411,920, which are incorporated by reference in their entirety herein for all purposes. As paper is dispensed automatically, a rotation sensor 1072 attached to one of the pinch rollers 1070 determines how much paper is dispensed. After product has been dispensed, the paper length passed through the pinch rollers 1070 is signaled to the DCU 1038. The rotation sensor 1072 may be a rotary encoder type, its output being connected to the DSU 1014. It is to be understood, however, that any other sensor type capable of detecting rotary movement may be used with the present invention such as a moving magnet and reed switch combination, a photo encoder, or a photo interrupter with slotted wheel. Information on product usage collected from respective dispensers and associated products can be processed and reported through the WMS 1040. The capability of detecting a product low condition provides a method for replenishing an inventory of product. Through a database the system keeps a record of the number of times that a low supply level for the respective dispensers and associated products has been alerted. The user may be responsible for entering product type for a respective dispenser manually. A method of recording the current inventory and then automatically reordering and billing a customer for the amount of product consumed is provided as another aspect of the invention.

In accordance with another exemplary embodiment, the DSU 1014 may determine the type of product in use by interfacing directly or indirectly with the product recognition part of the dispenser 1060. Referring to FIG. 18B, the position of a paper roll 1068 within the dispenser 1060 is shown. The paper roll 1068 is suspended between two spring arms 1074 that are attached to the side wall of the dispenser 1060. An RFID reader 1076 is located on one of the spring arms 1074 and is in communication with a DSU 1014. Embedded within the paper roll 1068 is an RFID tag 1078 positioned in proximity to the RFID reader 1076.

The RFID tag 1078 contains information relating to the type of paper roll 1068. In use the DSU 1014 reads the contents of the RFID tag 1078 and signals the product type information to the DCU 1038. If no RFID tag 1078 is discovered or if an unrecognized RFID tag 1078 is identified, this status is signaled to the DCU 1038. The DCU 1038 has the option of enabling the low product reporting function if "recognized paper" is used. RFID technology is known and understood by those skilled in the art, and a detailed explanation thereof is not necessary for purposes of describing the present invention. Additionally, it is to be understood that the present invention includes exemplary embodiments where other mechanisms are used to identify the product. For instance, a bar code reader or other identification mechanism such as a label, logo, magnetic strip, "smart" tag, hologram or luminescence/fluorescence may be used in accordance with other exemplary embodiments. The DSU 1014 may include the RFID reader 1076 or bar code reader or other mechanism, or the RFID reader 1076 or bar code reader or other mechanism may be separate components from the DSU 1014 that communicate with the DSU 1014.

The DSU 1014 may employ a direct connection in that the electronics and software associated with the DSU 1014 are built into or subsumed within the electronics of the dispenser 1060. Alternatively, an indirect connection may be employed such that a separate electrical path is made between the DSU 1014 and the dispenser 1060 electronics such as digital inputs and outputs or a serial data link.

In another exemplary embodiment, with reference to FIG. 18A, the DSU 1014 can signal a paper blockage or jam in conjunction with the mechanism for detecting product low and the mechanism for detecting product usage. When the mechanism for dispensing paper is activated, this action can be detected by the DSU 1014 by interfacing directly or indirectly to the paper activation sensor of the dispenser as described above and as described in U.S. patent application Ser. No. 10/750,238. If the DSU 1014 detects that no paper is dispensed and that there is paper remaining on the paper roll 1068 then a paper jam can be signaled to the DCU 1038. This signal can be used to indicate that the dispenser 1060 needs to be serviced.

Figure 19A:
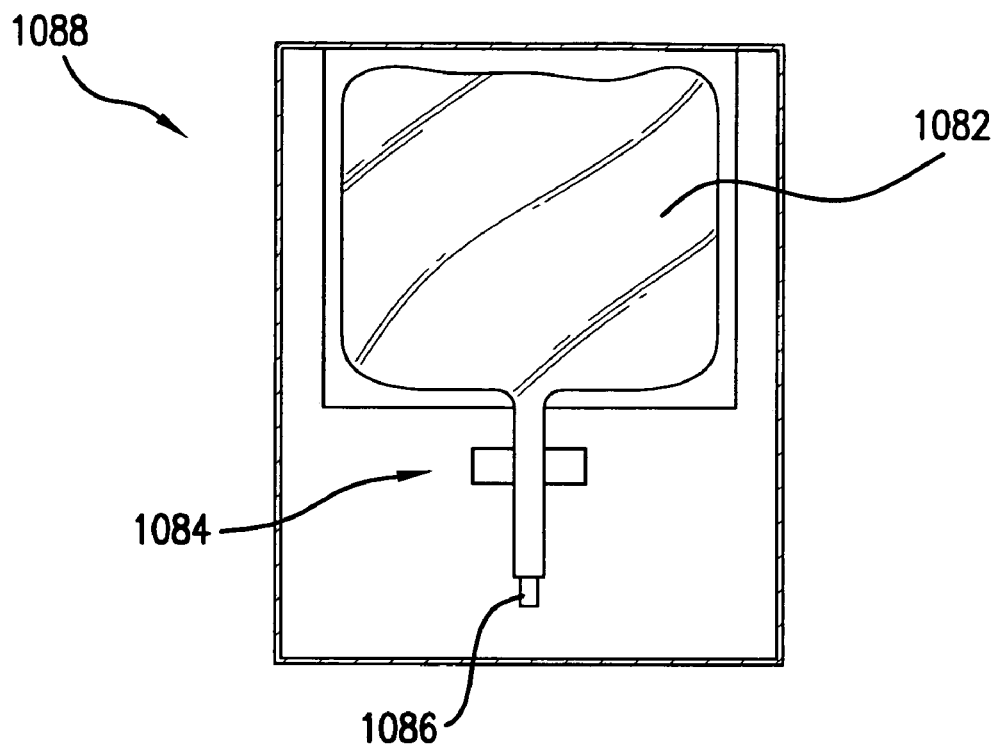
FIG. 19A is a front view of an automatic soap dispenser employing a dispenser sensor unit in accordance with an exemplary embodiment.
Figure 19B:
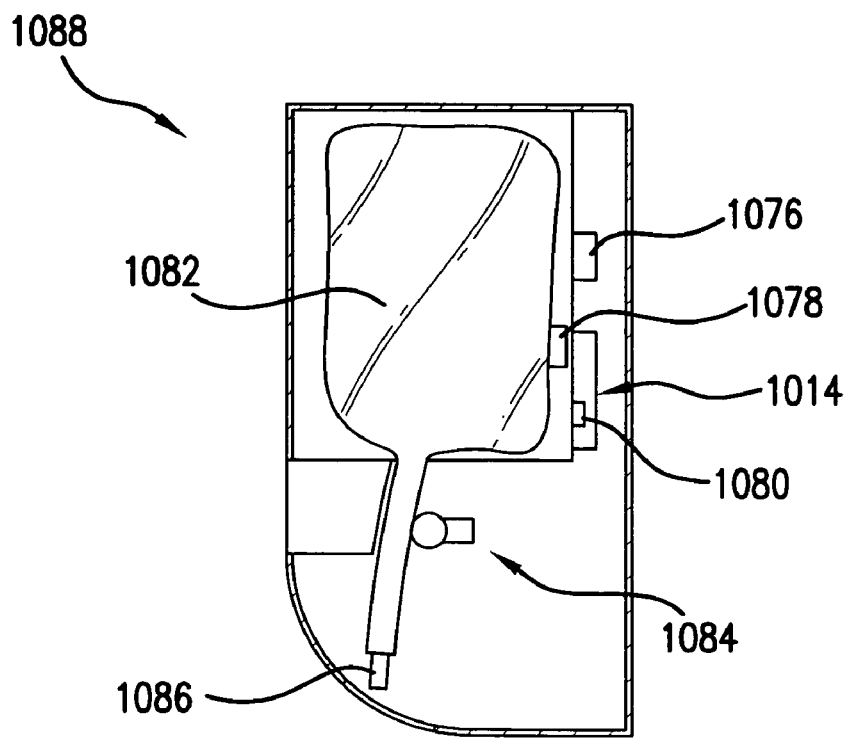
FIG. 19B is a side view of the automatic soap dispenser in FIG. 19A.

FIGS. 19A and 19B of the drawings show similar embodiments as described above for an automatic roll towel dispenser 1060 but in relation to an automatic soap dispenser 1088 such as that described in U.S. Pat. No. 6,209,752, which is incorporated by reference in its entirety herein for all purposes. Soap may be automatically dispensed from a soap refill cartridge 1082 out of a soap nozzle 1086 by a soap dispensing mechanism 1084. In this embodiment, the DSU 1014 also contains an electrostatic proximity sensor 1080 to detect the presence of soap in the soap refill cartridge 1082.

The electrostatic proximity sensor 1080 uses the difference in dielectric strength between a full and a partially empty soap refill cartridge 1082 to determine a product low condition. Other sensor types capable of detecting the presence of product such as infrared sensors, mechanical levers and mechanical strain gauges are appropriate and may be used for both automatic or manual soap dispensers 1088 or other dispensers 1060. The proximity sensor 1080 is positioned within the dispenser 1088 at a point such that it can detect when soap has reached the pre determined low point. In use the DSU 1014 periodically checks the proximity sensor 1080 and at a predefined point signals to the DCU 1038 when a low product condition exists. In another embodiment, the DSU 1014 interfaces directly or indirectly to the electronics responsible for operating the dispensing of soap. The DSU 1014 can then signal product usage to the DCU 1038. One example of a liquid product dispenser that may be used to determine usage through weighing or shot size may be found in U.S. Pat. No. 6,411,920 that is incorporated by reference herein in its entirety for all purposes.

In a further embodiment, the DSU 1014 contains an RFID reader or scanner 1076 positioned close to that part of the dispenser 1088 carrying the soap refill cartridge 1082. The soap refill cartridge 1082 carries identification in the form of an RFID tag 1078 and at a position such that the RFID reader 1076 can read the RFID tag 1078. The RFID tag 1078 contains information relating to the type of soap product contained within the soap refill cartridge 1082. In use, the DSU 1014 reads the contents of the RFID tag 1078 and signals this information to the DCU 1038. If no tag is discovered or if an unrecognized RFID tag 1078 is identified, this status is also transmitted to the DCU 1038. The DCU 1038 has the option of disabling the low product reporting function if "unrecognized soap" is used.

Various other exemplary embodiments also have the ability to enable a product low display feature or other higher features if the system does not recognize products. The system will still be able to dispense products even if they are unrecognized. The system may be disabled, however, temporarily to prevent damage to the dispenser or to prevent over or under dispensing if unrecognized product is detected. The system may not "lock out" unrecognized product as a default setting may be employed to ensure a sufficient amount of unrecognized product may be dispensed. This feature can be applied to other product formats such as, but not limited to, folded paper, diapers, feminine products and the like.

Figure 30:
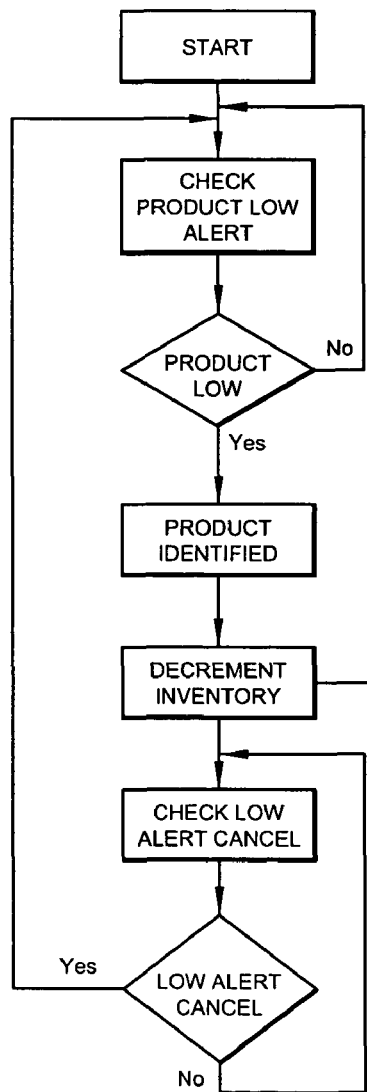
FIG. 30 is a sequence diagram of the automatic reordering of product in accordance with an exemplary embodiment.
Figure 30:
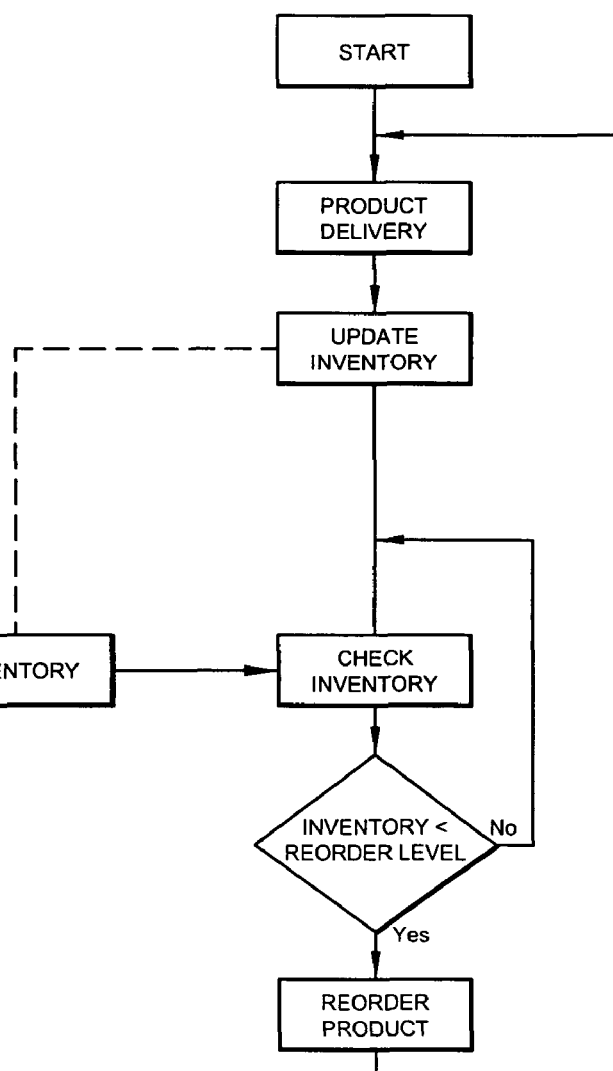

The capability of detecting product low and the capability of detecting product type together provide a method for replenishing an inventory of product. Through a database the system may keep a record of the number of times that a low supply level for the recognized product has been alerted. A method of recording the current inventory and then automatically reordering and billing a customer for the amount of product consumed is provided as another aspect of the invention. FIG. 30 shows a sequence diagram of the product consumption and automatic reordering mechanism. The product consumption process and the automatic reordering process are shown as two separate processes operating upon a common inventory database. The database may be held on the WMS 1040 or may be held on a database at a central location.

The product consumption diagram in FIG. 30 shows the WMS 1040 checking for product low alerts. Alerts are associated with specified product types through the product identification feature. When an alert is annunciated the product is decremented in the inventory database. If the database is hosted on the WMS 1040 then decrementing the database may be carried out locally. If the database is hosted remotely then it may be decremented by sending a message to the database through the Internet. When the alert is cancelled, the process returns to looking for new alerts.

The automatic product reordering diagram in FIG. 30 shows a product delivery updating the inventory level. The inventory level is then checked until it drops below a predefined minimum. Product is then automatically reordered. This process may be part of the overall database operation. If the database is hosted on the WMS 1040 then re-ordering can be carried out by email or other such method. If the database is hosted centrally then re-ordering can be incorporated into an overall product inventory management process.

Figure 20:
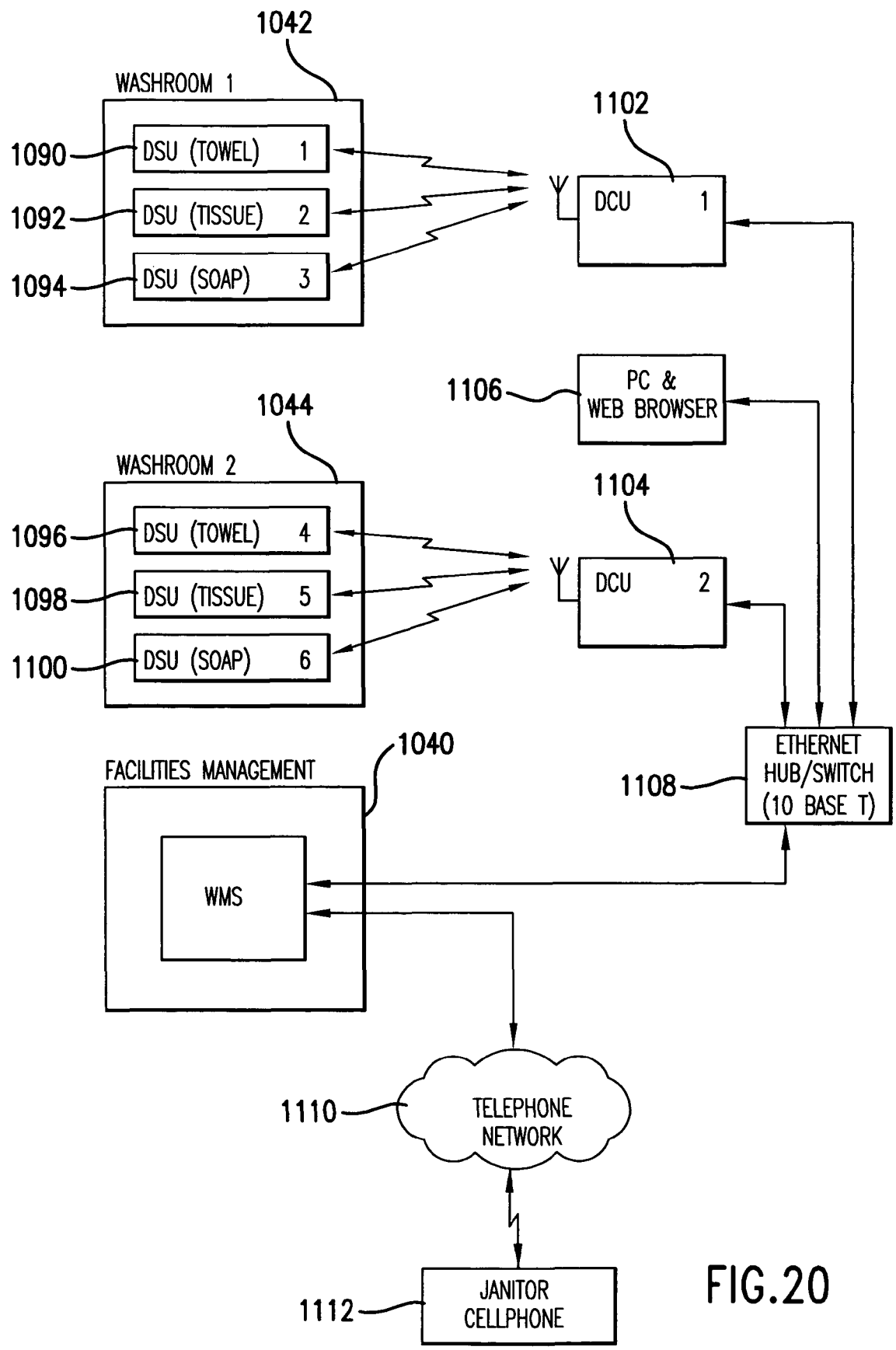
FIG. 20 is a schematic view of the physical relationship between dispenser sensor units, data communication units, a washroom monitoring station, and other components in accordance with an exemplary embodiment.

With reference to FIG. 20 of the drawings, an exemplary embodiment of the operation of a system is shown. FIG. 20 shows two identical washrooms, first washroom 1042 and second washroom 1044. The first washroom 1042 is fitted with a first towel dispenser 1090, a first tissue dispenser 1092, and a first soap dispenser 1094. The second washroom 1044 is fitted with a second towel dispenser 1096, a second tissue dispenser 1098 and a second soap dispenser 1100. Each dispenser is fitted with a dispenser sensor unit (DSU) 1014 and all have the same basic specification of product low detection mechanism, wireless transmitter and battery 1026 with battery level sensor 1028. The transmitter operates in the frequency range 902 MHz to 920 MHz on FM at a maximum output level of 1 mW.

DSUs 1014 from each washroom 1042 and 1044 transmit to separate DCUs 1102 and 1104. Each DCU 1102 and 1104 has a corresponding wireless receiver. FIG. 20 shows a facilities management suite, part of which includes a WMS 1040. The WMS 1040 and both DCUs 1102 and 1104 communicate over 10 BaseT Ethernet through a switch device or hub 1108. The WMS 1040 is also connected to a standard telephone network 1110 so that relevant alerts can be made to a cell phone 1112 carried by a janitor or maintenance personnel.

In this embodiment, the function of the DCUs 1102 and 1104 is to receive and process signals from the DSUs 1090, 1092, 1094, 1096, 1098 and 1100. Each DCU 1102 and 1104 relay alerts to indicate low product, low batteries, or other faults to the WMS 1040. In addition, each DCU 1102 and 1104 includes a web server so that information may be viewed from a web browser running on a computer 1106 attached to the network. If the network is connected to the Internet, the information may be viewed remotely.

In the exemplary embodiment shown in FIG. 20, the function of the WMS 1040 is to receive and process alerts from the DSUs 1090, 1092, 1094, 1096, 1098, and 1100 in its configuration. Alerts are displayed and can be audibly annunciated by the WMS 1040. In addition some or all alerts can be sent to the cell phone 1112. The preferred method of annunciation to a cell phone 1112 is through the short message service (SMS) that is normally a feature available from most cell phone service providers. However, the system is not limited to this method of annunciation and can include alerts via email, radio paging and audible alerts by telephone.

The communication in FIG. 20 may be bi-directional in that the DSUs 1090, 1092, 1094, 1096, 1098, and 1100 or dispensers associated therewith may be reprogrammed or controlled by the PC and web browser 1106, DCUs 1102, 1104, the WMS 1040, or by cell phone 1112. Electrical control circuits or motors contained within various dispensers 1000, 1060, or 1088 may be in communication with the aforementioned components such that the amount of sheet material or soap dispensed from the dispenser can be controlled remotely. For instance, the user may through the WMS 1040 adjust the amount of time a motor in a dispenser 1088 is run, thus causing the dispenser 1088 to dispense at a different amount. Bi-directional controlling may be advantageous in that the adjustment is made remotely without a janitor or maintenance personnel actually visiting the washroom.

It is to be understood that in accordance with various exemplary embodiments, the WMS 1040 may communicate directly with the DSU 1014 without the need for the DCU 1038 to be present.

Figure 21:
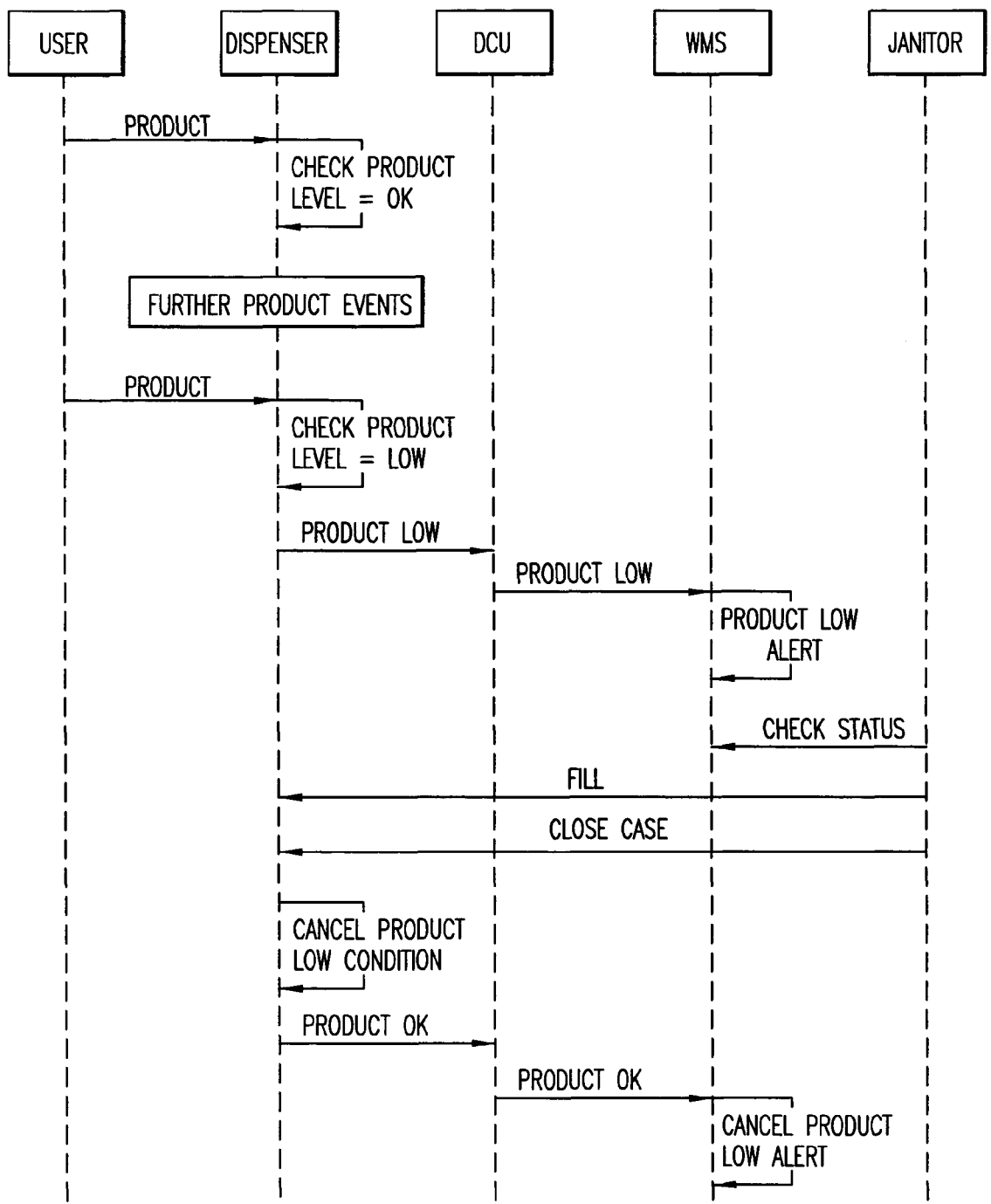
FIG. 21 is a sequence diagram of a product low alert and refill sequence in accordance with an exemplary embodiment.
Figure 22:
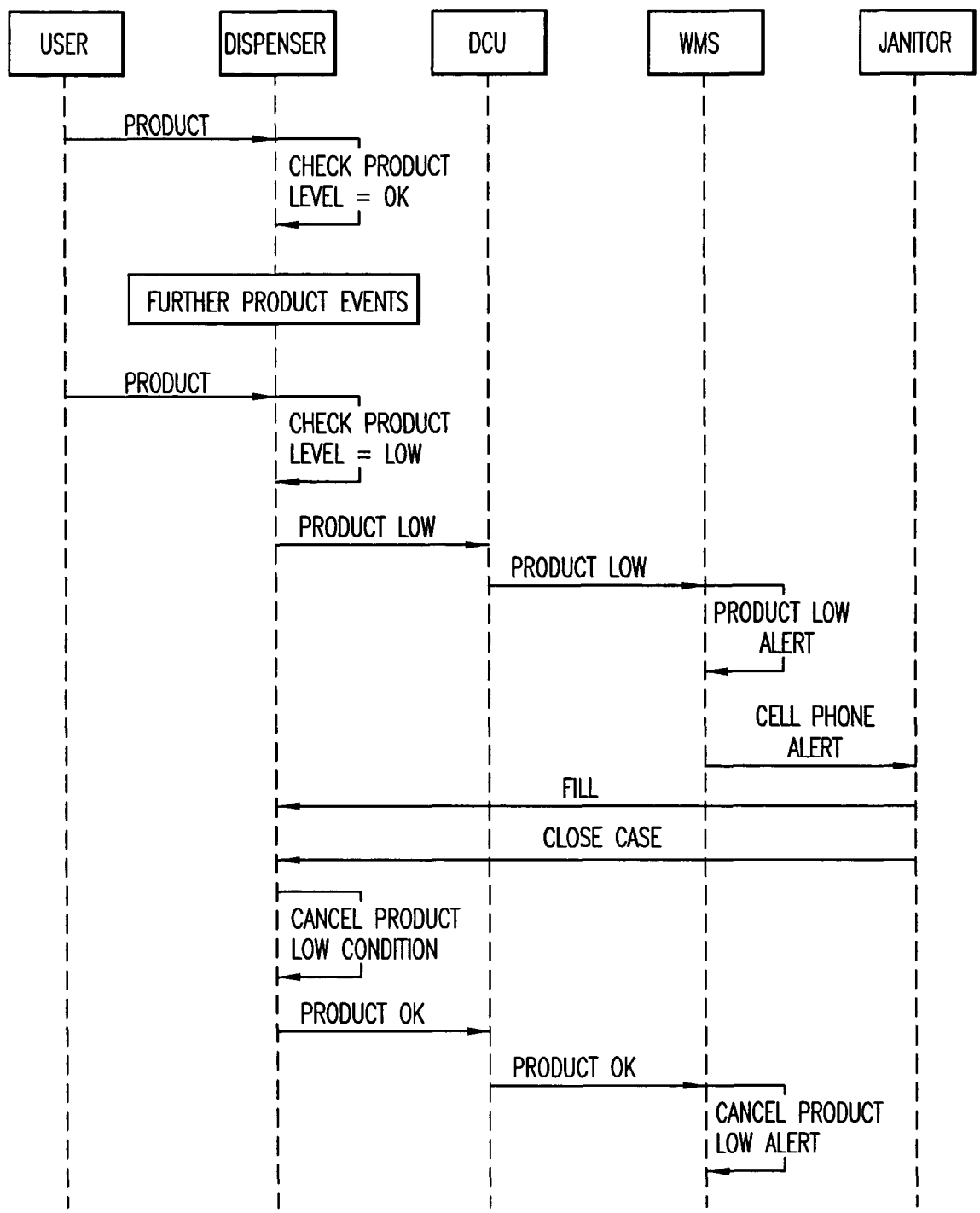
FIG. 22 is a sequence diagram of a product low alert that is sent to a cell phone of a janitor or other maintenance personnel in accordance with an exemplary embodiment.

The drawings in FIGS. 21-26 are sequence diagrams that show particular sets of activities and events between washroom users, components of the system and janitorial functions. FIG. 21 shows a product low alert and refill sequence. The janitor or maintenance personnel periodically checks the status of the dispensers in the system from the WMS 1040 and takes action to refill a dispenser when a product low alert occurs. FIG. 22 is a similar diagram to that of FIG. 21 except where the alert is made to a cell phone 1112 held by the janitor or maintenance personnel so that the WMS 1040 does not need to be checked periodically.

Figure 23:
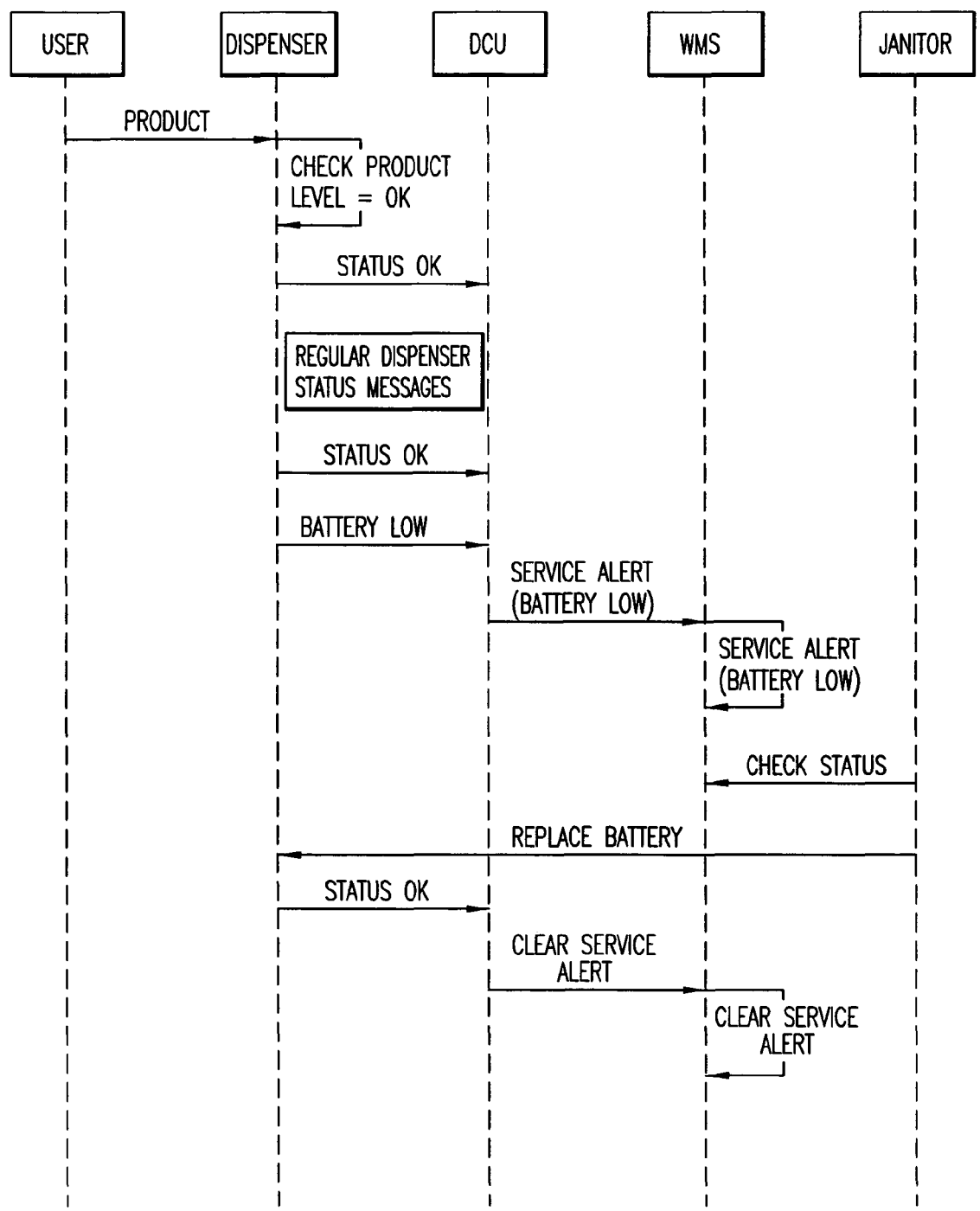
FIG. 23 is a sequence diagram of a battery low alert and a battery change out in accordance with an exemplary embodiment.
Figure 24:
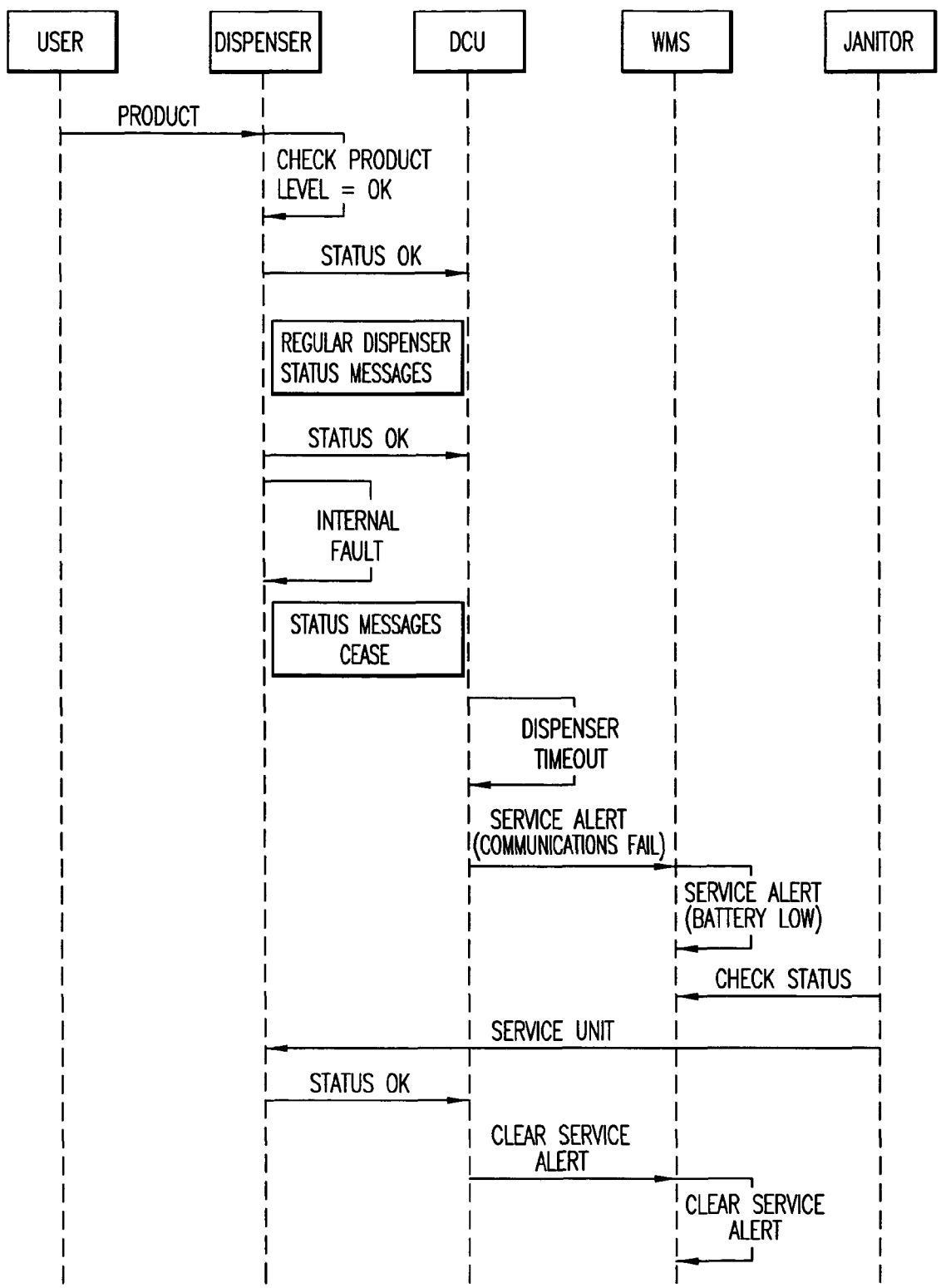
FIG. 24 is a sequence diagram of a dispenser sensor unit communications error and related alert and service in accordance with an exemplary embodiment.

FIG. 23 shows a dispenser battery low alert followed by a battery 1026 change out by the janitor or maintenance personnel. FIG. 24 shows a DSU 1014 communications failure and subsequent alert. The failure is detected by the DCU 1038 since the DCU 1038 receives product status signals from the DSU 1014. When these disappear after a predetermined period of time an alert is generated. The alert is cleared once the system has been serviced.

Figure 25:
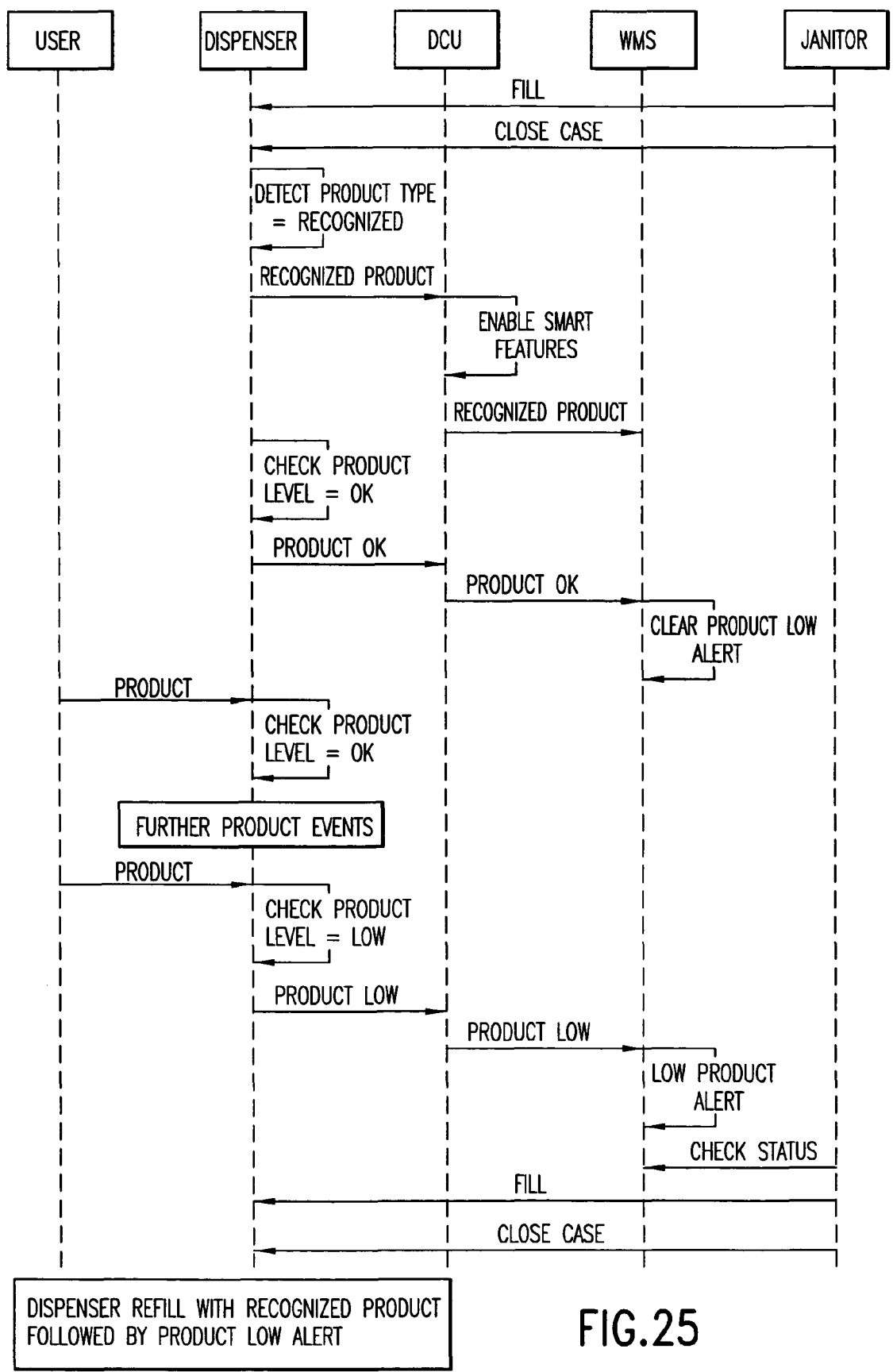
FIG. 25 is a sequence diagram of a system incorporating product recognition in accordance with an exemplary embodiment.
Figure 26:
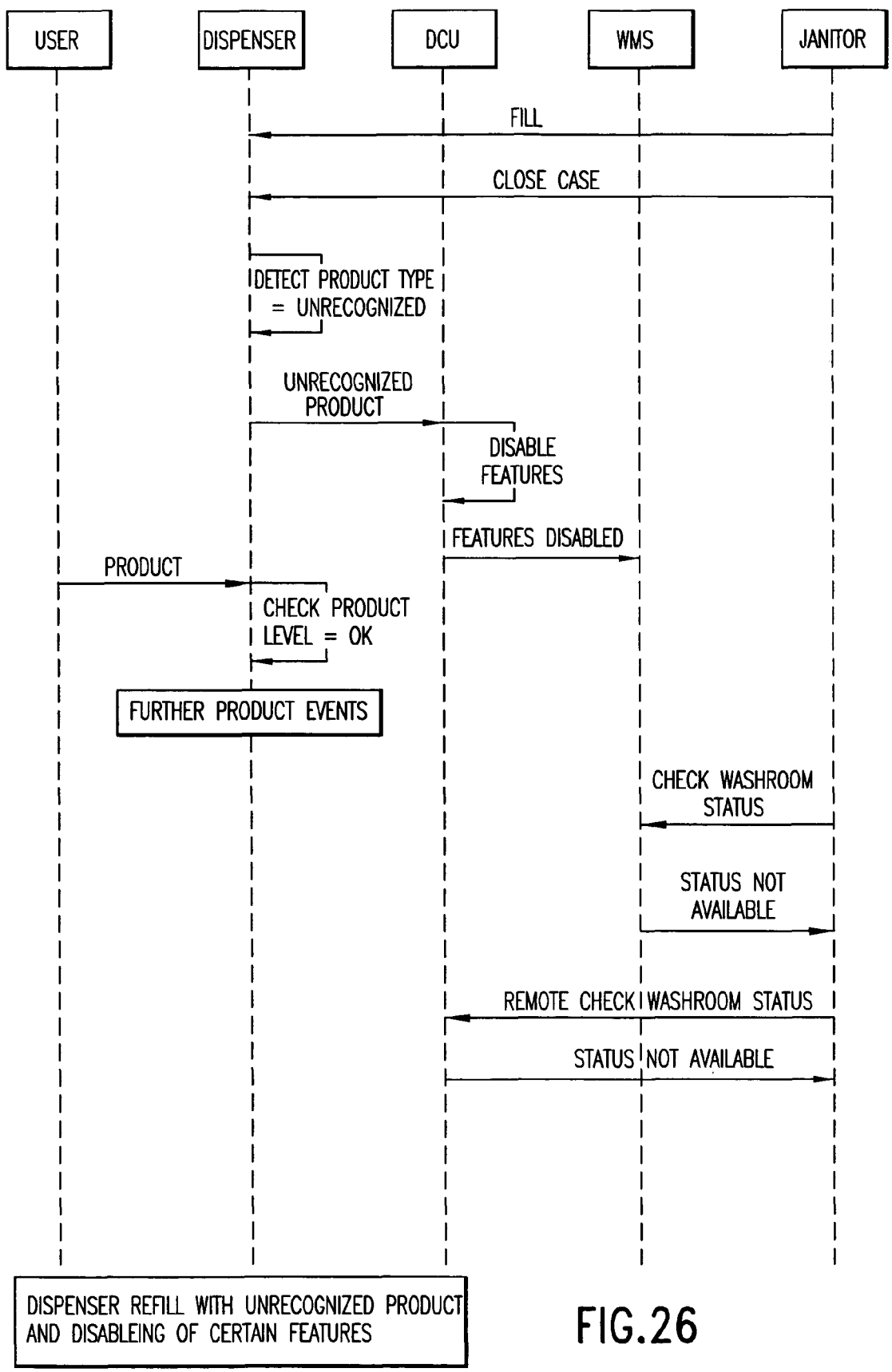
FIG. 26 is a sequence diagram of a system incorporating product recognition and disablement of higher-level functions in accordance with an exemplary embodiment.

FIG. 25 shows the DSU 1014 incorporating product recognition where recognized product is being used. In this instance, higher features such as product low status may be activated. FIG. 26 shows a DSU 1014 with product recognition where unrecognized product is being used. In this instance, the higher level features that allow the user to monitor the status of a dispenser are disabled. However, the dispenser will still be configured to dispense recognized product.

With reference to FIGS. 19A and 19B an embodiment of the control of dispenser parameters will now be described. Dispenser parameters can be defined as, but not limited to, shot size for soap dispensers or air freshener dispensers, sheet length for towel or tissue dispensers, time delay, light sensitivity, and volume. FIGS. 19A and 19B show an automatic soap dispenser 1088, but it is not the intent to limit the scope of the invention to one type of dispenser. Various types of dispensers may be used in this aspect of the invention, the automatic soap dispenser 1088 is used for sake of example.

Typically a dispenser 1088 of this type dispenses a fixed amount of product for each use. This specific amount is generally referred to as the shot size. The shot size is normally fixed for a particular type of dispenser. In an embodiment of the DSU 1014 that contains a communications transceiver and where the DSU 1014 is connected directly or indirectly to the electronics concerned with controlling the dispensing of soap, the administrator of a system can change the shot size by signaling to the DSU. The administrator may do this from the WMS 1040 or it may be done from a cell phone 1112 or other component of the system. Therefore, the present invention provides in one embodiment a system that allows one to communicate to the DSU 1014 or product dispenser 1088 as opposed to a system that is one directional. This feature would be used, for example, to set a larger shot size for areas where users typically have more heavily soiled hands or to select a smaller shot size where a more concentrated type of soap is being used. In accordance with other exemplary embodiments, the DSU 1014 may include an electronic component that is capable of communicating with the DCU 1038, and the DSU 1014 may include a mechanical component that is capable of varying the shot size or other dispensing parameter of the dispenser 1088.

Additionally, where the dispenser 1088 has the capability to recognize the type of product being used and sets the shot size and/or time delay between dispenses automatically, the user has the ability to override the automatic setting. In a similar manner as described above, FIGS. 18A and 18B show another example specifically related to a roll towel dispenser 1060 with the capability to recognize the type of product being used and to set the towel length and/or time delay between dispenses automatically. In this exemplary embodiment, the user may have the ability to override the automatic setting.

Figure 29:
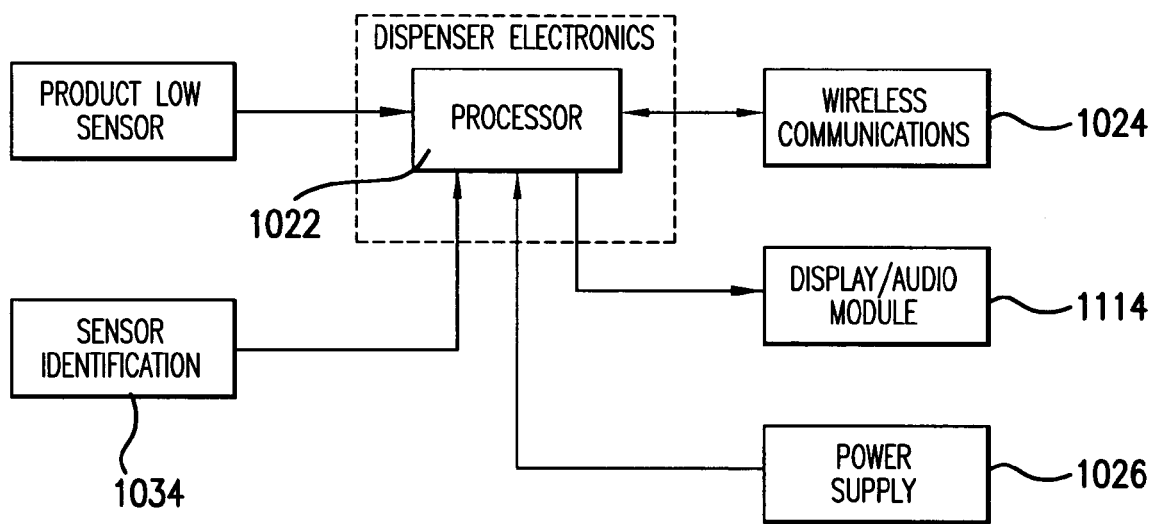
FIG. 29 is a schematic view of the dispenser electronics that may be used with the roll towel dispensers in FIGS. 27A and 28A in accordance with an exemplary embodiment.

Referring to FIGS. 27A and 27B another embodiment is shown. With the capability of controlling dispenser 1060 parameters, additional features can be built into dispensers 1060. FIGS. 27A and 27B show front and side views, respectively, of a roll towel dispenser 1060 similar to the one in FIG. 18A. The dispenser 1060 is fitted with a display module that may be a visual display 1114. The visual display 1114 may be of the liquid crystal type (LCD) or other suitable display technology either monochrome or color, text and/or graphics. The visual display 1114 is connected to the DSU 1014 that in turn is connected directly or indirectly to the dispenser electronics. FIG. 29 shows an exemplary embodiment of the internal arrangement of a DSU 1014 that may be used in the dispenser 1060 in FIGS. 27A and 27B. The DSU 1014 is fitted with a wireless transceiver or communications electronics 1024 to receive control signals from a system administrator. The product low sensor may be of any type previously discussed such as an infrared transmitter and receiver 1030 and 1032.

Figure 32:
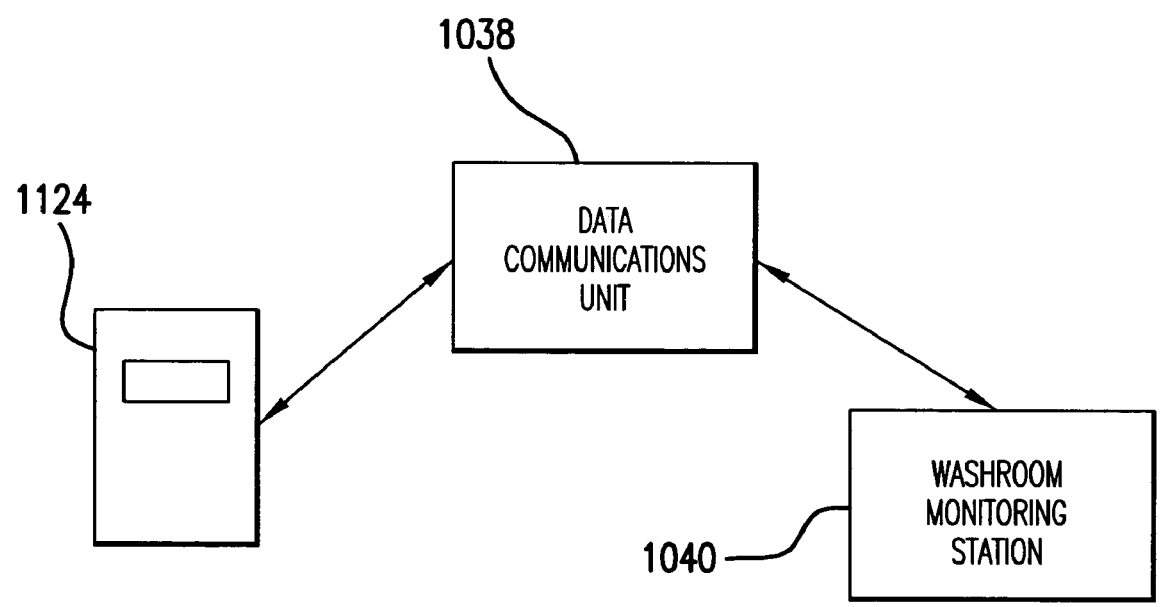
FIG. 32 is a schematic view of a washroom display unit in communication with a data communications unit and a washroom monitoring station in accordance with one embodiment.

A further embodiment may be a stand-alone washroom display unit 1124, one not connected with a dispenser 1060 as shown for example in FIG. 32. The washroom display unit 1124 may have the same basic internal arrangement as described above but without the product low sensor. The washroom display unit 1124 may communicate with a DCU 1038 that is in communication with a WMS 1040. The WMS 1040 may be configured so as to communicate back through the DCU 1038 to the washroom display unit 1124 in order to vary the message sent by the washroom display unit 1124. The change in message may be made automatically or may be done through an operator.

In use, the visual display 1114, in both embodiments described above, can show various information to the users of a washroom including, but not limited to, prompting the users to wash their hands thoroughly, advertising information and weather alerts. The system administrator through the WMS 1040 may change display information at any time.

A further embodiment is shown in FIGS. 28A and 28B. Here, the dispenser 1060 is similar to the embodiment shown in FIGS. 27A and 27B but instead includes a device or appliance for issuing audio messages. The dispenser 1060 includes an audio module 1116. The audio module 1116 may use solid state technology with pre-recorded voice or text-to-voice as examples that may be updated and changed remotely. The audio module 1116 may be connected to the DSU 1014 that in turn is connected directly or indirectly to the dispenser 1116 electronics. FIG. 29 shows the internal arrangement of the DSU 1014 that may be used in one exemplary embodiment of the present invention. The DSU 1014 is fitted with a wireless transceiver or communication electronics 1024 so as to receive control signals from a system administrator. The audio module 1116 may be stand-alone, such as shown in FIG. 32 and described above only with audio messages, or may be incorporated into another item such as an air freshener, towel dispenser or the like. The audio module 1116 can broadcast music, white noise or various information to users of a washroom including, but not limited to, special promotions, events or reminders to wash one's hands before leaving the washroom. The administrator can adjust particular parameters of the device such as, but not limited to, time intervals between each message, volume, gender voice, multiple languages and the like. The system administrator through the WMS 1040 may change audio information at any time. Additionally, a stand alone module may be included in certain exemplary embodiments that displays visual messages that may be in communication with a DCU 1038 either wirelessly or by hard wire. The module could also be configured to display both visual and audio messages.

When configured as a stand-alone, the audio module 1116 is not connected with a dispenser 1060. This exemplary embodiment has the same basic internal arrangement as described above but without the product low sensor or product recognition. One type of such device is described in U.S. patent application Ser. No. 10/950,965 titled "A Device For Encouraging Hand Wash Compliance" filed Sep. 27, 2004, which is incorporated by reference in its entirety herein for all purposes. It is to be understood, however, that the audio module 1116 may be configured to display only visual messages or both audio and visual messages in other exemplary embodiments.

Figure 34:
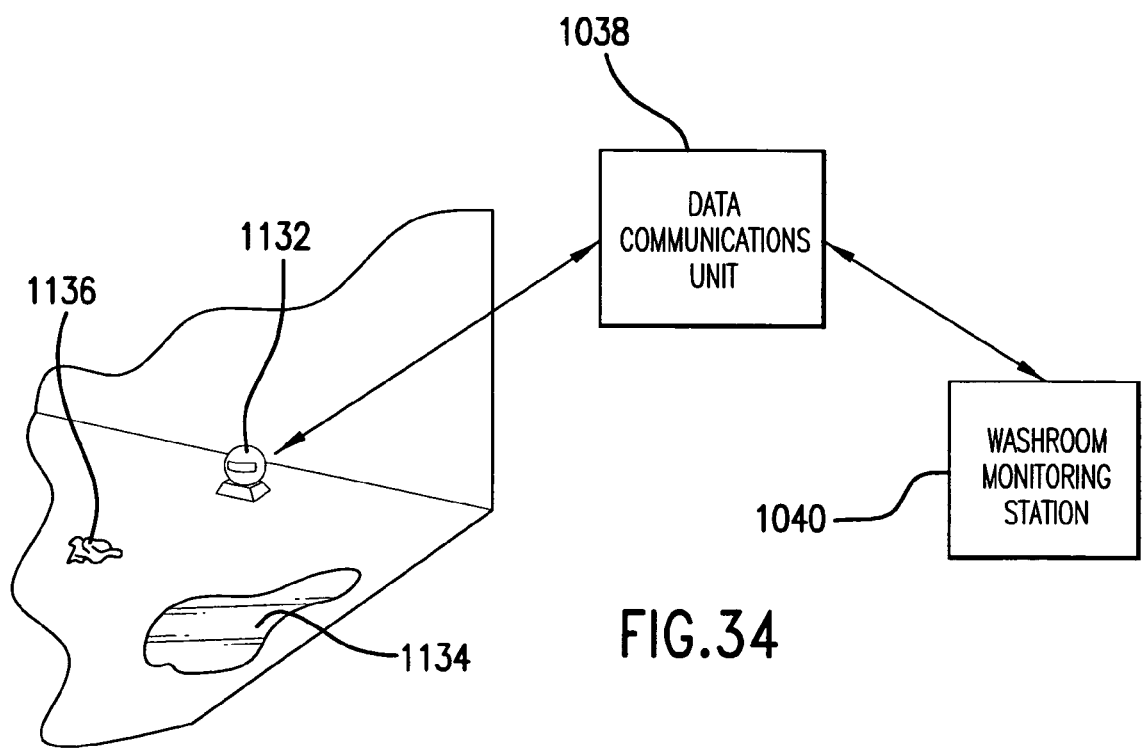
FIG. 34 is a schematic view of a camera in communication with a data communications unit and a washroom monitoring station in accordance with one embodiment.

FIG. 34 is a schematic view of a further exemplary embodiment. Here, a camera 1132 is positioned so as to be capable of viewing a floor of a washroom. The camera 1132 is capable of viewing water 1134 that may be present on the floor from an overflowed sink, toilet or urinal. Additionally, the camera 1132 may be capable of viewing debris 1136, such as used paper towels, that may be thrown onto the washroom floor. The camera 1132 may be configured so as to be capable of viewing only about three inches or less from the top of the floor of the washroom in order to address any privacy concerns.

The camera 1132 may be in communication with a DCU 1138 that is in turn in communication with a WMS 1040. A user may monitor the washroom floor through the WMS 1040 and alert maintenance personnel if water 1134 and/or debris 1136 are detected. Additionally or alternatively, the system may be configured so that the camera 1132, DCU 1038 or WMS 1040 may automatically alert the presence of water 1134 and/or debris 1136 should they become present.

An automatic device for flushing a urinal or toilet normally uses an infrared detector to determine when the urinal has been used. In accordance with the present invention, such a device may incorporate a unit similar to a DSU 1014 to signal use of the urinal or toilet and to prompt the user to wash his hands before leaving the washroom 1042 though a washroom display as described previously in FIG. 27A, 27B, 28A or 28B.

Other exemplary embodiments are also included that involve devices and functions peripheral to the operation of dispensers 1060 but pertinent to the functioning of a washroom in regard to monitoring and controlling various equipment. The first embodiment describes an overflow sensor 1118 as shown for example in FIG. 31 for individual sinks, toilets, urinals, and/or floor areas adjacent thereto to provide advanced warning of a water overflow or flood situation. The overflow sensor 1118 may be capable of being fitted discreetly to a sink, toilet or urinal for detecting the presence of water. The overflow sensor may have internal structure similar to the DSU 1014 as previously described in order to communicate with a DCU 1038.

The overflow sensor 1118 includes but is not limited to the following: moisture detector, pressure sensor and float switch. A moisture detector may include a resistance bridge in which contact with water forms one side of the bridge. The bridge may be capable of detecting the difference between an open circuit and resistances below 5 MOhm. A pressure sensor may include a water resistant diaphragm capable of detecting slight differences in pressure between the lack of water and immersion in water above a nominal 2 cm or approximately 0.2 kPa. A float switch may include a small float attached to an arm that throws a switch when water reaches a predetermined level.

The DSU 1014 may be housed in a waterproof case to protect the electronics and battery 1026. In use, the overflow sensor 1118 detects the presence or absence of water. If the presence of water is sustained for a period of time in excess of the usual flushing period an alert is signaled to the DSU 1014 or other component in communication with the overflow sensor 1118. For example, the overflow sensor 1118 may signal the presence of water if water is detected for an amount of time over 20 seconds, 30 seconds, 40 seconds, or for an amount of time between 30 and 45 seconds. The WMS 1040 administrator is alerted to an overflow condition by the WMS 1040 and takes action should an alert occur. A sensor may be used with the DSU in order to detect the flow of water to further determine an overflow or potential flood condition. FIG. 22 is a similar diagram except where the alert is made to a cell phone or PDA 1112 held by the janitor or maintenance personnel so that the WMS 1040 does not need to be checked periodically.

Figure 31:
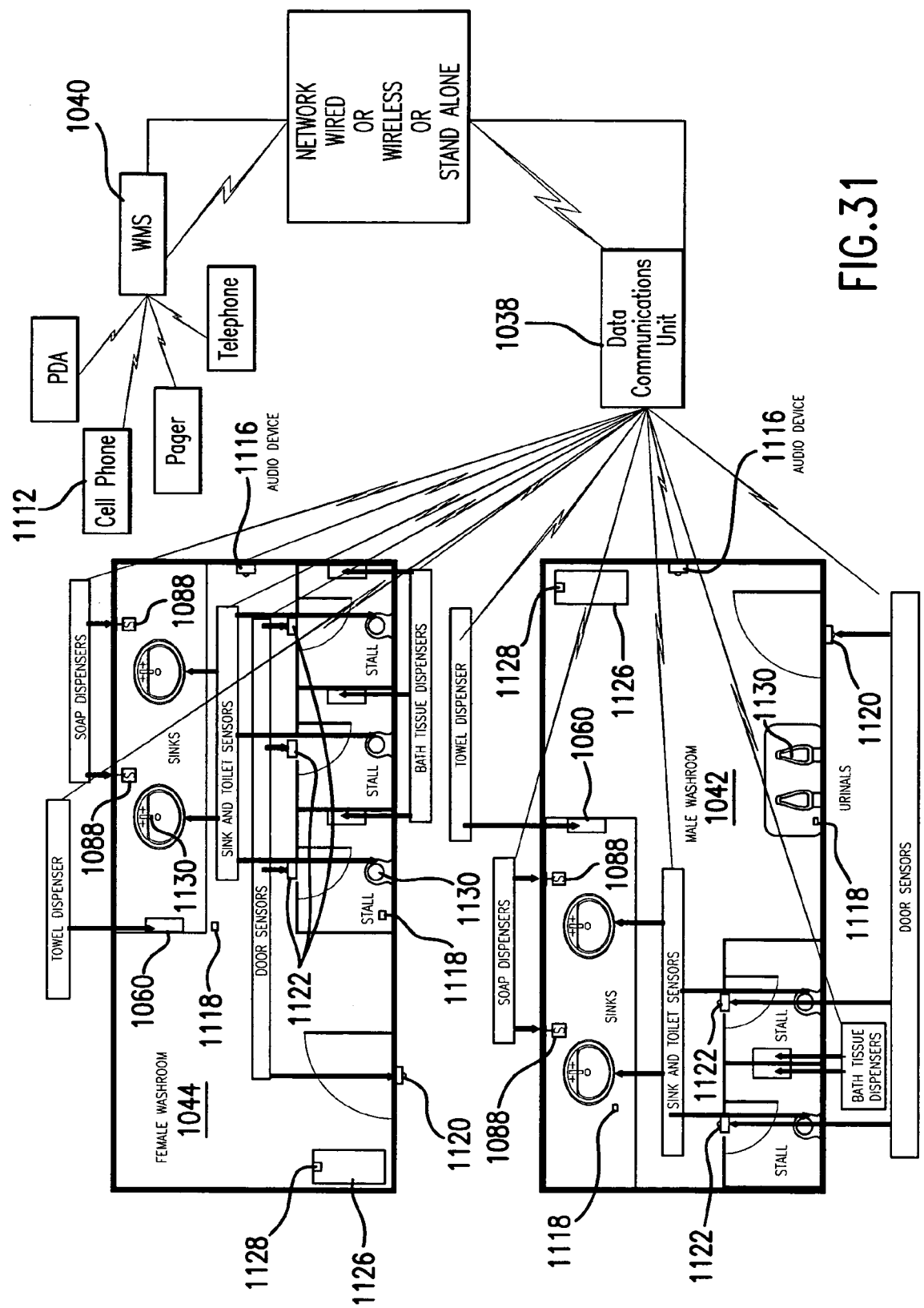
FIG. 31 is a schematic view of a system for monitoring, reporting and analysing various washroom components in accordance with an exemplary embodiment.

In addition, an apparatus may be included for monitoring and controlling the flow of water to determine if excess water is being used by a faucet, toilet and/or urinal that is left running. A data communications unit 1038 may be in communication with a flow sensor 1130 as shown in FIG. 31. Further, a WMS 1040 may be included and may be in communication with the data communications unit 1038 and with the flow sensor (s) 1130 through the data communications unit 1038. The WMS 1040 may be configured for indicating the flow of water when detected by the flow sensor(s) 1130. The flow sensor(s) 1130 may be selected from a variety of sensors including, but not limited to, a rotating vane and/or differential pressure unit.

The following embodiments incorporate the ability for washroom devices other than those previously described to utilize monitoring and controlling. The following are by way of example: An automatic air freshener device typically uses a mechanism for periodically releasing an aerosol valve. Incorporation of a DSU 1014 into this device may be advantageous. First, when the aerosol requires replacing, the DSU 1014 may signal an alert instead of emitting an annoying sound, as is common practice. Second, the system could control when the air freshener releases the aerosol so that the product is used in an efficient way. A DSU 1014 may be incorporated into other devices used within a washroom 1042 or 1044 for the purposes of monitoring or controlling, such as waste receptacles, to determine when to empty or detect overflow situations. The WMS 1040 administrator periodically checks the status of the waste receptacle sensors from the WMS 1040 and takes action should an alert occur.

A DSU 1014 may be incorporated into other devices used within a washroom for the purposes of monitoring or controlling, such as waste receptacles as previously mentioned, to determine when to empty or detect overflow situations. A sensor 1128 for a waste receptacle 1126 includes but is not limited to a mechanical switch, infrared or other proximity sensing device, strain gauge or pressure sensor. A mechanical switch can be mounted on to the lid of a waste receptacle 1126. When the receptacle 1126 is full and the lid and switch remain open for an extended period of time an alert can be signaled. Alternatively the switch can be used to count the number of times the lid has been opened and closed. The DSU 1014 can infer that the waste receptacle 1126 is full after a certain number of counts, pre-determined for each receptacle 1126 type. An infrared sensor can be mounted onto the side of the receptacle 1126 and so long as the liner used to contain the refuse is transparent, the sensor can be used to signal an alert when the level of refuse reaches a particular point. A strain gauge or pressure sensor can be used to weigh the contents of the receptacle. At a pre-determined weight an alert can be signaled.

FIG. 31 shows a waste receptacle 1126 that includes a waste receptacle sensor 1128 that may be in communication with the WMS 1040 through the DCU 1038 or other component such as the DSU 1014. Examples of devices that can be used are infrared measuring sensors or mechanical switches, however, it should be understood that other devices can be used. The WMS 1040 administrator periodically checks the status of the waste receptacle sensors 1128 from the WMS 1040 and takes action should an alert occur. FIG. 22 shows a similar set up in which an alert is made to a cell phone 1112 held by the janitor or maintenance personnel so that the WMS 1040 does not need to be checked periodically.

A further embodiment provides the capability of monitoring and reporting hand washing compliance in public washrooms, nurses' and doctors' lounges and nursing stations in various units of healthcare, food preparation or food processing facilities. This embodiment may expand on previously discussed embodiments to measure washroom traffic or visits as they relate to product usage and in conjunction with controlling dispenser parameters and any combination of audio, text or graphics prompts to remind users to wash their hands before and after contact with a patient or food or other to encourage, quantify and report hand washing compliance.

This exemplary embodiment has the capability of measuring usage which is described in detail in U.S. Pat. Nos. 5,878, 381; 6,360,181; and 6,411,920, the contents of all three are incorporated by reference in their entirety herein for all purposes. With the use of the visual display 1114 and audio module 1116 embodiments described, additional features can be added to monitor the washroom traffic and hand washing compliance. FIG. 31 shows a first washroom 1042, that may be a male washroom, and a second washroom 1044, that may be a female washroom. Door or entrance sensors 1120 are provided, as are stall door sensors 1122 that are used to determine when the doors or stalls are opened or closed or detect movement therewith. Sensors, such as but not limited to, infrared or ambient light sensors may also or alternatively be used to sense the presence of the user in the washrooms 1042, 1044. Events are time and date stamped to enable correlation of visits to the washrooms 1042, 1044 with usage from, but not limited to, towel dispensers 1060, tissue dispensers 1060, soap dispensers 1088 and the like to determine compliance. Such an arrangement may also include a magnet and associated read switch attached to the washroom 1042, 1044 doors or to stall doors for detecting movement therewith.

In operation, a user would enter the washroom 1042 or 1044 and have his or her presence noted by one of the sensors 1120 or 1122. As the individual uses the dispenser 1060 or 1088, the displacement of the product is monitored and recorded. The products of such analysis may further be stored in the memory area of the dispensers 1060 or 1088 for further analysis and/or retrieval. When the user leaves the washroom 1042, 1044 this is also recorded by one of the sensors 1120 or 1122 referenced above. Sensors that are used to monitor individuals in the washroom 1042 or 1044 may be configured so as to be able to detect and discern the identity of individual users of the washroom through mechanisms commonly known to those of ordinary skill in the art, including but not limited to RFID technology or bar codes. U.S. patent application Ser. No. 10/950,965 titled "A Device For Encouraging Hand Wash Compliance" filed Sep. 27, 2004, which is incorporated by reference in its entirety herein for all purposes, shows various ways in which hand washing compliance may be conducted.

The system can utilize non-network audio modules 1116 or visual display devices 1114 to send reminders continuously or intermittently or set to broadcast in the event a user enters the washroom 1042 or 1044, enters and exits the stall and/or leaves the washroom 1042 or 1044 without a correlating towel 1060 and/or soap dispenser 1088 event occurring. With respect to networked devices, the administrator can adjust particular parameters of the device such as but not limited to time intervals between each message, volume, gender voice, multiple languages and the like. The system administrator through the WMS 1040 may change audio information at any time.

An automatic device for flushing a urinal normally uses an infrared detector to determine when the urinal or toilet has been used. Such a device incorporating a DSU 1014 may be able to signal its use and prompt the user to wash their hands before leaving the washroom 1142 or 1044 utilizing a washroom display or audio reminder as described previously. The system administrator through the WMS 1040 may change audio and/or display information at any time. The functionality of the sensors, statistics, refill status of the dispensers, etc., can be monitored in real-time by the administrator of the WMS 1040.

Various methods of identifying an individual such as but not limited to RFID, bar code, or keypad entry are known to those having ordinary skill in the art. The identity of the individual may be maintained in a profile that could be accessed through the WMS 1040 in which is it monitored and alerts sent in real time. An exemplary embodiment provides for the ability to maintain the identity of the individual in a profile that could be accessed through the WMS 1040. A discreet message could be sent to the individual's cell phone 1112, pager or like to remind them that they did not wash their hands before leaving the washroom 1042 or 1044.

Sample Test Carried Out in Accordance with One Exemplary Embodiment

A system was tested in a washroom with the use of SCOTTFOLD® Towels, code 01999 (Loudon). Standard smart dispenser protocol was used. A minimum of 200 events for males and females were obtained to discern a ten percent difference between studies. One case of product will yield about 800 combined hand dries over about a 3½ day period. The hand dries broke down to about 225 for females and 760 for males. Data was collected in three study periods.

Study 1 was conducted for 3 to 4 days prior to using a verbal reminder in order to generate "control" usage data. Study 2 was conducted for 3 to 4 days with a verbal reminder. Study 3 was conducted for 3 to 4 days after the verbal reminder to determine if usage decreases without the reminder.

Simple audio equipment (book case stereo system with repeat feature and individual speakers) was installed in the ceiling above the washrooms. Ceiling tiles were modified to improve sound quality. CD's were used to record and play the verbal reminder on a continuous loop with 45 second sequences between each message. A female voice was used in the women's washroom and a male voice was used in the men's washroom.

Two SCOTTFOLD® Dispensers, a data collection unit, five standard roll bathroom tissue dispensers and corresponding stall door sensors and two door sensors for the primary doors were also used in the experiment.

A door sensor was placed on the primary door to measure the number of people coming in and out of the washroom. Events were time and date stamped. Bathroom tissue events were monitored to determine if the amount corresponded with the number of hand dries, specifically in the female washroom. The smart equipment measured the number of hand dries per study and number of towels per hand dry. The number of hand dries divided by the number of washroom visits equals the percent compliance (#HD/#Visits=% Compliance).

A few "uncontrollable variables" existed in the experiment that may cause some variability in the data obtained. First, the number of "visits" measured in the studies does not take into account the possibility of multiple people entering or exiting the washroom at the same time. Second, there was no way of determining janitorial, maintenance or miscellaneous visits from true events. Finally, the door signals were manually counted. The data obtained may be found in Table 1 below:

TABLE 1

| | Females | | | |
|---|---|---|---|---|
| Study # | # Female Visits | # Female Stall Events | # Female Hand Wash | Towels/ Hand Dry |
| 1 (before) | 279 | 243 | 226 | 1.85 |
| 2 (message) | 241 | 194 | 228 | 1.94 |
| 3 (after) | 275 | 257 | 256 | 1.82 |

| | Percentage of Stall/Visits | Percentage of H Wash/Visits | Visits/HD Sig Diff |
|---|---|---|---|
| 1 (before) % | 87.10% | 81.00% | A |
| 2 (message) % | 80.50% | 94.61% | B |
| 3 (after) % | 93.45% | 93.09% | B |

| | Males | | | |
|---|---|---|---|---|
| Study # | # Male Visits | # Male Stall Events | # Male Hand Wash | Towels/ Hand Dry |
| 1 (before) | 610 | 113 | 535 | 2.14 |
| 2 (message) | 544 | 96 | 538 | 2.15 |
| 3 (after) | 518 | 103 | 511 | 1.98 |

| | Percentage of Stall Event/Visits | Percentage of H Wash/Visits | Visits/HD Sig Diff |
|---|---|---|---|
| 1 (before) % | 18.52% | 87.70% | A |
| 2 (message) % | 17.65% | 98.90% | B |
| 3 (after) % | 19.88% | 98.65% | B |

| | Females/Males Combined | | | |
|---|---|---|---|---|
| Study # | # Female/ Male Visits | # Females/Males Stall Events | # Females/Males Hand Wash | Towels/ Hand Dry |
| 1 (before) | 889 | 356 | 761 | 2.05 |
| 2 (message) | 785 | 290 | 766 | 2.09 |
| 3 (after) | 793 | 360 | 767 | 1.93 |

TABLE 1-continued

| | Percentage of Stall Event/Visits | Percentage of H Wash/Visits | Visits/HD Sig Diff |
|---|---|---|---|
| 1 (before) % | 40.04% | 85.60% | A |
| 2 (message) % | 36.94% | 97.58% | B |
| 3 (after) % | 45.40% | 96.72% | B |

A 12.7 percent increase was found to exist between study 1 and study 2 in the number of hand washes per visit to the rest room from the initial control period to the period with the verbal reminder for both males and females. This increase infers that the verbal reminder influenced hand washing compliance. Additionally, an increase of 11.1 percent was found to exist between study 1 and study 3.

Hand washing compliance remained at the higher level for the 4 day period just after the verbal message was discontinued. It was anticipated that hand washing compliance might gradually decrease when the verbal reminder was terminated. However, there was no discernable difference between the results in study 2 and study 3. Additional testing may be desirable to determine how long the verbal message influences compliance after stopping the message. Additionally or alternatively, it may be desirable to determine the amount of time the same message played over and over remains effective.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An apparatus for the dispensing of product, comprising:
   a dispenser configured for the dispensing of product;
   a dispenser sensor unit in communication with said dispenser and configured for automatically successively detecting more than one different measurement of the amount of product remaining in the dispenser, said dispenser sensor unit configured for varying a dispensing parameter of said dispenser;
   a data communications unit in communication with said dispenser sensor unit and configured for receiving from said dispenser sensor unit information about the amount of product remaining in the dispenser; and
   a washroom monitoring station in communication with said data communications unit and configured for receiving from said data communications unit information about the amount of product remaining in the dispenser;
   wherein said dispenser sensor unit is configured for receiving a communication so as to reduce the dispensing parameter of said dispenser accordingly as the amount of product remaining in the dispenser diminishes.

2. The apparatus as set forth in claim 1, wherein the dispensing parameter is selected from the group consisting of shot size, sheet length, time delay, light sensitivity and volume.

3. The apparatus as set forth in claim 1, wherein said washroom monitoring station is configured for sending the communication to said dispenser sensor unit through said data communications unit in order to cause said dispenser to vary the dispensing parameter of said dispenser.

4. The apparatus as set forth in claim 1, wherein said data communications unit transmits information wirelessly to said washroom monitoring station.

5. The apparatus as set forth in claim 1, wherein said dispenser sensor unit is configured for identifying the product and reporting the identification of the product to said washroom monitoring station through said data communications unit.

6. The apparatus as set forth in claim 5, further comprising a reader in communication with said dispenser sensor unit wherein said reader is selected from the group consisting of an RFID reader, a bar code reader, a printed label reader, a magnetic strip reader, a smart tag reader, a hologram reader, a luminescence reader, and a fluorescence reader.

7. The apparatus as set forth in claim 5, wherein said data communications unit is configured for reporting a low product condition and wherein said data communications unit enables reporting of the low product condition if recognized product is identified.

8. The apparatus as set forth in claim 1, wherein said dispenser is configured for storing product in bulk and said dispenser sensor unit is configured for identifying the product and reporting the identification of the product and the level of product remaining in said dispenser to a database, and further comprising a product reordering mechanism configured for using the database to reorder product when low and to bill for reordered product.

9. The apparatus as set forth in claim 1, wherein said dispenser has a visual display configured for displaying information, wherein said visual display is in communication with said washroom monitoring station through said data communications unit such that said washroom monitoring station is configured for changing display information of said visual display.

10. The apparatus as set forth in claim 1, wherein said dispenser has an audio module configured for announcing an audio message, wherein said audio module is in communication with said washroom monitoring station through said data communications unit such that said washroom monitoring station is configured for changing audio messages of said audio module.

11. The apparatus as set forth in claim 1, wherein said dispenser is selected from the group consisting of a paper towel dispenser, a liquid or foam soap dispenser, a toilet tissue dispenser, and an air freshener dispenser, toilet seat cover dispenser, diaper dispenser, and a feminine product dispenser.

12. The apparatus as set forth in claim 1, further comprising an overflow sensor in communication with said washroom monitoring station through said data communications unit, wherein said overflow sensor is configured for detecting the presence of water.

13. The apparatus as set forth in claim 1, further comprising a water flow sensor in communication with said washroom monitoring station through said data communications unit, wherein said water flow sensor is configured for detecting the flow of water.

14. The apparatus as set forth in claim 1, further comprising a waste receptacle sensor in communication with said washroom monitoring station through said data communications unit, wherein said waste receptacle sensor is configured for detecting the presence of waste in a waste receptacle.

15. The apparatus as set forth in claim 1, wherein said dispenser has a battery and wherein said sensor unit is configured for measuring the battery level of said battery and communicating the battery level to said washroom monitoring station through said data communications unit.

16. The apparatus as set forth in claim 1, wherein said dispenser sensor unit has a battery and wherein said dispenser sensor unit is configured for measuring the battery level of said battery and communicating the battery level to said washroom monitoring station through said data communications unit.

17. The apparatus as set forth in claim 1, wherein said dispenser sensor unit is configured for detecting information about the product that is selected from the group consisting of the amount of product remaining in said dispenser, the amount of product removed from said dispenser, and the rate of product removal from said dispenser.

18. The apparatus as set forth in claim 1, wherein said washroom monitoring station is configured for reporting a product low condition by a device selected from the group consisting of a cell phone, a PDA, a pager, and a telephone.

19. The apparatus as set forth in claim 1, further comprising:
a sensor configured for indicating the presence and identity of an individual user of a washroom;
wherein said dispenser sensor unit is configured for detecting the removal of product from said dispenser;
wherein said data communications unit is in communication with said sensor; and
a washroom monitoring station in communication with said data communications unit, wherein said washroom monitoring station is configured for receiving information from said dispenser sensor unit and said data communications unit so as to monitor product removal by the individual.

20. The apparatus as set forth in claim 19, wherein said dispenser is selected from the group consisting of a paper towel dispenser, a soap dispenser, a toilet tissue dispenser, a sink, toilet, and urinal.

21. The apparatus as set forth in claim 19, wherein said washroom monitoring station is configured for reporting lack of product removal to the individual by a device selected from the group consisting of a cell phone, a PDA, a pager and a telephone.

22. The apparatus as set forth in claim 19, wherein said sensor communicates with said dispenser sensor unit such that presence and identity information is communicated to said data communications unit from said sensor through said dispenser sensor unit.

23. The apparatus as set forth in claim 19, further comprising a display configured for conveying information and in communication with said washroom monitoring station, and wherein said washroom monitoring station is configured for effecting display information.

24. The apparatus as set forth in claim 23, wherein said display is selected from the group consisting of a visual display and an audio module.

25. The apparatus as set forth in claim 19, wherein said dispenser sensor unit is in wireless communication with said data communications unit, and wherein said data communications unit is in wireless communication with said washroom monitoring station.

26. An apparatus for the dispensing of product, comprising:
a dispenser configured for the dispensing of product;
a dispenser sensor unit in communication with said dispenser and configured for detecting information about the product, said dispenser sensor unit configured for varying the rate of dispensing product from said dispenser;
a data communications unit in communication with said dispenser sensor unit and configured for receiving information from said dispenser sensor unit;
a washroom monitoring station in communication with said data communications unit and configured for receiving information from said data communications unit about the amount of product in said dispenser and for returning to said data communications unit a communication to vary the rate of dispensing product from said dispenser in accordance with said information about the amount of product in said dispenser;
wherein said dispenser sensor unit is configured for receiving a communication from a cell phone so as to cause said dispenser to vary the rate of dispensing product from said dispenser according to the amount of product in said dispenser.

27. An apparatus for the dispensing of product, comprising:
a dispenser configured for the dispensing of product;
a dispenser sensor unit in communication with said dispenser and configured for detecting information about the product, said dispenser sensor unit configured for varying the rate of dispensing product from said dispenser;
a data communications unit in communication with said dispenser sensor unit and configured for receiving information from said dispenser sensor unit;
a washroom monitoring station in communication with said data communications unit and configured for receiving information from said data communications unit about the amount of product in said dispenser and for returning to said data communications unit a communication to vary the rate of dispensing product from said dispenser in accordance with said information about the amount of product in said dispenser;
wherein said dispenser sensor unit is configured for receiving a communication from a PDA so as to cause said dispenser to vary the rate of dispensing product from said dispenser according to the amount of product in said dispenser.

28. An apparatus for the dispensing of product, comprising:
a dispenser configured for the dispensing of product;
a dispenser sensor unit in communication with said dispenser and configured for detecting information about the product, said dispenser sensor unit configured for varying a dispensing parameter of said dispenser;
a data communications unit in communication with said dispenser sensor unit and configured for receiving information from said dispenser sensor unit;
a washroom monitoring station in communication with said data communications unit and configured for receiving information from said data communications unit;
wherein said dispenser sensor unit is configured for receiving a communication so as to reduce the dispensing parameter of said dispenser accordingly as the amount of product remaining in the dispenser diminishes;
a hub interconnecting with both said data communications unit and said washroom monitoring station; and
a computer interconnecting with said hub, wherein said computer employs a web browser for viewing information sent via said hub.

29. An apparatus for the dispensing of soap, comprising:
a soap dispenser configured for the dispensing of soap;
a dispenser sensor unit in communication with said dispenser and configured for automatically successively detecting more than one different measurement of the amount of soap in said dispenser, said dispenser sensor unit configured for varying the shot size of said dispenser;
a data communications unit in wireless communication with said dispenser sensor unit and configured for receiving information from said dispenser sensor unit that includes at least the amount of soap remaining in said dispenser; and
a washroom monitoring station in wireless communication with said data communications unit and configured for receiving information from said data communications unit that includes at least the amount of soap remaining in said dispenser, and wherein said washroom monitoring station is configured for communicating with said dispenser sensor unit through said data communications unit to vary the shot size of said dispenser depending upon the amount of soap detected in said soap dispenser.

* * * * *